(12) United States Patent
McKinney et al.

(10) Patent No.: US 12,042,481 B2
(45) Date of Patent: Jul. 23, 2024

(54) USE OF (1R,5S)-(+)-1-(NAPHTHALEN-2-YL)-3-AZABICYCLO[3.1.0]HEXANE IN THE TREATMENT OF CONDITIONS AFFECTED BY MONOAMINE NEUROTRANSMITTERS

(71) Applicant: OTSUKA AMERICA PHARMACEUTICAL, INC., Rockville, MD (US)

(72) Inventors: Anthony Alexander McKinney, Cambridge, MA (US); Frank Bymaster, Brownsburg, IN (US)

(73) Assignee: OTSUKA AMERICA PHARMACEUTICAL, INC., Rockville, MD (US)

( * ) Notice: Subject to any disclaimer, the term of this patent is extended or adjusted under 35 U.S.C. 154(b) by 502 days.

(21) Appl. No.: 17/200,719

(22) Filed: Mar. 12, 2021

(65) Prior Publication Data
US 2021/0267940 A1 Sep. 2, 2021

Related U.S. Application Data

(63) Continuation of application No. 13/907,921, filed on Jun. 2, 2013, now abandoned, which is a continuation of application No. 13/751,169, filed on Jan. 28, 2013, now abandoned, which is a continuation of application No. 13/528,940, filed on Jun. 21, 2012, now abandoned, which is a continuation of application No. 13/334,066, filed on Dec. 22, 2011, now abandoned.

(60) Provisional application No. 61/574,231, filed on Jul. 30, 2011.

(51) Int. Cl.
A61K 31/403 (2006.01)
A61K 45/06 (2006.01)

(52) U.S. Cl.
CPC ............ *A61K 31/403* (2013.01); *A61K 45/06* (2013.01)

(58) Field of Classification Search
CPC .. A61K 31/403; A61K 45/06; A61K 2300/00; A61P 25/00; A61P 25/28
USPC ........................................................ 514/412
See application file for complete search history.

(56) References Cited

U.S. PATENT DOCUMENTS

| | | |
|---|---|---|
| 3,892,722 A | 7/1975 | Babitsky et al. |
| 4,022,652 A | 5/1977 | Hirano et al. |
| 4,088,652 A | 5/1978 | Fanshawe et al. |
| 4,118,393 A | 10/1978 | Fanshawe et al. |
| 4,118,417 A | 10/1978 | Epstein |
| 4,122,193 A | 10/1978 | Scherm et al. |
| 4,131,611 A | 12/1978 | Fanshawe et al. |
| 4,196,120 A | 4/1980 | Fanshawe et al. |
| 4,231,935 A | 11/1980 | Fanshawe et al. |
| 4,336,268 A | 6/1982 | Bruderer et al. |
| 4,431,661 A | 2/1984 | McKenzie et al. |
| 4,435,419 A | 3/1984 | Epstein et al. |
| 4,467,102 A | 8/1984 | Toda et al. |
| 4,504,657 A | 3/1985 | Bouzard et al. |
| 4,521,431 A | 6/1985 | Crookes |
| 4,591,598 A | 5/1986 | Urbach et al. |
| 5,039,680 A | 8/1991 | Imperato et al. |
| 5,075,341 A | 12/1991 | Mendelson et al. |
| 5,130,430 A | 7/1992 | Shaw |
| 5,198,459 A | 3/1993 | Imperato et al. |
| 5,204,366 A | 4/1993 | Lavanish et al. |
| 5,232,934 A | 8/1993 | Downs |
| 5,488,056 A | 1/1996 | Bodick et al. |
| 5,556,837 A | 9/1996 | Nestler et al. |
| 5,556,838 A | 9/1996 | Mayer et al. |
| 5,574,052 A | 11/1996 | Rose et al. |
| 5,672,360 A | 9/1997 | Sackler et al. |
| 5,762,925 A | 6/1998 | Sagen |
| 5,905,154 A | 5/1999 | Kremer et al. |
| 5,911,992 A | 6/1999 | Braswell et al. |
| 5,916,920 A | 6/1999 | Fernandez et al. |
| 5,969,156 A | 10/1999 | Briggs et al. |
| 5,985,864 A | 11/1999 | Imai et al. |
| 6,109,269 A | 8/2000 | Rise et al. |
| 6,121,261 A | 9/2000 | Glatt et al. |
| 6,132,724 A | 10/2000 | Blum |
| 6,194,000 B1 | 2/2001 | Smith et al. |
| 6,204,284 B1 | 3/2001 | Beer et al. |
| 6,245,357 B1 | 6/2001 | Edgren et al. |
| 6,245,911 B1 | 6/2001 | Imai et al. |
| 6,268,507 B1 | 7/2001 | Massey et al. |
| 6,372,919 B1 | 4/2002 | Lippa et al. |

(Continued)

FOREIGN PATENT DOCUMENTS

| | | |
|---|---|---|
| AU | 2844177 A | 3/1979 |
| AU | 519620 B2 | 12/1981 |

(Continued)

OTHER PUBLICATIONS

"Euthymics Bioscience Increases Series A Financing to Advance Second Program," Business Wire, dated Mar. 9, 2011, 2 pages, retrieved on Mar. 9, 2017, from: http://www.businesswire.com/news/home/20110309005610/en/Euthymics-Bioscience-Increases-Series-Financing-Advance-Program.

(Continued)

*Primary Examiner* — Raymond J Henley, III

(57) ABSTRACT

The present invention relates to (1R,5S)-(+)-1-(naphthalen-2-yl)-3-azabicyclo[3.1.0]hexane and pharmaceutical compositions thereof, and methods employing their use in the treatment of conditions affected by monoamine neurotransmitters, including ADHD and substance abuse.

13 Claims, 8 Drawing Sheets

(56) References Cited

U.S. PATENT DOCUMENTS

| | | |
|---|---|---|
| 6,569,887 B2 | 5/2003 | Lippa et al. |
| 6,716,868 B2 | 4/2004 | Lippa et al. |
| 6,831,175 B2 | 12/2004 | Li et al. |
| 7,041,835 B2 | 5/2006 | Lippa et al. |
| 7,081,471 B2 | 7/2006 | Lippa et al. |
| 7,094,799 B2 | 8/2006 | Russell et al. |
| 7,098,229 B2 | 8/2006 | Lippa et al. |
| 7,098,230 B2 | 8/2006 | Lippa et al. |
| 7,378,419 B2 | 5/2008 | Monneret et al. |
| 8,138,377 B2 | 3/2012 | Skolnick et al. |
| 8,461,196 B2 | 6/2013 | Skolnick et al. |
| 8,877,798 B2 | 11/2014 | Skolnick et al. |
| 9,205,074 B2 | 12/2015 | Skolnick et al. |
| 9,708,261 B2 | 7/2017 | McKinney et al. |
| 9,737,506 B2 | 8/2017 | Skolnick et al. |
| 9,839,627 B2 | 12/2017 | McKinney et al. |
| 9,856,217 B2 | 1/2018 | McKinney et al. |
| 10,039,746 B2 | 8/2018 | Skolnick et al. |
| 10,280,141 B2 | 5/2019 | McKinney et al. |
| 2003/0045567 A1 | 3/2003 | Lippa et al. |
| 2004/0122017 A1 | 6/2004 | Clader et al. |
| 2004/0127541 A1 | 7/2004 | Codd et al. |
| 2005/0096395 A1 | 5/2005 | Rao et al. |
| 2006/0223875 A1 | 10/2006 | Skolnick et al. |
| 2007/0043100 A1 | 2/2007 | Hagen et al. |
| 2007/0082939 A1 | 4/2007 | Lippa et al. |
| 2007/0082940 A1 | 4/2007 | Skolnick et al. |
| 2008/0058535 A1 | 3/2008 | Chen et al. |
| 2008/0269348 A1 | 10/2008 | Skolnick et al. |
| 2008/0293822 A1 | 11/2008 | Skolnick et al. |
| 2009/0041844 A1 | 2/2009 | Friedl et al. |
| 2009/0069374 A1 | 3/2009 | Skolnick et al. |
| 2009/0233978 A1 | 9/2009 | Skolnick et al. |
| 2011/0034565 A1 | 2/2011 | Regan et al. |
| 2012/0258994 A1 | 10/2012 | McKinney et al. |
| 2012/0302619 A1 | 11/2012 | Skolnick et al. |
| 2013/0345439 A1 | 12/2013 | Skolnick et al. |
| 2014/0100249 A1 | 4/2014 | Sears et al. |
| 2014/0206740 A1 | 7/2014 | McKinney et al. |
| 2014/0228421 A1 | 8/2014 | McKinney et al. |
| 2016/0199347 A1 | 7/2016 | McKinney et al. |
| 2016/0303076 A1 | 10/2016 | McKinney et al. |
| 2016/0303077 A1 | 10/2016 | McKinney et al. |
| 2016/0368871 A1 | 12/2016 | McKinney et al. |
| 2017/0334850 A1 | 11/2017 | McKinney et al. |
| 2018/0000777 A1 | 1/2018 | Skolnick et al. |
| 2018/0008575 A1 | 1/2018 | McKinney et al. |
| 2018/0194726 A1 | 7/2018 | McKinney et al. |
| 2018/0215710 A1 | 8/2018 | McKinney et al. |
| 2019/0070148 A1 | 3/2019 | Skolnick et al. |

FOREIGN PATENT DOCUMENTS

| | | | |
|---|---|---|---|
| BE | 858683 | A | 3/1978 |
| BE | 893707 | R | 12/1982 |
| EP | 0100426 | A1 | 2/1984 |
| EP | 1274402 | * | 12/2001 |
| FR | 2 859 208 | A1 | 3/2005 |
| IL | 65843 | A | 12/1986 |
| JP | S53-37656 | A | 4/1978 |
| JP | S58-13568 | A | 1/1983 |
| JP | 2007-523208 | A | 8/2007 |
| JP | 2009-502798 | A | 1/2009 |
| PL | 120 095 | B2 | 2/1982 |
| WO | WO-2003/017927 | A2 | 3/2003 |
| WO | WO-03/047568 | A1 | 6/2003 |
| WO | WO-2003/068211 | A1 | 8/2003 |
| WO | WO-2004/043920 | A1 | 5/2004 |
| WO | WO-2005/080382 | A1 | 9/2005 |
| WO | WO-2006/023659 | A2 | 3/2006 |
| WO | WO-2006/096810 | A2 | 9/2006 |
| WO | WO-2006/108701 | A1 | 10/2006 |
| WO | WO-2006/136223 | A1 | 12/2006 |
| WO | WO-2007/013936 | A2 | 2/2007 |
| WO | WO-2007/014264 | A2 | 2/2007 |
| WO | WO-2007/016155 | A2 | 2/2007 |
| WO | WO-2007/022933 | A1 | 3/2007 |
| WO | WO-2007/022934 | A2 | 3/2007 |
| WO | WO-2007/022935 | A1 | 3/2007 |
| WO | WO-2007/022980 | A1 | 3/2007 |
| WO | WO-2007/025144 | A1 | 3/2007 |
| WO | WO-2007/127421 | A2 | 11/2007 |
| WO | WO-2008/013856 | A2 | 1/2008 |
| WO | WO-2012/118563 | A2 | 9/2012 |
| WO | WO-2013/019271 | A1 | 2/2013 |
| WO | WO-2014/058742 | A1 | 4/2014 |
| WO | WO-2015/089111 | A1 | 6/2015 |
| WO | WO-2015/102826 | A1 | 7/2015 |
| WO | WO-2016/205762 | A1 | 12/2016 |

OTHER PUBLICATIONS

"Euthymics Bioscience Initiates Triade Trial for Major Depression," Business Wire, dated Mar. 14, 2011, 2 pages, retrieved on Mar. 9, 2017, from: http://www.busines swire.com/news/home/20110314005399/en/Euthymics-Bioscience-Initiates-Triade-Trial-Major-Depression.

"Euthymics Bioscience, Inc. Appoints Biotech Industry Veteran Thomas A. Shea as CFO and Announces Additional Senior Management Appointments," Business Wire, dated Jun. 28, 2011, 2 pages, retrieved on Mar. 9, 2017, from: http://www.businesswire.com/news/home/20110628005310/en/Euthymics-Bioscience-Appoints-Biotech-Industry-Veteran-Thomas.

"Euthymics Bioscience, Inc. Appoints Biotech Industry Veteran Walter Piskorski as Vice President, Technical Operations," Business Wire, dated Nov. 18, 2010, 2 pages, retrieved on Mar. 9, 2017, from: http://www.businesswire.com/news/home/20101118005471/en/Euthymics-Bioscience-Appoints-Biotech-Industry-Veteran-Walter.

"Euthymics Bioscience, Inc. Closes $24 Million Series A Financing and Completes Acquisition of DOV Pharmaceutical," Business Wire, dated Jul. 22, 2010, 2 pages, retrieved on Mar. 9, 2017, from: http://www.busines swire.com/news/home/20100722005287/en/Euthymics-Bioscience-Closes-24-Million-Series-Financing.

"Euthymics Bioscience, Inc. Initiates Clinical Trial for New Drug Targeted for Adult Attention Deficit Hyperactivity Disorder (ADHD)," Business Wire, dated Mar. 22, 2012, 2 pages, retrieved on Mar. 28, 2017, from: http://www.businesswire.com/news/home/20120322005110/en/Euthymics-Bioscience-Initiates-Clinical-Trial-Drug-Targeted.

"Euthymics Bioscience, Inc. Names Biotech Executive Timothy J. Barberich to Board of Directors," Business Wire, dated Nov. 4, 2010, 2 pages, retrieved on Mar. 9, 2017, from: http://www.businesswire.com/news/home/20101104005540/en/Euthymics-Bioscience-Names-Biotech-Executive-Timothy-J.

"Euthymics Bioscience, Inc. Presents Data That Support Advancing EB-1020 into Clinical Trials for Adult ADHD," Business Wire, dated Dec. 7, 2011, 2 pages, retrieved on Mar. 28, 2017, from: http://www.businesswire.com/news/home/20111207005128/en/Euthymics-Bioscience-Presents-Data-Support-Advancing-EB-1020.

"Euthymics Bioscience, Inc. Presents Phase II Data for EB-1010 in Major Depression at ACNP Annual Meeting," Business Wire, dated Dec. 8, 2010, 2 pages, retrieved on Mar. 9, 2017, from: http://www.busines swire.com/news/home/20101208005257/en/Euthymics-Bioscience-Pres ents-Phase-II-Data-EB-1010.

"Neurovance Announces Agreement to be Acquired by Otsuka Pharmaceutical," Business Wire, dated Mar. 2, 2017, 2 pages, retrieved on Mar. 21, 2017, from: http://www.businesswire.com/news/home/20170302006210/en/Neurovance-Announces-Agreement-Acquired-Otsuka-Pharmaceutical.

"Neurovance Announces FDA Acceptance of IND Application for EB-1020 SR and Initiates Phase 2a Study in Adult ADHD," Business Wire, dated Sep. 24, 2013, 2 pages, retrieved on Mar. 21, 2017, from: http://www.businesswire.com/news/home/20130924005133/en/Neurovance-Announces-FDA-Acceptance-IND-Application-EB-1020.

"Neurovance Announces Positive Centanafadine Phase 2b Results for Adult ADHD, and Plans for Phase 3 Trials," Business Wire,

(56) References Cited

OTHER PUBLICATIONS dated Jul. 27, 2016, 2 pages, retrieved on Mar. 21, 2017, from: http://www.busines swire.com/news/home/20160727005509/en/Neurovance-Announces -Positive-Centanafadine-Pha se-2b-Results.

"Neurovance Announces Series of Three Clinical Trials to Support Advanced Development of Centanafadine (CTN) in Adult ADHD," Business Wire, dated Jan. 7, 2016, 2 pages, retrieved on Mar. 21, 2017, from: http://www.businesswire.com/news/home/20160107005289/en/Neurovance-Announces-Series-Clinical-Trials-Support-Advanced.

"Neurovance Announces the Appointment of Brian Goff as Chief Operating Officer as the Company Prepares for the Next Stage of Growth and Development," Business Wire, dated Dec. 14, 2016, 3 pages, retrieved on Mar. 21, 2017, from: http://www.busines swire.com/news/home/20161214005389/en/Neurovance-Announces -Appointment-Brian-Goff-Chief-Operating.

"Neurovance Announces Top-Line Study Results Suggest Lower Abuse Potential for Centanafadine Compared to Stimulants for Adult ADHD," Business Wire, dated Dec. 11, 2014, 2 pages, retrieved on Mar. 21, 2017, from: http://www.businesswire.com/news/home/20141211005223/en/Neurovance-Announces-Top-Line-Study-Results-Suggest-Abuse.

"Neurovance Appoints Brigitte Robertson, MD, Vice President, Clinical Development," Business Wire, dated Aug. 5, 2014, 2 pages, retrieved on Mar. 21, 2017, from: http: //www.busines swire.com/news/home/20140805005119/en/Neurovance-Appoints-Brigitte-Robertson-MD-Vice-President.

"Neurovance Appoints Jeff Bailey to Chair Its Board of Directors," Business Wire, dated Jan. 7, 2016, 2 pages, retrieved on Mar. 21, 2017, from: http://www.businesswire.com/news/home/2016010700530 I/en/Neurovance-Appoints-Jeff-Bailey-Chair-Board-Directors.

"Neurovance Closes $6.3M Financing to Support Further Development of EB-1020 SR in Adult ADHD," Business Wire, dated Apr. 3, 2014, 2 pages, retrieved on Mar. 21, 2017, from: http: //www.busines swire.com/news/home/20140403005159/en/Neurovance-Clos es -6. 3M-Financing-Support-Development-EB-1020.

"Neurovance Closes $7M Series AI Round for Development of EB-1020 for ADHD; Reports Phase 1 Clinical Trial Results," Business Wire, dated Oct. 18, 2012, 2 pages, retrieved on Mar. 21, 2017, from: http://www.businesswire.com/news/home/20121018005122/en/Neurovance-Closes-7M-Series-AI-Development-EB-1020.

"Neurovance Completes Enrollment in Human Abuse Liability Study for Centanafadine (Formerly Called EB-1020) for Adult ADHD," Business Wire, dated Aug. 7, 2014, 2 pages, retrieved on Mar. 21, 2017, from: http://www.businesswire.com/news/home/20140807005111/en/Neurovance-Completes-Enrollment-Human-Abuse-Liability-Study.

"Neurovance Receives Notice of Allowance for Composition of Matter Patent and Initiates Clinical Trial of New SR Formulation of EB-1020," Business Wire, dated Feb. 21, 2013, 2 pages, retrieved on Mar. 21, 2017, from: http://www.businesswire.com/news/home/20130221005219/en/Neurovance-Receives-Notice-Allowance-Composition-Matter-Patent.

"Neurovance Says Interim Data from Phase 2a Pilot Study of EB-1020 SR Shows Stimulant-Like Efficacy, but with Lower Risk of Abuse, for Adult ADHD," Business Wire, dated Jan. 9, 2014, 2 pages, retrieved on Mar. 21, 2017, from: http://www.businesswire.com/news/home/20140109005346/en/Neurovance-Interim-Data-Phase-2a-Pilot-Study.

"Neurovance's EB-1020 SR for Adult ADHD Shows Stimulant-Like Efficacy and Good Tolerability in Phase 2a Trial," Business Wire, dated May 8, 2014, 2 pages, retrieved on Mar. 21, 2017, from: http://www.busines swire.com/news/home/20140508005244/en/Neurovance%E 2%80%99s-EB- 1020-SR-Adult-ADHD-Shows-Stimulant-Like.

"Neurovance's Lead Product Granted Non-Proprietary Name; EB-1020 SR Now Called Centanafadine SR," Evaluate Group, dated Jun. 11, 2014, 1 page, retrieved on Mar. 21, 2017, from: http://www.evaluategroup.com/Universal/View.aspx?type=Story&id=523365.

"Otsuka Pharmaceutical to Acquire Neurovance, Inc.," dated Mar. 2, 2017, 3 pages, retrieved on Mar. 21, 2017, from: http://www.businesswire.com/news/home/20170302005888/en/Otsuka-Pharmaceutical-Acquire-Neurovance.

"Pain Therapeutics Takes Different Path, Improving Long-term Pain Relief by Reducing Dependency and Tolerance," retrieved from http://www.genengnews.com/biobusiness/cpitem.aspx?aid=1706 on Sep. 19, 2007, 2 pages, document states:Genetic Engineering and Biotechnology News, 2006, 26 (12).

"Theravance Announces Initiation of Phase 2 Study With Its Marin Compound, TD-9855, for the Treatment of ADHD," Theravance Press Release, 2 pages, dated 2011, [retrieved on Feb. 17, 2015]. Retrieved from the Internet: <URL: http://www.marketwired.com/press-release/theravance-announces-initiation-phase-2-study-withits-marin-compound-td-9855-treatment-nasdaq-thrx-1597199.htm>.

Adler, L. et al., "Lisdexamfetamine Dimesylate in Adults with Attention-Deficit/Hyperactivity Disorder Who Report Clinically Significant Impairment in Executive Function: Results from a Randomized, Double-Blind, Placebo-Controlled Study," Journal of Clinical Psychiatry, 2013, 74 (7), 694702.

Adler, L. et al., "Once-Daily Atomoxetine for Adult Attention-Deficit/Hyperactivity Disorder: A 6-Month Double-Blind Trial," Journal of Clinical Psychopharmacology, 2009, 29, 44-50.

Amendment After Allowance filed Oct. 19, 2015, in U.S. Appl. No. 14/494,512, 6 pages.

Arfken, C. et al., "Postmarketing Surveillance of Abuse Liability of Sibutramine," Drug and Alcohol Dependence, 2003, 69, 169-173.

Armarego, W. et al., "Quinazolines. Part XVIII. A Second Stereospecific cis-Addition of the Elements of Nitromethane across a Tetrasubstituted Ethylenic Double Bond. A Concerted Mechanism for the Reaction of Nitroacetic Acid with Enamines," Journal of the Chemical Society (C), 1971, 19, 3222-3229.

Arnsten, A., "The Emerging Neurobiology of Attention Deficit Hyperactivity Disorder: The Key Role of the Prefrontal Association Cortex," NIH Public Access, Author Manuscript, available in PMC Jun. 3, 20100, 20 pages, face of article states: *J Pediatr.* May 1, 2009; 154(5): I-S43, doi: 10.1016/j.jpeds.2009.01.018.

Bailey, D. et al., "Medication Utilization for Targeted Symptoms in Children and Adults With Fragile X Syndrome: US Survey," Journal of Developmental & Behavioral Pediatrics, 2012, 33 (1), 62-69.

Baldessarini, R., "Drugs and the Treatment of Psychiatric Disorders" in Goodman and Gilman's The Pharmacological Basis of Therapeutics, Ninth Edition, J.G. Hardman et al., Eds., McGraw-Hill, New York, 1996, Chapter 17, p. 399, and Chapter 18, pp. 431-459.

Barkley, R. et al., "Young Adult Outcome of Hyperactive Children: Adaptive Functioning in Major Life Activities," Journal of the American Academy of Child and Adolescent Psychiatry, 2006, 45 (2), 192-202.

Bayes, M. et al., "Gateways to Clinical Trials," Methods and Findings in Experimental and Clinical Pharmacology, 2003, 25 (3), 225-248.

Beer, B. et al., "DOV 216,303, A 'Triple' Reuptake Inhibitor: Safety, Tolerability, and Pharmacokinetic Profile," The Journal of Clinical Pharmacology, 2004, 44 (12), 1360-1367.

Berman, S. et al., "Potential Adverse Effects of Amphetamine Treatment on Brain and Behavior: A Review," Molecular Psychiatry, 2009, 14, 123-42.

Berry-Kravis, E. et al., "Clinic-Based Retrospective Analysis of Psychopharmacology for Behavior in Fragile X Syndrome," International Journal of Pediatrics, 2012, Article ID 843016, 11 pages, doi:10.1155/2012/843016.

Biederman, J. et al., "A Randomized, Placebo-Controlled Trial of OROS Methylphenidate in Adults with Attention-Deficit/Hyperactivity Disorder," Biological Psychiatry, 2006, 59, 829-835.

Biederman, J. et al., "Comparison of Parent and Teacher Reports of Attention-Deficit/Hyperactivity Disorder Symptoms from Two Placebo-Controlled Studies of Atomoxetine in Children," Biological Psychiatry, 2006, 60, 1106-1110.

(56) References Cited

OTHER PUBLICATIONS

Biederman, J. et al., "Functional Impairments in Adults with Self-Reports of Diagnosed ADHD: A Controlled Study of 1001 Adults in the Community," Journal of Clinical Psychiatry, 2006, 67 (4), 524540.

Biederman, J. et al., "The Effects of Attention-Deficit/Hyperactivity Disorder on Employment and Household Income," Medscape General Medicine, 16 pages, retrieved on Mar. 23, 2017, from: http://www.ncbi.nlm.nih.gov/pmc/articles/PMC1781280/?report=printable, face of article states: MedGenMed. 2006; 8(3): 12; published online Jul. 19, 2006.

Biederman, J., et al., "Attention-Deficit/Hyperactivity Disorder (ADHD) as a Noradrenergic Disorder," Biological Psychiatry, 1999, 46, 1234-1242.

Blum, K. et al., "Dopamine D2 Receptor Gene Variants: Association and Linkage Studies in Impulsive-Addictive-Compulsive Behaviour," Pharmacogenetics, 1995, 5 (3), 121-141.

Bray, G., "A Concise Review on the Therapeutics of Obesity," Nutrition, 2000, 16 (10), 953-960.

Brown, T. et al., "Open-Label Administration of Lisdexamfetamine Dimestylate Improves Executive Function Impairments and Symptoms of Attention-Deficit/Hyperactivity Disorder in Adults," Postgraduate Medicine, 2010, 122 (5), 7-17.

Buitelaar, J. et al., "Treating Attention-Deficit/Hyperactivity Disorder Beyond Symptom Control Alone in Children and Adolescents: A Review of the Potential Benefits of Long-Acting Stimulants," European Child and Adolescent Psychiatry, 2010, 19 (4), 325-340.

Busner, J. et al., "A Novel Computer-Prompted Tandem Rating Assessment for Adult ADHD Clinical Trials," ASCP Annual Meeting 2014, Abstract Book—Posters, 165 pages, Poster Session 2, Abstract 1, pp. 87-88, retrieved on Mar. 23, 2017, from: http://ascpmeeting.org/wp-content/uploads/2014/06/Poster-Abstracts-FINAL.pdf.

Busner, J. et al., "A Novel Computer-Prompted Tandem Rating Assessment for Adult ADHD Clinical Trials," Poster, ASCP Annual Meeting 2014, 1 page.

Bymaster, F. et al., "Atomoxetine Increases Extracellular Levels of Norepinephrine and Dopamine in Prefrontal Cortex of Rat: A Potential Mechanism for Efficacy in Attention Deficit/Hyperactivity Disorder," Neuropsychopharmacology, 2002, 27, 699-711.

Bymaster, F. et al., "Pharmacological Characterization of the Monoamine Uptake Inhibitor EB-1020: A Drug Candidate for Adult ADHD," Poster, Neuroscience 2011 Meeting, 1 page.

Bymaster, F. et al., "Pharmacological Characterization of the Monoamine Uptake Inhibitor EB-1020: A Drug Candidate for Adult ADHD," Presentation Abstract for Neuroscience 2011 Meeting, 4 pages, retrieved on Mar. 21, 2017, from: http://www.abstractsonline.com/Plan/ViewAbstract.aspx?mID=2773&sKey=5e8c291d-2b5d-44b0-8baa-5c2ff721da2b&cKey=69c974ee-14ae-41b4-b157-99aedb24eclf4&mKey=8334be29-8911-4991-8c31-32b32dd5e6c8.

Bymaster, F. et al., "Pharmacological Characterization of the Norepinephrine and Dopamine Reuptake Inhibitor EB-1020: Implications for Treatment of Attention-Deficit Hyperactivity Disorder," Synapse, 2012, 66, 522-532.

Byrn, S. et al., Chapter 11 entitled "Hydrates and Solvates," pp. 233-247, in Solid-State Chemistry of Drugs, Second Edition, SSCI, Inc. Indiana, 1999.

Caira, M., "Crystalline Polymorphism of Organic Compounds," Topics in Current Chemistry, 1998, 198, 163-208 (Abstract only).

Casadio, S. et al., "Acide Phenyl-I-Hydroxymethyl-2-Cyclopropane Carboxylique Et Derives," Bollettino Chimico Farmaceutico, 1978, 117, 331-342.

Cleveland Clinic, "Attention Deficit Hyperactivity Disorder (ADHD): Nonstimulant Therapy (Strattera) & Other ADHD Drugs," dated 2017, 9 pages, [retrieved on May 8, 2018]. Retrieved from the Internet <URL: https://my.clevelandclinic.org/health/drugs/12959-attention-deficit-hyperactivity-disorder-adhd-nonstimulant-therapy-strattera-other-adhd-drugs?view=print>.

Cole, J. et al., "Sibutramine: A New Weight Loss Agent without Evidence of the Abuse Potential Associated with Amphetamines," 7 pages, face of article states: Journal of Clinical Psychopharmacology: Jun. 1998—vol. 18—Issue 3—pp. 231-236, retrieved on Mar. 24, 2017, from http://journals.1ww.com/psychopharmacology/pages/articleviewer.aspx?year=1998&issue=06000&article=00008&type=Fulltext.

Consensus of the Fragile X Clinical & Research Consortium on Clinical Practices, "Medications for Individuals with Fragile X Syndrome," dated 2012, 10 pages, [retrieved on May 8, 2017]. Retrieved from the Internet <URL: https://fragilex.org/wp-content/uploads/2012/08/Medicationsfor_Individuals_with_Fragile_X_Syndrome2012-Oct.pdf>.

Crown, W., "Economic Outcomes Associated with Tricyclic Antidepressant and Selective Serotonin Reuptake Inhibitor Treatments for Depression," Acta Psychiatrica Scandinavica Supplementum, 2000, 403, 62-66.

Czobor, P., "A Double-Blind, Placebo Controlled Randomized Study of DOV 220,075 (Bicifadine) SR and Codeine 60 mg in the Treatment of Post-Operative Dental Pain," American Pain Society 2003, Abstract (915).

Czobor, P., "A Two Center Double-Blind Placebo-Controlled Randomized Study of DOV 220,075 (Bicifadine) SR and Tramadol 100 mg in the Treatment of Post-Operative Dental Pain," American Pain Society, 2004, Abstract (801).

D'aquila, P. et al., "The Role of Dopamine in the Mechanism of Action of Antidepressant Drugs," European Journal of Pharmacology, 2000, 405 (1-3), 365-373.

Davis, P. et al., "Inhibitors of Protein Kinase C. 1. 2,3-Bisarylmaleimides," Journal of Medicinal Chemistry, 1992, 35 (1), 177-184.

Dulcan, M. et al., "Practice Parameters for the Assessment and Treatment of Children, Adolescents, and Adults with Attention-Deficit/Hyperactivity Disorder," Journal of the American Academy of Child and Adolescent Psychiatry, 1997, 36 (10 Supplement), 85S-121S.

Elkashef, A. et al., "Bupropion for the Treatment of Methamphetamine Dependence," Neuropsychopharmacology, 2008, 33 (5), 1162-1170.

Epstein, J. et al., "1-Aryl-3-azabicyclo[3.1.0]hexanes, a New Series of Nonnarcotic Analgesic Agents," Journal of Medicinal Chemistry, 1981, 24 (5), 481-490.

Epstein, J. et al., "Bicifadine: Non-Narcotic Analgesic Activity of 1-Aryl-3-Azabicycl[3.1.0]Hexanes," NIDA Research Monograph, 1982, 41, 93-98.

Ettmayer, P. et al., "Lessons Learned from Marketed and Investigational Prodrugs," Journal of Medicinal Chemistry, 2004, 47 (10), 2393-2404.

Faraone, S. et al., "What Is the Prevalence of Adult ADHD? Results of a Population Screen of 966 Adults," Journal of Attention Disorders, 2005, 9 (2), 384-391.

Fauci, A. et al., Eds., Harrison's Principles of Internal Medicine, Fourteenth Edition, McGraw-Hill, New York, 1998, pp. 2485-2503.

Frazer, A., "Norepinephrine Involvement in Antidepressant Action," Journal of Clinical Psychiatry, 2000, 61 (Suppl. 10), 25-30.

Fredman, S. et al., "Partial Response, Nonresponse, and Relapse with Selective Serotonin Reuptake Inhibitors in Major Depression: A Survey of Current 'Next-Step' Practices," Journal of Clinical Psychiatry, 2000, 61 (6), 403-408.

Gallagher, A. et al., "Fragile X-associated Disorders: A Clinical Overview," Journal of Neurology, 2012, 259, 401-413.

Grant, J., Ed., Hackh's Chemical Dictionary, Fourth Edition, McGraw-Hill Book Company, New York, 1969, pp. 474-475.

Greenhill, L. et al., "Practice Parameter for the Use of Stimulant Medications in the Treatment of Children, Adolescents, and Adults," Journal of the American Academy of Child and Adolescent Psychiatry, 2002, 41 (2 Supplement), 26S-49S.

Hammerness, P. et al., "An Open Study of Adjunct OROS-Methylphenidate in Children Who are Atomoxetine Partial Responders: II. Tolerability and Pharmacokinetics," Journal of Child and Adolescent Psychopharmacology, 2009, 19 (5), 493-499.

Han, D. et al., "Comparison of the Monoamine Transporters from Human and Mouse in Their Sensitivities to Psychostimulant Drugs," BMC Pharmacology, 2006, 6 (6), 7 pages, doi:10.1186/1471-2210-6-6.

(56) References Cited

OTHER PUBLICATIONS

Hartley, S. et al., "Exploring the Adult Life of Men and Women with Fragile X Syndrome: Results from a National Survey," NIH Public Access, Author Manuscript, available in PMC Dec. 15, 2011, face of article states: Published in final edited form as: *Am J Intellect Dev Disabil* Jan. 2011; 116(1): 16-35, doi:10.1352/1944-7558-116.1.16, 24 pages.

Hays, J. et al., "Bupropion Sustained Release for Treatment of Tobacco Dependence," Mayo Clinic Proceedings, 2003, 78 (8), 1020-1024.

Hitri, A. et al., "Molecular, Functional and Biochemical Characteristics of the Dopamine Transporter: Regional Differences and Clinical Relevance," Clinical Neuropharmacology, 1994, 17 (1), 1-22.

Hoffman, B. et al., "Localization and Dynamic Regulation of Biogenic Amine Transporters in the Mammalian Central Nervous System," Frontiers in Neuroendocrinology, 1998, 19 (3), 187-231.

Hsu, T. e al., "A Pilot Study of a Novel Monoamine Triple Reuptake Inhibitor, Centanafadine (EB-1020) SR, In the Treatment of Attention Deficit Hyperactivity Disorder in Adult Males," poster presented at Annual Meeting of the American College of Neuropsychopharmacology, 2014, 1 page.

Hsu, T. et al., "A Pilot Study of a Novel Monoamine Triple Reuptake Inhibitor Centanafadine SR (EB-1020 SR) in the Treatment of ADHD in Adults," Neuropsychopharmacology, 2014, 39, S291-S472, abstracts for ACNP 53rd Annual Meeting, Abstract T94, p. 5352.

International Preliminary Report on Patentability for International Application No. PCT/US2006/029006, dated Jan. 29, 2008, 5 pages.

International Preliminary Report on Patentability for International Application No. PCT/US2014/069401, dated Jun. 14, 2016, 16 pages.

International Preliminary Report on Patentability for International Application No. PCT/US2014/069416, dated Jun. 14, 2016, 5 pages.

International Preliminary Report on Patentability for International Application No. PCT/US2016/038256, dated Dec. 19, 2017, 5 pages.

International Preliminary Report on Patentability, dated Feb. 4, 2014, for International Application No. PCT/US2012/00335, 5 pages.

International Search Report for International Application No. PCT/US2014/069401, dated Mar. 18, 2015, 3 pages.

International Search Report for International Application No. PCT/US2014/069416, dated Feb. 26, 2015, 4 pages.

International Search Report for International Application No. PCT/US2016/038256, dated Sep. 13, 2016, 3 pages.

International Search Report dated Oct. 16, 2012, for International Application No. PCT/US2012/00335, 2 pages.

International Search Report dated Sep. 24, 2007, for International Application No. PCT/US2006/029006, 2 pages.

Janowsky, A. et al., "Characterization of Sodium-Dependent PH1GBR-12935 Binding in Brain: A Radioligand for Selective Labelling of the Dopamine Transport Complex," Journal of Neurochemistry, 1986, 46 (4), 1272-1276.

Jasinski, D. et al., "Abuse Liability Assessment of Atomoxetine in a Drug-Abusing Population," Drug and Alcohol Dependence, 2008, 95, 140-146.

Kessler, R., et al., "The Prevalence and Correlates of Adult ADHD in the United States: Results from the National Comorbidity Survey Replication," American Journal of Psychiatry, 2006, 163 (4), 716-723.

Kiyatkin, E., "Dopamine Mechanisms of Cocaine Addiction," The International Journal of Neuroscience, 1994, 78 (1-2), 75-101.

Kozma, D. et al., "Optical Resolution in Two Immiscible Solvents in the Presence of an Intermediate Solvent. Optical Resolution of N-methyl-amphetamine by 0,0'-Dibenzoyl-R,R-tartartic Acid in Dichloroethane-Water-Methanol Solvent System," Synthetic Communications, 1999, 29 (24), 4315-4319.

Kreek, M., "Cocaine, Dopamine and the Endogenous Opioid System," Journal of Addictive Diseases, 1996, 15 (14), 73-96.

Leonhardt, M. et al., "New Approaches in the Pharmacological Treatment of Obesity," European Journal of Nutrition, 1999, 38 (1), 1-13.

Levin, F. et al., "Attention-Deficit Hyperactivity Disorder and Substance Abuse: Relationships and Implications for Treatment," Harvard Review of Psychiatry, 1995, 2, 246-258.

Levin, F. et al., "Attention-Deficit Hyperactivity Disorder and Substance Abuse: Relationships and Implications for Treatment," The Harvard Review of Psychiatry, 1995, 2 (5), 246-258 (abstract only).

Lima, L. et al., "Bioisosterism: A Useful Strategy for Molecular Modification and Drug Design," Current Medicinal Chemistry, 2005, 12 (1), 23-49.

Marrazzo, A. et al., "1-Phenyl-3-azabicyclo[3.1.0]hexane Derivatives as New Ligands for Sigma Receptors," Arkivoc, 2004, 5, 156-169.

McArdle, P. et al., "A Method for the Prediction of the Crystal Structure of Ionic Organic Compounds—The Crystal Structures of 0-Toluidinium Chloride and Bromide and Polymorphism of Bicifadine Hydrochloride," CrystEngComm, 2004, 6 (53), 303-309.

McBriar, M. et al., "Discovery of Bicycloalkyl Urea Melanin Concentrating Hormone Receptor Antagonists: Orally Efficacious Antiobesity Therapeutics," Journal of Medicinal Chemistry, 2005, 48 (7), 2274-2277.

McBriar, M. et al., "Discovery of Orally Efficacious Melanin-Concentrating Hormone Receptor01 Antagonists as Antiobesity Agents. Synthesis, SAR, and Biological Evaluation of Bicyclo[3.1.0]hexyl Ureas," Journal of Medicinal Chemistry, 2006, 49 (7), 2294-2310.

McMillen, B. et al., "Effect of DOV 102,677 on the Volitional Consumption of Ethanol by Myers' High Ethanol-Preferring Rat," Alcoholism, Clinical and Experimental Research, 2007, 31 (11), 1866-1871.

Meyerson, L. et al., "Allosteric Interaction Between the Site Labeled by PFIllmipramine and the Serotonin Transporter in Human Platelets," Journal of Neurochemistry, 1987, 48 (2), 560-565.

Micheli, F. et al., "1-(Aryl)-6-[alkoxyalky1]-3-azabicyclo[3.1.0]hexanes and 6-(Ary1)-6-[alkoxyalky1]-3-azabicyclo[3.1.0]hexanes: A New Series of Potent and Selective Triple Reuptake Inhibitors," Journal of Medicinal Chemistry, 2010, 53 (6), 2534-2551.

Mirani, A. et al., "Direct Compression High Functionality Excipient Using Coprocessing Technique: A Brief Review," Current Drug Delivery, 2011, 8, 426-435.

Morissette, S. et al., "High-Throughput Crystallization: Polymorphs, Salts, Co-Crystals and Solvates of Pharmaceutical Solids," Advanced Drug Delivery Reviews, 2004, 56 (3), 275-300.

Mouzin, G. et al., "A Convenient Synthesis of Bifunctional Vicinal Cyclopropanes," Synthesis, 1978, 4, 304-305.

Nagatsu, T. et al., "Changes in Cytokines and Neurotrophins in Parkinson's Disease," Journal of Neural Transmission. Supplementa, 2000, 60, 277-290.

Neurovance, "EB-1020 SR, a Non-Stimulant Norepinephrine and Dopamine-Preferring Reuptake Inhibitor for the Treatment of Adult ADHD," 2014, 2 pages, retrieved on Oct. 26, 2017, from: http://euthymics.com/wp-content/uploads/2014/0 1/EB-1020-SR-White-Paper-010314.pclf.

Neurovance, "EB-1020, a Non-Stimulant Norepinephrine and Dopamine-Preferring Reuptake Inhibitor for the Treatment of Adult ADHD," 2012, 2 pages, retrieved on Oct. 26, 2017, from: http://euthymics.com/wp-content/uploads/2012/10/White-Paper-EB1020-092612.pdf.

Newcorn, J. et al., "Atomoxetine and Osmotically Released Methylphenidate for the Treatment of Attention Deficit Hyperactivity Disorder: Acute Comparison and Differential Response," American Journal of Psychiatry, 2008, 165 (6), 721-730.

Noble, E., "Polymorphisms of the D2 Dopamine Receptor Gene and Alcoholism and Other Substance Use Disorders," Alcohol and Alcoholism—Supplements, 1994, 2, 35-43.

Non-Final Office Action dated Apr. 17, 2019, in U.S. Appl. No. 16/028,257, 23 pages.

(56) References Cited

OTHER PUBLICATIONS

Non-Final Office Action dated Sep. 29, 2016, in U.S. Appl. No. 14/929,361, 15 pages.
Notice of Allowability dated Nov. 4, 2015, in U.S. Appl. No. 14/494,512, 5 pages.
Notice of Allowance and Fee(s) Due dated Apr. 13, 2017, in U.S. Appl. No. 14/929,361, 8 pages.
Notice of Allowance and Fee(s) Due dated Apr. 3, 2018, in U.S. Appl. No. 15/648,424, 15 pages.
Notice of Allowance and Fee(s) Due issued in U.S. Appl. No. 14/494,512 dated Mar. 31, 2015, 13 pages.
Notice of Allowance and Fee(s) Due dated Jul. 17, 2015, in U.S. Appl. No. 14/494,512, 8 pages.
Ohlmeier, M. et al., "Comorbidity of Alcohol and Substance Dependence with Attention-Deficit/Hyperactivity Disorder (ADHD)," Alcohol & Alcoholism, 2008, 43 (3), 300-304.
Perovic, S. et al., "Pharmacological Profile of Hypericum Extract, Effect on Serotonin Uptake by Postsynaptic Receptors," Arzneimittel Forschung / Drug Research, 1995, 45 (II), 11, 1145-1148.
PharmTech.com, "RetaLac0, a New Excipient for Direct Compression of Sustained Release Formulations," dated Jul. 9, 2010, 3 pages.
Polanczyk, G. et al., "The Worldwide Prevalence of ADHD: A Systematic Review and Metaregression Analysis," American Journal of Psychiatry, 2007, 164 (6), 942-948.
Popik, P., et al., "Pharmacological Profile of the 'Triple' Monoamine Neurotransmitter Uptake Inhibitor, DOV 102,677," Cellular and Molecular Neurobiology, 2006, 26 (4-6), 857-873.
Porter, E., "Single Dose Comparison of Bicifadine, Codeine, and Placebo in Postoperative Pain," Current Therapeutic Research, 1981, 30 (3), 156-160.
Preliminary Amendment and Response to Notice to File Missing Parts of Nonprovisional Application filed Nov. 25, 2018, in U.S. Appl. No. 16/028,257, 6 pages.
Preliminary Amendment and Response to Notice to File Missing Parts of Nonprovisional Application filed Sep. 25, 2017, in U.S. Appl. No. 15/648,424, 8 pages.
Reply to Office Action filed Mar. 29, 2017, in U.S. Appl. No. 14/929,361, 9 pages.
Response to Notice to File Missing Parts of Nonprovisional Application filed Feb. 17, 2016, in U.S. Appl. No. 14/929,361, 7 pages.
Response to Notice to File Missing Parts of Nonprovisional Application filed Feb. 2, 2015, in U.S. Appl. No. 14/494,512, 5 pages.
Response to Rule 312 Communication dated Oct. 27, 2015, in U.S. Appl. No. 14/494,512, 6 pages.
Robertson, B. et al., "Early Stage Assessment of the Abuse Potential of Centanafadine, a Triple Reuptake Inhibitor: Preclinical and Clinical Study Results," Neuropsychopharmacology, 2014, 39, S473-S647, abstracts for ACNP 53rd Annual Meeting, Abstract W160, pp. S575-S576.
Robertson, B. et al., "Early Stage Assessment of the Abuse Potential of Centanafadine, a Triple Reuptake Inhibitor: Preclinical and Clinical Study Results," poster presented at Annual Meeting of the American College of Neuropsychopharmacology, 2014, 1 page.
Romach, M. et al., "Human Abuse Liability Evaluation of CNS Stimulant Drugs," Neuopharmacology, 2014, 87, 81-90.
Rondestvedt, C. et al., "Arylation of Unsaturated Systems by Free Radicals. VII. The Meerwein Reaction. V. Further Arylations of Maleimides. Ultraviolet Spectra of Arylmaleimides, Arylmaleic Anhydrides and Arylmaleo- and Fumaronitriles," Journal of the American Chemical Society, 1956, 78, 6115-6120.
Rouhi, A., "The Right Stuff, From Research and Development to the Clinic, Getting Drug Crystals Right is Full of Pitfalls," retrieved from http://pubs.acs.org/isubscribe/journals/cen/81/108/print/8108scil.html on Feb. 2, 2007, 11 pages, document states: Chemical and Engineering News, 2003, 81 (8), 32-35.
Rowe, R. Ed., "Handbook of Pharmaceutical Excipients," Fourth Edition, Royal Pharmaceutical Society of Great Britain, London, UK, 2003, "Hypromellose," pp. 297-300.
Rueda, J-R. et al., "Systematic Review of Pharmacological Treatments in Fragile X Syndrome," BMC Neurology, 2009, 9, 53, 11 pages, doi: 10.1186/1471-2377-9-53.
Sanchez, C. et al., "Comparison of the Effects of Antidepressants and Their Metabolites on Reuptake of Biogenic Amines and on Receptor Binding," Cellular and Molecular Neurobiology, 1999, 19 (4), 467-489.
Scahill, L. et al., "Epidemiology of ADHD in School-Age Children," Child and Adolescent Psychiatric Clinics of North America, 2000, 9 (3), 541-555 (abstract only).
Scates, A. et al., "Reboxetine: A Selective Norepinephrine Reuptake Inhibitor for the Treatment of Depression," The Annals of Pharmacotherapy, 2000, 34 (11), 1302-1312.
Shram, M. et al., "An Exploratory Human Abuse Potential Assessment of Centanafadine, a Novel Triple Reuptake Inhibitor," Abstract, Drug and Alcohol Dependence, 2015, 156, e203-e204, abstract from 2015 Annual Meeting of the College on Problems of Drug Dependence.
Shram, M. et al., "Exploratory Human Abuse Potential Assessment of Centanafadine, a Novel Triple Reuptake Inhibitor," Clinical Pharmacology & Therapeutics, 2015, 97 (Supplement 1), S60-S96, abstracts for ASCPT 2015 Annual Meeting, Abstract PII-011, pp. S62-S63.
Shram, M. et al., "Exploratory Human Abuse Potential Assessment of Centanafadine, a Novel Triple Reuptake Inhibitor," retrieved on Apr. 23, 2019, from https://www.vinceandassociates.com/sites/default/files/Neurovance-HAL-poster_2015_03_04-final.pdf, 1 page.
Shuto, S. et al., "Synthesis of (+)- and (−)-Milnaciprans and Their Conformationally Restricted Analogs," Tetrahedron Letters, 1996, 37 (5), 641-644.
Simon, G. et al., "TCAs or SSRIs As Initial Therapy for Depression," The Journal of Family Practice, 1999, 48, 845-846.
Skolnick, P. et al., "'Broad Spectrum' Antidepressants: Is More Better for the Treatment of Depression," Life Sciences, 2003, 73 (25), 3175-3179.
Skolnick, P. et al., "Antidepressant-like Actions of DOV 21,947, A 'Triple' Reuptake Inhibitor," European Journal of Pharmacology, 2003, 461, 99-104.
Skolnick, P., "Beyond Monoamine-Based Therapies: Clues to New Approaches," Journal of Clinical Psychiatry, 2002, 63 (Suppl. 2), 19-23.
Smith, R. et al., "Comparative Effects of d-Amphetamine, /-Amphetamine, and Methylphenidate on Mood in Man," Psychopharmacology, 1977, 53 (1), 1-12.
Spencer, T. et al., "A Large, Double-Blind, Randomized Clinical Trial of Methylphenidate in the Treatment of Adults with Attention-Deficit/Hyperactivity Disorders," Biological Psychiatry, 2005, 57 (5), 456-463.
Spencer, T. et al., "Attention-Deficit/Hyperactivity Disorder: Diagnosis, Lifespan, Comorbidities, and Neurobiology," Journal of Pediatric Psychology, 2007, 32 (6), 631-642.
Spencer, T. et al., "Effectiveness and Tolerability of Tomoxetine in Adults with Attention Deficit Hyperactivity Disorder," American Journal of Psychiatry, 1998, 155 (5), 693-695.
Stacy, M. et al., "Treatment Options for Early Parkinson's Disease," American Family Physician, 1996, 53 (4), 1281-1287.
Stella, V., "Prodrugs as Therapeutics," Expert Opinion on Therapeutic Patents, 2004, 14 (3), 277-280.
Sullivan, A. et al., "Mechanisms of Appetite Modulation by Drugs," Federation Proceedings, 1985, 44 (1 Pt. 1), 139-144.
Surman, C. et al., "Atomoxetine in the Treatment of Adults with Subthreshold and/or Late Onset Attention-Deficit Hyperactivity Disorder—Not Otherwise Specified (ADHD-NOS): A Prospective Open-Label 6-Week Study," CNS Neuroscience & Therapeutics, 2010, 16, 6-12.
Tarazi, F. et al., "Pharmacological and Behavioral Characterization of the Norepinephrine and Dopamine Reuptake Inhibitor EB-1020: A Novel Pharmacotherapy for ADHD," Neuropsychopharmacology, 2011, 36, S198-S323, abstracts for ACNP 50th Annual Meeting, Abstract 205, p. 5310.

(56) References Cited

OTHER PUBLICATIONS

Tarazi, F. et al., "Pharmacological and Behavioral Characterization of the Norepinephrine and Dopamine Reuptake Inhibitor EB-1020: A Novel Pharmacotherapy for ADHD," Poster, 2011, ACNP 50th Annual Meeting, 1 page.
Taylor, A. et al., "Scales for the Identification of Adults with Attention Deficit Hyperactivity Disorder (ADHD): A Systematic Review," Research in Developmental Disabilities, 2011, 32 (3), 924-938.
Testa, B., "Prodrug Research: Futile or Fertile," Biochemical Pharmacology, 2004, 68 (11), 2097-2106.
Theeuwes, F., "Drug Delivery Fuels Specialty Pharma, Rich Source of Innovation Now Significant Platform to Launch New Companies," retrieved from http://www.genengnews.com/articles/chitem.aspx?aid=2107 Sep. 19, 2007, 2 pages, document states: Genetic Engineering and Biotechnology News, 2007, 27 (10-100).
Tominaga, Y. et al., "Synthesis of Methylthiomaleimides for the Preparation of Pyridazines and Related Compounds," Journal of Heterocyclic Chemistry, 2002, 39 (3), 571-591.
U.S. Appl. No. 13/605,890, filed Sep. 6, 2012, McKinney.
U.S. Appl. No. 60/661,662, filed Mar. 8, 2005, Skolnick et al.
U.S. Appl. No. 60/701,562, filed Jul. 22, 2005, Skolnick et al.
U.S. Appl. No. 60/702,800, filed Jul. 26, 2005, Lippa et al.
U.S. Appl. No. 60/833,438, filed Jul. 25, 2006, Skolnick et al.
U.S. Appl. No. 61/573,499, filed Sep. 7, 2011, McKinney et al.
Vilsmaier, E. et al., "Functionalized Chloroenamines in Aminocyclopropane Synthesis III. Synthesis and Assignment of Configuration of Two Isomeric Morpholinobicyclo[3.1.0]hexane Derivatives," Tetrahedron, 1989, 45 (12), 3683-3694.
Vippagunta, S. et al., "Crystalline Solids," Advanced Drug Delivery Reviews, 2001, 48 (1), 3-26.
Wang, R. et al., "The Oral Analgesic Efficacy of Bicifadine Hydrochloride in Postoperative Pain," The Journal of Clinical Pharmacology, 1982, 22 (4), 160-164.
Wilens, T. et al., "Bupropion XL in Adults with Attention-Deficit/Hyperactivity Disorder: A Randomized Placebo-Controlled Study," Biological Psychiatry, 2005, 57, 793-801.
Wilens, T. et al., "An Open Study of Adjunct OROS-Methylphenidate in Children and Adolescents Who are Atomoxetine Partial Responders: I. Effectiveness," Journal of Child and Adolescent Psychopharmacology, 2009, 19 (5), 485-492.
Wilens, T. et al., "A Pilot Study of a Novel Monoamine Triple Reuptake Inhibitor EB-1020 SR In the Treatment of ADHD in Adults," ASCP Annual Meeting 2014, Abstract Book—Oral Sessions, 107 pages, Individual Abstract, pp. 33-34, retrieved on Mar. 27, 2017, from: http://ascpmeeting.org/wp-content/uploads/2014/05/Abstract-Book-FINAL.pdf.
Wilens, T. et al., "A Pilot Study of a Novel Monoamine Triple Reuptake Inhibitor EB-1020 SR In the Treatment of ADHD in Adults," ASCP Annual Meeting 2014, Abstract Book—Posters, 165 pages, Poster Session 1, Abstract P-2, pp. 1-2, retrieved on Mar. 23, 2017, from: http://ascpmeeting.org/wp-content/uploads/2014/06/Poster-Abstracts-FINAL.pdf.
Wilens, T. et al., "A Pilot Study of a Novel Monoamine Triple Reuptake Inhibitor EB-1020 SR in the Treatment of ADHD in Adults," Presentation Abstract, Society of Biological Psychiatry, 69th Annual Scientific Meeting, 2014, 3 pages, retrieved on Mar. 23, 2017, from: http://www.abstractsonline.com/Plan/ViewAbstractaspx?sKey=75f91598-6832-4c38-8f08-1d1ea0324ebO&cKey=c39a37b8-cbb9-4a9b-a3f6-a8lb6lfa567b&mKey=%7b1BED6AAA-7084-4C45-BFOC-41B6D73E7FD7%7d.
Wilens, T. et al., "A Pilot Study of a Novel Monoamine Triple Reuptake Inhibitor, Centanafadine (EB-1020) SR, In the Treatment of Attention-Deficit Hyperactivity Disorder in Adult Males," Poster, ASCP Annual Meeting 2014, 1 page.
Wilens, T. et al., "A Pilot Study of a Novel Monoamine Triple Reuptake Inhibitor, EB-1020 SR, In the Treatment of Attention-Deficit Hyperactivity Disorder in Adult Males," Poster, 2014, Society of Biological Psychiatry, 69th Annual Scientific Meeting, 1 page.
Wilens, T. et al., "An Open-Label Study of the Tolerability of Mixed Amphetamine Salts in Adults with Attention-Deficit/Hyperactivity Disorder and Treated Primary Essential Hypertension," Journal of Clinical Psychiatry, 2006, 67 (5), 696-702.
Wilens, T. et al., "Understanding Attention-Deficit/Hyperactivity Disorder from Childhood to Adulthood," Postgraduate Medicine, 2010, 122 (5), 97-109.
Wolff, M., Ed., Burger's Medicinal Chemistry, Fifth Edition, vol. I, pp. 975-977.
Wong, E. et al., "Reboxetine: A Pharmacologically Potent, Selective, and Specific Norepinephrine Reuptake Inhibitor," Biological Psychiatry, 2000, 47 (9), 818-829.
Written Opinion of the International Search Authority, dated Oct. 16, 2012, in International Application No. PCT/US2012/00335, 4 pages.
Xu, F. et al., "Chlorination/Cyclodehydration of Amino Alcohols with SOC12: An Old Reaction Revisited," Journal of Organic Chemistry, 2008, 73, 312-315.
Xu, F. et al., "Stereocontrolled Synthesis of Trisubstituted Cyclopropanes: Expedient, Atom-Economical, Asymmetric Syntheses of (+)-Bicifadine and DOV21947," Organic Letters, 2006, 8 (17), 3885-3888.
Xu, F. et al., Supporting Information for "Chlorination/Cyclodehydration of Amino Alcohols with SOC12: An Old Reaction Revisited," Journal of Organic Chemistry, 2008, S1-S32, available at: http://pubs.acs.org/doi/suppl/10.1021/jo701877h.
Xu, F. et al., Supporting Information for "Stereocontrolled Synthesis of Trisubstituted Cyclopropanes: Expedient, Atom-Economical, Asymmetric Syntheses of (+)-Bicifadine and DOV21947," Organic Letters, 2006, S1-S14, available at: http://pubs.acs.org/doi/suppl/10.1021/01061650w.
Yuki, H. et al., "Studies on Antiviral Agents. II. Synthesis and Biological Activity of Maleimide Derivatives," Chemical and Pharmaceutical Bulletin, 1967, 15 (8), 1101-1106.
Zhang, K., et al., "Role of Dopamine D4 Receptors in Motor Hyperactivity Induced by Neonatal 6-Hydroxydopamine Lesions in Rats," Neuropsychopharmacology, 2001, 25 (5), 624-632.
Zhang, M. et al., "Studies on the Structure-Activity Relationship of Bicifadine Analogs as Monoamine Transporter Inhibitors," Bioorganic and Chemistry Letters, 2008, 18 (13), 3682-3686.

* cited by examiner

USE OF (1R,5S)-(+)-1-(NAPHTHALEN-2-YL)-3-AZABICYCLO[3.1.0]HEXANE IN THE TREATMENT OF CONDITIONS AFFECTED BY MONOAMINE NEUROTRANSMITTERS

RELATED APPLICATIONS

This application is a continuation of U.S. patent application Ser. No. 13/907,921, filed Jun. 2, 2013, which is a continuation of U.S. patent application Ser. No. 13/751,169, filed Jan. 28, 2013, which is a continuation of U.S. patent application Ser. No. 13/528,940, filed Jun. 21, 2012, which is a continuation of U.S. patent application Ser. No. 13/334,066, filed Dec. 22, 2011, which claims priority benefit of U.S. Provisional patent application Ser. No. 61/574,231, filed Jul. 30, 2011, the disclosures of each of which are incorporated herein in their entirety by reference.

TECHNICAL FIELD

The present invention relates to compositions comprising (1R,5S)-(+)-1-(naphthalen-2-yl)-3-azabicyclo[3.1.0]hexane and methods for use of these compositions for treatment and prevention of central nervous system disorders and other conditions affected by monoamine neurotransmitters.

BACKGROUND OF THE INVENTION

Attention-deficit hyperactivity disorder (ADHD) is a central nervous system (CNS) disorder characterized by developmentally inappropriate inattention, hyperactivity, and impulsivity (Buitelaar et al., 2010; Spencer et al., 2007). ADHD is one of the most common developmental disorders in children with 5-10% prevalence (Scahill et al., 2000; Polanczyk et al., 2007). While ADHD was once regarded as only a childhood disorder, it can continue through adolescence and into adulthood. An estimated 2.9-4.4% of the adult population has continuing ADHD (Kessler et al., 2006; Faraone and Biederman, 2005). Major symptoms in adults include inattention, disorganization, lack of concentration and to some extent impulsivity, which result in difficulty functioning, low educational attainment, under achievement in vocational and educational pursuits, and poor social and family relations (Biederman et al., 2006; Barkely et al., 2006).

The exact causes of ADHD are not known, but a dysfunction of the prefrontal cortex and its associated circuitries has been posited as a key deficit in ADHD (Arnsten, 2009). Consistent with this notion is the finding that abnormal catecholaminergic function plays a key role, particularly in prefrontal cortical regions (Arnsten 2009). The catecholamines norepinephrine (NE) and dopamine (DA) are highly involved in several domains of cognition including working memory, attention, and executive function. Accordingly, these monoamine neurotransmitters are believed to work in concert in modulating cognitive processes.

Pharmacotherapy is a primary form of treatment utilized to reduce the symptoms of ADHD. Stimulants such as methylphenidate and amphetamines are commonly used for ADHD. The major mechanism of action of the stimulants is inhibition of DA and NE transporters. The stimulants are effective against the core symptoms of ADHD and have a response rate of about 70% (Spencer et al., 2005). However, major concerns about stimulants include risk of abuse, dependency, and diversion as well as potential neurotoxic effects of amphetamines (Berman et al., 2009). The abuse potential of stimulants is particularly problematic in adults because substance abuse is a common co-morbidity with adult ADHD (Levin and Kleber, 1995; Ohlmeier, 2008).

Another major drug used to treat ADHD is atomoxetine, which is a selective norepinephrine reuptake inhibitor. Major advantages of atomoxetine compared to the stimulants is lack of abuse potential, once-daily dosage, and superior treatment of co-morbidities such as anxiety and depression. However, atomoxetine has lower efficacy and takes 2-4 weeks for onset of action (Spencer et al., 1998; Newcorn et al., 2008).

Accordingly, there remains a need for effective pharmaceuticals which may be used in the treatment of ADHD and other conditions affected by monoamine neurotransmitters.

SUMMARY OF EXEMPLARY EMBODIMENTS

Provided herein are compositions and methods using an unbalanced triple reuptake inhibitor, (1R,5S)-(+)-1-(naphthalen-2-yl)-3-azabicyclo[3.1.0]hexane as shown below, and pharmaceutically acceptable active salts, polymorphs, hydrates, derivatives and prodrugs thereof, for the treatment of mammals, including humans, suffering from signs and symptoms of central nervous system (CNS) disorders and other conditions amenable to treatment involving administration of a triple monoamine reuptake inhibitor including, but not limited to, adult ADHD, pediatric ADHD, oppositional defiance disorder, conduct disorder, substance abuse, depression, anxiety disorders (panic, generalized anxiety, obsessive compulsive disorder, post-traumatic stress disorder), autism, traumatic brain injury, cognitive impairment, and schizophrenia (particularly for cognition), obesity, chronic pain disorders, personality disorder, and mild cognitive impairment. Unbalanced as used herein refers to the relative effects on each of the monoamine transporters. In this case reference is made to a triple reuptake inhibitor with the most activity against the norepinephrine transporter, one sixth as much to the dopamine transporter and one fourteenth to the serotonin transporter. In contrast, a balanced triple reuptake inhibitor would have similar activity against each of the three monoamine transporters.

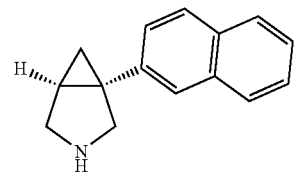

(1R,5S)-(+)-1-(naphthalen-2-yl)-3-azabicyclo[3.1.0]hexane (1R,5S)-(+)-1-(naphthalen-2-yl)-3-azabicyclo[3.1.0]hexane or a pharmaceutically acceptable salt thereof as used herein is substantially free of the corresponding (−) enantiomer, (1R,5 S)-(−)-1-(naphthalen-2-yl)-3-azabicyclo[3.1.0]hexane.

(1R,5S)-(+)-1-(naphthalen-2-yl)-3-azabicyclo[3.1.0]hexane may be in the form of a pharmaceutically acceptable active salt. Pharmaceutically acceptable salts may include inorganic and organic acid addition salts such as hydrochloride salt.

It is shown herein that use of (1R,5S)-(+)-1-(naphthalen-2-yl)-3-azabicyclo[3.1.0]hexane or a pharmaceutically acceptable salt thereof is effective in treating, preventing, alleviating, or moderating disorders affected by monoamine neurotransmitters or biogenic amines, specifically disorders that are alleviated by inhibiting norepinephrine and/or dopamine and/or serotonin reuptake.

Additionally provided herein are combinatorial compositions and coordinate treatment means using additional or secondary psychotherapeutic agents in combination with of (1R,5S)-(+)-1-(naphthalen-2-yl)-3-azabicyclo[3.1.0]hexane or a pharmaceutically acceptable salt thereof. Suitable secondary psychotherapeutic drugs for use in the compositions and methods herein include, but are not limited to, drugs from the general classes of anti-psychotic, antidepressants, anti-convulsant, mood-stabilizing, anxiolytic, benzodiazepines, calcium channel blockers, and anti-inflammatories. (See, e.g., R J. Baldessarini in Goodman & Gilman's The Pharmacological Basis of Therapeutics, 11th Edition, Chapters 17 and 18, McGraw-Hill, 2005 for a review). Exemplary atypical antipsychotics include, for example, aripiprazole, ziprasidone, risperidone, quetiepine, or olanzapine. Exemplary antidepressants include, for example, tri-cyclic antidepressants (TCAs), specific monoamine reuptake inhibitors, selective serotonin reuptake inhibitors, selective norepinephrine or noradrenaline reuptake inhibitors, selective dopamine reuptake inhibitors, norepinephrine-dopamine reuptake inhibitors, serotonin-norepinephrine reuptake inhibitors, multiple monoamine reuptake inhibitors, monoamine oxidase inhibitors, atypical antidepressants, atypical antipsychotics, anticonvulsants, or opiate agonists.

Additional background information pertaining to (1R,5S)-(+)-1-(naphthalen-2-yl)-3-azabicyclo[3.1.0]hexane of the present invention may be found, for example, in U.S. patent application Ser. No. 11/493,431, U.S. patent application Ser. No. 11/936,016, U.S. patent application Ser. No. 12/135,053, U.S. patent application Ser. No. 12/334,432, and U.S. patent application Ser. No. 12/895,788, each of which is incorporated herein by reference in their entirety.

The present invention may be understood more fully by reference to the detailed description and examples which are intended to exemplify non-limiting embodiments of the invention.

BRIEF DESCRIPTION OF THE DRAWINGS

FIG. 7A shows values at 5 min. intervals; FIG. 7B shows values at 15, 60, and 90 min. Values are mean±SEM of locomotor activity count. *=p<0.05 versus vehicle.

DETAILED DESCRIPTION OF EXEMPLARY EMBODIMENTS

Figure 1A:
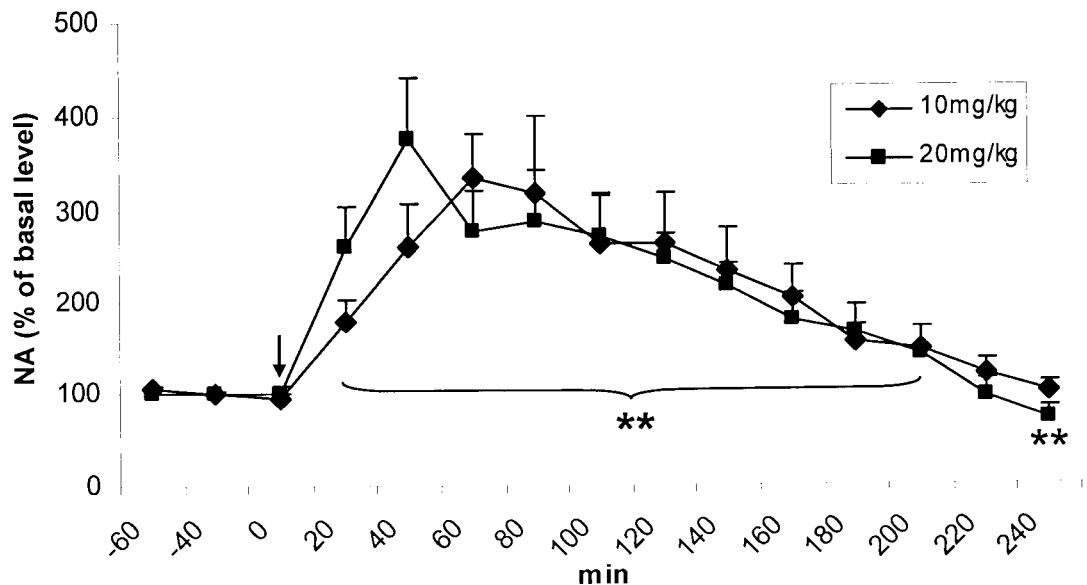
FIGS. 1A, 1B, and 1C are graphs showing that (1R,5S)-(+)-1-(naphthalen-2-yl)-3-azabicyclo[3.1.0]hexane increased extracellular concentrations of norepinephrine (NE) (FIG. 1A), dopamine (DA) (FIG. 1B), and serotonin (5-HT) (FIG. 1C) in rat prefrontal cortex. (1R,5S)-(+)-1-(naphthalen-2-yl)-3-azabicyclo[3.1.0]hexane was injected at time zero as indicated. Values are mean±SEM (n=6-8) of baseline concentrations of the respective monoamines. **<0.01 show significant difference in neurotransmitter level above baseline.

Described herein is (1R,5S)-(+)-1-(naphthalen-2-yl)-3-azabicyclo[3.1.0]hexane which provides therapeutic efficacy in the treatment of conditions affected by monoamine neurotransmitters including, but not limited to, adult ADHD, pediatric ADHD, oppositional defiance disorder, conduct disorder, substance abuse, depression, anxiety disorders (panic, generalized anxiety, obsessive compulsive disorder, post-traumatic stress disorder), autism, traumatic brain injury, cognitive impairment, and schizophrenia (particularly for cognition), obesity, chronic pain disorders, personality disorder, and mild cognitive impairment. Further described herein are coordinate treatment methods and combined drug compositions, dosage forms, packages, and kits for preventing or treating conditions affected by monoamine neurotransmitters including, but not limited to, ADHD.

(1R,5S)-(+)-1-(naphthalen-2-yl)-3-azabicyclo[3.1.0] hexane is a triple reuptake inhibitor (TRI), that inhibits the reuptake of the biogenic amines norephinephrine, dopamine, and serotonin. It was previously described in U.S. patent application Ser. No. 12/334,432. It possesses a desirable unbalanced triple monoamine uptake inhibition ratio, with highly potent norepinephrine reuptake inhibition and lesser dopamine and, even lesser serotonin reuptake inhibition in a ratio of ~1:6:14, respectively (IC 50 values of 6, 38, and 83 nM, respectively, determined in MDCK, CHO-K1, and HEK 293 cells respectively expressing the corresponding human recombinant transporters for [3H]norepinephrine, [3H]dopamine, and [3H]serotonin; see Example II).

This profile of robust reuptake inhibition of NE coupled with the lesser reuptake inhibition of DA supports that (1R,5S)-(+)-1-(naphthalen-2-yl)-3-azabicyclo[3.1.0]hexane will be efficacious in treating ADHD. Norepinephrine and dopamine are highly involved in several domains of cognition including working memory, attention, and executive function, and are believed to work in concert in modulating cognitive processes. Compared to the norephinephrine uptake inhibitor atomoxetine, (1R,5S)-(+)-1-(naphthalen-2-yl)-3-azabicyclo[3.1.0]hexane has the added advantage of enhancing dopamine function, but without the disadvantages of psychostimulants, which have pronounced dopaminergic activities (Bymaster et al., 2002). Support for this concept is provided by a clinical study in which atomoxetine efficacy was augmented by subsequent administration of the stimulant methylphenidate, a DA/NE reuptake inhibitor (Wilens et al., 2009). In that study, atomoxetine significantly improved scores on all executive function measurements including working memory and organization, and the addition of methylphenidate gave a significant further improvement. However, the combination had side effects including increased rates of insomnia, irritability, appetite suppression, and a small increase in diastolic blood pressure (Hammerness et al., 2009). Thus this study indicates the combination of reuptake inhibition of NE and DA is effective for treating ADHD, while pointing out the disadvantages of stimulants. (1R,5S)-(+)-1-(naphthalen-2-yl)-3-azabicyclo[3.1.0]hexane advantageously may activate NE and DA circuitries involved with attention without being stimulant-like.

The profile of (1R,5S)-(+)-1-(naphthalen-2-yl)-3-azabicyclo[3.1.0]hexane supports that it will be beneficial for treatment of substance abuse, including but not limited to, alcohol, nicotine, opioids and stimulants like cocaine and methamphetamine. The dopamine and norepinephrine reuptake inhibitor bupropion is useful and approved for treatment of nicotine addiction (Hayes et al., 2003). The effects of (1R,5S)-(+)-1-(naphthalen-2-yl)-3-azabicyclo[3.1.0]hexane on norepinephrine and dopamine reuptake indicate that it will likewise be useful in treating nicotine addiction. Furthermore, bupropion has been shown to be effective in treatment of methamphetamine and other stimulant abuse (Elkashef et al., 2008), indicating that (1R,5S)-(+)-1-(naphthalen-2-yl)-3-azabicyclo[3.1.0]hexane may likewise be useful in treating stimulant abuse. Chronic methamphetamine use may result in low dopaminergic tone and dopamine uptake inhibitors may help restore dopamine homeostasis in the synaptic cleft. As shown herein using an animal model, (1R,5S)-(+)-1-(naphthalen-2-yl)-3-azabicyclo[3.1.0]hexane increased dopamine in dopamine-rich areas like the striatum, supporting its efficacy for stimulant abuse. Dopamine transporter ligands are hypothesized to be useful in the treatment of substance abuse as the ligand/drug would be expected to partially substitute for the stimulant, and block the drug of abuse access to the transporters, thus decreasing stimulant self-administration and minimizing the craving for the stimulant. (1R,5S)-(+)-1-(naphthalen-2-yl)-3-azabicyclo[3.1.0]hexane is shown herein to increase dopamine in the striatum of an animal model without stimulating locomotor activity. Accordingly, (1R,5S)-(+)-1-(naphthalen-2-yl)-3-azabicyclo[3.1.0]hexane may reduce reward threshold and be beneficial in treating substance abuse, but without the abuse potential of potent dopamine uptake blocking/releasing compounds.

Provided herein are compositions and methods of (1R,5S)-(+)-1-(naphthalen-2-yl)-3-azabicyclo[3.1.0]hexane, as shown below, or a pharmaceutically acceptable salt thereof, for the treatment of mammals, including humans, suffering from signs and symptoms of disorders generally treated with norephinephrine and dopamine reuptake inhibitors including, but not limited to, ADHD, oppositional defiance disorder, conduct disorder, substance abuse, depression, anxiety disorders, autism, traumatic brain injury, cognitive impairment, and schizophrenia.

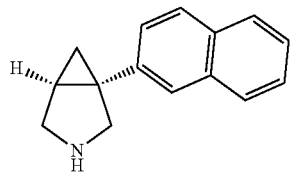 [SMILES: c1ccc2cc([C@]34CNC[C@H]3C4)ccc2c1]

(1R,5S)-(+)-1-(naphthalen-2-yl)-3-azabicyclo[3.1.0]hexane (1R,5S)-(+)-1-(naphthalen-2-yl)-3-azabicyclo[3.1.0]hexane may be prepared by any means generally used for preparing such a compound. Synthesis of the compound is detailed below in Example I. Additional exemplary means of preparing (1R,5S)-(+)-1-(naphthalen-2-yl)-3-azabicyclo[3.1.0]hexane may be found, for example, in U.S. patent application Ser. No. 12/334,432, which is incorporated herein by reference in its entirety.

(1R,5S)-(+)-1-(naphthalen-2-yl)-3-azabicyclo[3.1.0]hexane as used herein is substantially free of the corresponding (−) enantiomer, (1R,5S)-(−)-1-(naphthalen-2-yl)-3-azabicyclo[3.1.0]hexane. As used herein, the term "substantially pure (1R,5S)-(+)-1-(naphthalen-2-yl)-3-azabicyclo[3.1.0]hexane" means that the compositions contain more (1R,5S)-(+)-1-(naphthalen-2-yl)-3-azabicyclo[3.1.0]hexane than (1R,5S)-(−)-1-(naphthalen-2-yl)-3-azabicyclo[3.1.0]hexane. Specifically, the compositions refer to an enantiomeric excess greater than 80%, preferably greater than 90%, more preferably greater than 95%, and most preferably greater than 98% of (1R,5S)-(+)-1-(naphthalen-2-yl)-3-azabicyclo[3.1.0]hexane as determined by configuration and/or optical activity. Typically, the compositions contain no more than about 5% w/w of the corresponding (−) enantiomer, more preferably no more than about 2%, more preferably no more than about 1% w/w of the corresponding (−) enantiomer of (1R,5S)-(+)-1-(naphthalen-2-yl)-3-azabicyclo[3.1.0]hexane.

(1R,5S)-(+)-1-(naphthalen-2-yl)-3-azabicyclo[3.1.0]hexane can be prepared as an acid addition salt formed from an acid and the basic nitrogen group of (1R,5S)-(+)-1-(naphthalen-2-yl)-3-azabicyclo[3.1.0]hexane. Suitable acid addition salts are formed from acids, which form non-toxic salts, examples of which are hydrochloride, hydrobromide, hydroiodide, sulphate, hydrogen sulphate, nitrate, phosphate, and hydrogen phosphate. Examples of pharmaceutically acceptable addition salts include inorganic and organic acid addition salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; organic acid salts such as acetate, citrate, lactate, succinate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate, tartrate, gluconate and the like. The hydrochloride salt formed with hydrochloric acid is an exemplary useful salt.

As disclosed herein, (1R,5S)-(+)-1-(naphthalen-2-yl)-3-azabicyclo[3.1.0]hexane or a pharmaceutically acceptable salt thereof is effective in treating a variety of conditions, but not limited to, ADHD, substance abuse, depression, anxiety disorders, autism, traumatic brain injury, cognitive impairment, and schizophrenia (particularly for cognition), obesity, chronic pain disorders, personality disorder, and mild cognitive impairment. Within related aspects of the invention, combinatorial formulations are provided that use substantially pure (1R,5S)-(+)-1-(naphthalen-2-yl)-3-azabicyclo[3.1.0]hexane or a pharmaceutically acceptable salt thereof alone or in combination with other psychotherapeutic drugs to modulate, prevent, alleviate, ameliorate, reduce or treat symptoms or conditions influenced by monoamine neurotransmitters or biogenic amines. Subjects amenable to treatment according to the invention include mammalian subjects, including humans, suffering from or at risk for any of a variety of conditions including, but not limited to, ADHD, depression, anxiety, panic disorder, post-traumatic stress disorder, obsessive compulsive disorder, schizophrenia and allied disorders, obesity, tic disorders, addiction, Parkinson's disease, and chronic pain.

(1R,5S)-(+)-1-(naphthalen-2-yl)-3-azabicyclo[3.1.0] hexane or a pharmaceutically acceptable salt thereof may be administered alone or in combination with one or more other psychotherapeutic drugs including, but not limited to, drugs from the general classes of anti-convulsant, mood-stabilizing, anti-psychotic, anxiolytic, benzodiazepines, calcium channel blockers, and antidepressants. (See, e.g., R J. Baldessarini in Goodman & Gilman's The Pharmacological Basis of Therapeutics, 11th Edition, Chapters 17 and 18, McGraw-Hill, 2005 for a review). Within the coordinate administration methods of the invention, the secondary therapeutic and/or psychotherapeutic drug is administered concurrently or sequentially with (1R,5S)-(+)-1-(naphthalen-2-yl)-3-azabicyclo[3.1.0]hexane or a pharmaceutically acceptable salt thereof to treat or prevent one or more symptoms of the targeted disorder. When administered simultaneously, the additional therapeutic and/or psychotherapeutic agent and (1R,5S)-(+)-1-(naphthalen-2-yl)-3-azabicyclo[3.1.0]hexane or a pharmaceutically acceptable salt thereof may be combined in a single composition or combined dosage form.

Alternatively, the combinatorially effective additional therapeutic and/or psychotherapeutic drug (1R,5S)-(+)-1-(naphthalen-2-yl)-3-azabicyclo[3.1.0]hexane or a pharmaceutically acceptable salt thereof may be administered at the same time in separate dosage forms. When the coordinate administration is conducted simultaneously or sequentially, the additional therapeutic and/or psychotherapeutic agent and (1R,5S)-(+)-1-(naphthalen-2-yl)-3-azabicyclo[3.1.0] hexane or a pharmaceutically acceptable salt thereof may each exert biological activities and therapeutic effects over different time periods, although a distinguishing aspect of all coordinate treatment methods of the invention is that treated subjects exhibit positive therapeutic benefits.

Administration (1R,5S)-(+)-1-(naphthalen-2-yl)-3-azabicyclo[3.1.0]hexane or a pharmaceutically acceptable salt thereof or the coordinate treatment method or combinatorial drug composition of the invention to suitable subjects will yield a reduction in one or more target symptom(s) associated with the selected disorder or development of the disorder by at least 2%, 5%, 10%, 20%, 30%, 50% or greater, up to a 75-90%, or 95% or greater, compared to placebo-treated or other suitable control subjects. Comparable levels of efficacy are contemplated for the entire range of disorders described herein, including all contemplated neurological and psychiatric disorders, and related conditions and symptoms, for treatment or prevention using the compositions and methods of the invention. These values for efficacy may be determined by comparing accepted therapeutic indices or clinical values for particular test and control individuals over a course of treatment/study, or more typically by comparing accepted therapeutic indices or clinical values between test and control groups of individuals using standard human clinical trial design and implementation.

As used herein, the terms "prevention" and "preventing," when referring to a disorder or symptom, refers to a reduction in the risk or likelihood that a mammalian subject will develop said disorder, symptom, condition, or indicator after treatment according to the invention, or a reduction in the risk or likelihood that a mammalian subject will exhibit a recurrence or relapse of said disorder, symptom, condition, or indicator once a subject has been treated according to the invention and cured or restored to a normal state (e.g., placed in remission from a targeted disorder). As used herein, the terms "treatment" or "treating," when referring to the targeted disorder, refers to inhibiting or reducing the progression, nature, or severity of the subject condition or delaying the onset of the condition.

In accordance with the invention, compounds disclosed herein, optionally formulated with additional ingredients in a pharmaceutically acceptable composition, are administered to mammalian subjects, for example a human patient, to treat or prevent one or more symptom(s) of a disorder alleviated by inhibiting norepinephrine reuptake, and/or dopamine reuptake, and/or serotonin reuptake. In certain embodiments, "treatment" or "treating" refers to amelioration of one or more symptom(s) of a disorder, whereby the symptom(s) is/are alleviated by inhibiting dopamine and/or norepinephrine and/or serotonin reuptake. In other embodiments, "treatment" or "treating" refers to an amelioration of at least one measurable physical parameter associated with a disorder. In yet another embodiment, "treatment" or "treating" refers to inhibiting or reducing the progression or severity of a disorder (or one or more symptom(s) thereof) alleviated by inhibiting dopamine and/or norepinephrine and/or serotonin reuptake, e.g., as discerned based on physical, physiological, and/or psychological parameters. In additional embodiments, "treatment" or "treating" refers to delaying the onset of a disorder (or one or more symptom(s) thereof) alleviated by inhibiting norephinephrine and/or dopamine and/or serotonin reuptake.

An "effective amount," "therapeutic amount," "therapeutically effective amount," or "effective dose" of (1R,5S)-(+)-1-(naphthalen-2-yl)-3-azabicyclo[3.1.0]hexane or a pharmaceutically acceptable salt thereof and/or an additional psychotherapeutic agent as used herein means an effective amount or dose of the active compound as described herein sufficient to elicit a desired pharmacological or therapeutic effect in a human subject. In the case of therapeutic agents for ADHD or substance abuse, these terms most often refer to a significant reduction in an occurrence, frequency, or severity of one or more symptom(s) of a specified disorder, including any combination of neurological and/or psychological symptoms, diseases, or conditions, associated with or caused by the targeted disorder.

As disclosed herein, (1R,5S)-(+)-1-(naphthalen-2-yl)-3-azabicyclo[3.1.0]hexane or a pharmaceutically acceptable salt thereof is effective in treating a variety of conditions including ADHD. This disorder is distinguished by symptoms of difficulty staying focused and paying attention, difficulty controlling behavior, impulsivity, disorganization, and hyperactivity (over-activity). ADHD is diagnosed in both children and adults based on criteria described in the Diagnostic and Statistical Manual of Mental Disorders, Fourth Edition (2000), Text Revision (DSM-IV-TR), American Psychiatric Association, Washington, D.C. The DSM-IV-TR criteria describe three subtypes of ADHD: Attention Deficit Hyperactivity Disorder-predominantly hyperactive-impulsive subtype; Attention Deficit Hyperactivity Disorder-predominantly inattentive subtype (also referred as Attention Deficit Disorder or ADD); and Attention Deficit Hyperactivity Disorder-combined subtype. In the predominantly inattentive type, a person can have six or more of the following disruptive and age-inappropriate symptoms: difficulty paying attention to details, difficulty keeping attention on tasks, difficulty following instructions, difficulty organizing activities, difficulty following conversations, being easily distracted, and forgetful of daily routines. In the predominantly hyperactive-impulsive type, a person can have six or more of the following disruptive and age-inappropriate symptoms: fidgeting often, inappropriate running about, trouble playing or enjoying leisure activities quietly, excessive talking, blurting out answers, trouble waiting turn, and interrupting others. In the combined type, both inattentive and hyperactive-impulsive behaviors can be present. (1R,5S)-(+)-1-(naphthalen-2-yl)-3-azabicyclo[3.1.0]hexane or a pharmaceutically acceptable salt thereof is effective in treating all subtypes of ADHD, both in adult and pediatric ADHD. (1R,5S)-(+)-1-(naphthalen-2-yl)-3-azabicyclo[3.1.0]hexane or a pharmaceutically acceptable salt thereof is likewise effective in treating ADHD allied disorders, such as Attention-Deficit/Hyperactivity Disorder not otherwise specified (NOS); Conduct Disorder; Oppositional Defiant Disorder; and Disruptive Behavior Disorder not otherwise specified (NOS).

Therapeutic efficacy can alternatively be demonstrated by a decrease in the frequency or severity of symptoms associated with the treated condition or disorder, or by altering the nature, occurrence, recurrence, or duration of symptoms associated with the treated condition or disorder. In this context, "effective amounts," "therapeutic amounts," "therapeutically effective amounts," and "effective doses" of additional psychotherapeutic drugs (1R,5S)-(+)-1-(naphthalen-2-yl)-3-azabicyclo[3.1.0]hexane or a pharmaceutically acceptable salt thereof within the invention can be readily determined by ordinarily skilled artisans following the teachings of this disclosure and employing tools and methods generally known in the art, often based on routine clinical or patient-specific factors.

Efficacy of the coordinate treatment methods and drug compositions of the invention will often be determined by use of conventional patient surveys or clinical scales to measure clinical indices of disorders in subjects. The methods and compositions of the invention will yield a reduction in one or more scores or selected values generated from such surveys or scales completed by test subjects (indicating for example an incidence or severity of a selected disorder), by at least 5%, 10%, 20%, 30%, 50% or greater, up to a 75-90%, or 95% compared to correlative scores or values observed for control subjects treated with placebo or other suitable control treatment. In at risk populations, the methods and compositions of the invention will yield a stable or minimally variable change in one or more scores or selected values generated from such surveys or scales completed by test subjects. More detailed data regarding efficacy of the methods and compositions of the invention can be determined using alternative clinical trial designs.

Useful patient surveys and clinical scales for comparative measurement of clinical indices of psychiatric disorders in subjects treated using the methods and compositions of the invention can include any of a variety of widely used and well known surveys and clinical scales. Several surveys are available for ADHD, including assessments for adults, children, those rated by clinical investigators, and those rated by subjects treated. Among these useful tools are the Wender Utah Rating Scale (WURS) (Ward et al., 1993); Adult Rating Scale (ARS) (Weyandt et al., 1995); Curent Symptoms Scale (CSS) (Barkley and Murphy, 1998); Conners Adult ADHD Rating Scale (CAARS) (Conners et al., 1999); Adult Problems Questionnaire (APQ) (De Quiros and Kinsbourne, 2001); Young Adult Rating Scale (YARS) (Du Paul et al., 2001); Assessment of Hyperactivity and Attention (AHA) (Mehringer et al., 2002); Attention Deficit Scales for Adults (ADSA) (Triolo and Murphy, 1996); ADHD Rating Scale (ADHD-RS) (Du Paul et al., 1998); Brown Attention Deficict Disorder Series (BADDS) (Brown, 1996); Symptom Inventory (SI) (McCann and Roy-Byrne, 2004); Young Adult Questionnaire (YAQ) (Young, 2004); Adult Self Report Scale (ASRS) (Adler et al., 2006), and the Caterino Scale (Caterino et al., 2009).

The methods and compositions of the invention will yield a reduction in one or more scores or values generated from these clinical surveys (using any single scale or survey, or any combination of one or more of the surveys described above) by at least 10%, 20%, 30%, 50% or greater, up to a 75-90%, or 95% compared to correlative scores or values observed for control subjects treated with placebo or other suitable control treatment. In prophylactic treatment, the methods and compositions of the invention will yield a stabilization or diminished change in the scores or values generated from these clinical surveys.

(1R,5S)-(+)-1-(naphthalen-2-yl)-3-azabicyclo[3.1.0]hexane or a pharmaceutically acceptable salt thereof is useful for treating or preventing endogenous disorders alleviated by inhibiting norepinephrine and/or dopamine and/or serotonin reuptake. In addition to ADHD, such disorders include, but are not limited to, addictive and substance abuse disorders, depression, anxiety disorder, panic disorder, conduct disorder, autism, traumatic brain injury, cognitive impairment, obesity, chronic pain disorders, personality disorder, obsessive compulsive disorder, schizophrenia and allied disorders, Parkinson's disease, and tic disorders, such as Tourette's syndrome.

(1R,5S)-(+)-1-(naphthalen-2-yl)-3-azabicyclo[3.1.0]hexane or a pharmaceutically acceptable salt thereof may be therapeutic for depressive disorders, including but not limited to, major depressive disorder, recurrent; dysthymic disorder; depressive disorder not otherwise specified (NOS); major depressive disorder, single episode; depression associated with bipolar disorder, alzheimers, psychosis or Parkinson's disease; postnatal depression; and seasonal affected disorder. Anxiety disorders amenable to treatment with compositions disclosed herein include panic disorder, general anxiety disorder, obsessive compulsive disorder, post traumatic stress disorder, and social anxiety disorder. Addictive disorders amenable for treatment and/or prevention employing the methods and compositions of the invention include, but are not limited to, eating disorders, impulse control disorders, alcohol-related disorders, nicotine-related disorders, amphetamine-related disorders, cannabis-related disorders, cocaine-related disorders, hallucinogen use disorders, inhalant-related disorders, and opioid-related disorders. Substance abuse disorders amenable to treatment with (1R,5S)-(+)-1-(naphthalen-2-yl)-3-azabicyclo[3.1.0]hexane or a pharmaceutically acceptable salt thereof include, but are not limited to alcohol-related disorders, nicotine-related disorders, amphetamine-related disorders, *cannabis*-related disorders, cocaine-related disorders, hallucinogen-use disorders, inhalant-related disorders, and opioid-related disorders.

Disorders alleviated by (1R,5S)-(+)-1-(naphthalen-2-yl)-3-azabicyclo[3.1.0]hexane or a pharmaceutically acceptable salt thereof are not limited to the specific disorders described herein, and the compositions and methods disclosed herein will be understood or readily ascertained to provide effective agents for treating and/or preventing a wide range of additional disorders and associated symptoms. For example, the compounds of the invention will provide promising candidates for treatment and/or prevention of cognitive disorders, bipolar disorder, anorexia nervosa, bulimia nervosa, cyclothymic disorder, chronic fatigue syndrome, chronic or acute stress, learning disorders, reading problems, gambling addiction, manic symptoms, phobias, panic attacks, academic problems in school, smoking, abnormal sexual behaviors, schizoid behaviors, sleep disorders, stuttering, fibromyalgia and other somatoform disorders (including somatization disorder, conversion disorder, pain disorder, hypochondriasis, body dysmorphic disorder, undifferentiated somatoform disorder, and somatoform NOS, incontinence (i.e., stress incontinence, genuine stress incontinence, and mixed incontinence), inhalation disorders, mania, migraine headaches, and peripheral neuropathy.

By virtue of their multiple reuptake inhibitor activity, the novel compounds of the present invention are thus useful in a wide range of veterinary and human medical applications, in particular for treating and/or preventing a wide array of disorders and/or associated symptom(s) alleviated by inhibiting norepinephrine and/or dopamine. The unbalanced norepinephrine-dopamine-serotonin reuptake inhibition ratio of −1:6:14, respectively of (1R,5S)-(+)-1-(naphthalen-2-yl)-3-azabicyclo[3.1.0]hexane provides for higher dosages of (1R,5S)-(+)-1-(naphthalen-2-yl)-3-azabicyclo[3.1.0]hexane to be used without triggering substance abuse associated with dopamine and dopaminergic side effects such as elevated heart rate, increased blood pressure, insomnia, appetite suppression, and irritability seen in dosages of stimulant medications.

Within additional aspects of the invention, combinatorial formulations and coordinate administration methods are provided which employ an effective amount of a (1R,5S)-(+)-1-(naphthalen-2-yl)-3-azabicyclo[3.1.0]hexane or a pharmaceutically acceptable salt thereof, and one or more additional active agent(s) that is/are combinatorially formulated or coordinately administered with the compound of the invention--yielding a combinatorial formulation or coordinate administration method that is effective to modulate, alleviate, treat or prevent a targeted disorder, or one or more symptom(s) thereof, in a mammalian subject. Exemplary combinatorial formulations and coordinate treatment methods in this context comprise a therapeutic compound of the invention in combination with one or more additional or adjunctive treatment agents or methods for treating the targeted disorder or symptom(s), for example one or more antidepressant or anxiolytic agent(s) and/or therapeutic method(s).

In related embodiments of the invention, the compounds disclosed herein can be used in combination therapy with at least one other therapeutic agent or method. In this context, compounds of the invention can be administered concurrently or sequentially with administration of a second therapeutic agent, for example a second agent that acts to treat or prevent the same, or different, disorder or symptom(s) for which the compound of the invention is administered. The compound of the invention and the second therapeutic and/or psychotherapeutic agent can be combined in a single composition or administered in different compositions. The second therapeutic and/or psychotherapeutic agent may also be effective for treating and/or preventing a disorder or associated symptom(s) by inhibiting dopamine and/or norepinephrine and/or serotonin reuptake. The coordinate administration may be done simultaneously or sequentially in either order, and there may be a time period while only one or both (or all) active therapeutic agents, individually and/or collectively, exert their biological activities and therapeutic effects. A distinguishing aspect of all such coordinate treatment methods is that the compound of the invention exerts at least some detectable therapeutic activity toward alleviating or preventing the targeted disorder or symptom(s), as described herein, and/or elicit a favorable clinical response, which may or may not be in conjunction with a secondary clinical response provided by the secondary therapeutic agent. Often, the coordinate administration of a compound of the invention with a secondary therapeutic agent as contemplated herein will yield an enhanced therapeutic response beyond the therapeutic response elicited by either or both the compound of the invention and/or secondary therapeutic agent alone.

In one embodiment, combination therapy involves alternating between administering a compound of the present invention and a second therapeutic agent (i.e., alternating therapy regimens between the two drugs, e.g., at one week, one month, three month, six month, or one year intervals). Alternating drug regimens in this context will often reduce or even eliminate adverse side effects, such as toxicity, that may attend long-term administration of one or both drugs alone.

In certain embodiments of the invention, the additional psychotherapeutic agent is an atypical antipsychotic, which in combination with (1R,5S)-(+)-1-(naphthalen-2-yl)-3-azabicyclo[3.1.0]hexane may be useful for treating conditions including, but not limited to, autism, treatment resistant depression, schizophrenia, bipolar disorder and personality disorders. Atypical antipsychotics that may be useful include, but are not limited to, aripiprazole, ziprasidone, risperidone, quetiepine, or olanzapine.

In other embodiments of combinatorial formulations and coordinate treatment methods provided herein, the secondary psychotherapeutic agent is an anti-depressant for treatment of conditions including, but not limited to, depression, difficult to treat depression, atypical depression, and treatment resistant depression. Examples of useful antidepressants include, but are not limited to, any species within the broad families of tri-cyclic antidepressants (TCAs) including, but not limited to, amitriptyline, imipramine, clomipramine, or desipramine; specific monoamine reuptake inhibitors; selective serotonin reuptake inhibitors (SSRIs) including, but not limited to, escitalopram, fluoxetine, fluvoxamine, sertraline, citalopram, vilazodone, and paroxetine; selective norepinephrine or noradrenaline reuptake inhibitors including but not limited to, tertiary amine tricyclics such as amitriptyline, clomipramine, doxepin, imipramine, (+)-trimipramine, and secondary amine tricyclics including amoxapine, desipramine, maprotiline, nortriptyline, and protriptyline; selective dopamine reuptake inhibitors; multiple monoamine reuptake inhibitors, e.g., that inhibit both serotonin and norepinephrine reuptake (SNRIs) including, but not limited to, venlafaxine, duloxetine, milnacipran, sibutramine, SEP-227162, LY 2216684, or inhibit both norepinephrine and dopamine, including but not limited to bupropion, amineptine, prolintane, dexmethylphenidate or pipradrol or those that inhibit both serotonin and dopamine; monoamine oxidase inhibitors (MAOIs); and indeterminate (atypical) antidepressants. In another embodiment, (1R,5S)-(+)-1-(naphthalen-2-yl)-3-azabicyclo[3.1.0]hexane or a pharmaceutically acceptable salt thereof may be used in combination with lithium for treatment of depressive disorders or bipolar disorder.

In additional embodiments of combinatorial formulations and coordinate treatment methods provided herein, the secondary psychotherapeutic agent may be an anticonvulsant including but not limited to gabopentin, pregabalin, lamotrigine, carbamazepine, oxcarbazepine, valproate, levetriacetam, and topiramate. Additional psychotherapeutic agents may additionally include opiate agonists including, but not limited to, buprenorphine, methadone and LAAM. Exemplary anxiolytics include, but are not limited to, buspirone, benzodiazepines, selective serotonin reuptake inhibitors, azapirones, barbiturates, hydroxyzine, and pregabalin.

In additional embodiments of combinatorial formulations and coordinate treatment methods provided herein, the secondary psychotherapeutic agent is an anti-addictive-disorder or anti-substance abuse agent. Examples of useful anti-addictive-disorder agents include, but are not limited to, tricyclic antidepressants; glutamate antagonists, such as ketamine HCl, dextromethorphan, dextrorphan tartrate and dizocilpine (MK801); degrading enzymes, such as anesthetics and aspartate antagonists; GABA agonists, such as baclofen and muscimol HBr; reuptake blockers; degrading enzyme blockers; glutamate agonists, such as D-cycloserine, carboxyphenylglycine, L-glutamic acid, and cis-piperidine-2,3-dicarboxylic acid; aspartate agonists; GABA antagonists such as gabazine (SR-95531), saclofen, bicuculline, picrotoxin, and (+) apomorphine HCl; and dopamine antagonists, such as spiperone HCl, haloperidol, and (−) sulpiride; anti-alcohol agents including, but not limited to, disulfiram and naltrexone; anti-nicotine agents including but not limited to, clonidine; anti-opiate agents including, but not limited to, methadone, clonidine, lofexidine, levomethadyl acetate HCl, naltrexone, and buprenorphine; anti-cocaine agents including, but not limited to, desipramine, amantadine, fluoxidine, and buprenorphine; anti-lysergic acid diethylamide ("anti-LSD") agent including but not limited to, diazepam; anti-1-(1-phenylcyclohexyl)piperidine ("anti-PCP") agent including, but not limited to, haloperidol.

In other embodiments of combinatorial formulations and coordinate treatment methods provided herein, the secondary therapeutic agent is an appetite suppressant. Examples of useful appetite suppressants include, but are not limited to, fenfluramine, phenylpropanolamine, bupropion, and mazindol.

In yet additional embodiments of combinatorial formulations and coordinate treatment methods provided herein, the secondary therapeutic agent is an anti-Parkinson's-disease agent. Examples of useful anti-Parkinson's-disease agents include, but are not limited to dopamine precursors, such as levodopa, L-phenylalanine, and L-tyrosine; neuroprotective agents; dopamine agonists; dopamine reuptake inhibitors; anticholinergics such as amantadine and memantine; and 1,3,5-trisubstituted adamantanes, such as 1-amino-3,5-dimethyl-adamantane. (See, U.S. Pat. No. 4,122,193).

In further embodiments of combinatorial formulations and coordinate treatment methods provided herein, the secondary therapeutic agent is an anti-inflammatory agent. Examples of useful anti-inflammatory agents included, but are not limited to celecoxib, ibuprofen, ketoprofen, naproxen sodium, piroxicam, sulindac, aspirin, and nabumetone.

Suitable routes of administration for a (1R,5S)-(+)-1-(naphthalen-2-yl)-3-azabicyclo[3.1.0]hexane or a pharmaceutically acceptable salt thereof as disclosed herein include, but are not limited to, oral, buccal, nasal, aerosol, topical, transdermal, mucosal, injectable, slow release, controlled release, iontophoresis, sonophoresis, and other conventional delivery routes, devices and methods. Injectable delivery methods are also contemplated, including but not limited to, intravenous, intramuscular, intraperitoneal, intraspinal, intrathecal, intracerebroventricular, intraarterial, and subcutaneous injection.

Suitable effective unit dosage amounts of a (1R,5S)-(+)-1-(naphthalen-2-yl)-3-azabicyclo[3.1.0]hexane or a pharmaceutically acceptable salt thereof of the invention for mammalian subjects may range from about 1 to about 1800 mg, about 10 to about 1800 mg, 25 to about 1800 mg, about 50 to about 1000 mg, about 75 to about 900 mg, about 100 to about 750 mg, or about 150 to about 500 mg. In certain embodiments, the effective dosage will be selected within narrower ranges of, for example, about 5 to about 10 mg, 10 to about 25 mg, about 30 to about 50 mg, about 10 to about 300 mg, about 25 to about 300 mg, about 50 to about 100 mg, about 100 to about 250 mg, or about 250 to about 500 mg. These and other effective unit dosage amounts may be administered in a single dose, or in the form of multiple daily, weekly or monthly doses, for example in a dosing regimen comprising from 1 to 4, or 2-3, doses administered per day, per week, or per month. In exemplary embodiments, dosages of about 10 to about 25 mg, about 30 to about 50 mg, about 25 to about 150, about 50 to about 100 mg, about 100 to about 250 mg, or about 250 to about 500 mg, are administered one, two, three, or four times per day. In more detailed embodiments, dosages of about 50-75 mg, about 100-200 mg, about 250-400 mg, or about 400-600 mg are administered once or twice daily. In further detailed embodiments, dosages of about 50-100 mg are administered twice daily. In alternate embodiments, dosages are calculated based on body weight, and may be administered, for example, in amounts from about 0.5 mg/kg to about 20 mg/kg per day, 1 mg/kg to about 15 mg/kg per day, 1 mg/kg to about 10 mg/kg per day, 2 mg/kg to about 20 mg/kg per day, 2 mg/kg to about 10 mg/kg per day or 3 mg/kg to about 15 mg/kg per day.

The amount, timing, and mode of delivery of compositions of the invention comprising an effective amount of a (1R,5S)-(+)-1-(naphthalen-2-yl)-3-azabicyclo[3.1.0]hexane or a pharmaceutically acceptable salt thereof will be routinely adjusted on an individual basis, depending on such factors as weight, age, gender, and condition of the individual, the acuteness of the condition to be treated and/or related symptoms, whether the administration is prophylactic or therapeutic, and on the basis of other factors known to effect drug delivery, absorption, pharmacokinetics, including half-life, and efficacy. An effective dose or multi-dose treatment regimen for the compounds of the invention will ordinarily be selected to approximate a minimal dosing regimen that is necessary and sufficient to substantially prevent or alleviate one or more symptom(s) of a neurological or psychiatric condition in the subject, as described herein. Thus, following administration of (1R,5S)-(+)-1-(naphthalen-2-yl)-3-azabicyclo[3.1.0]hexane or a pharmaceutically acceptable salt thereof of the invention according to the formulations and methods herein, test subjects will exhibit a 10%, 20%, 30%, 50% or greater reduction, up to a 75-90%, or 95% or greater, reduction, in one or more symptoms associated with a targeted monoamine neurotransmitter influenced disorder or other neurological or psychiatric condition, compared to placebo-treated or other suitable control subjects.

Pharmaceutical dosage forms of a compound of the present invention may optionally include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

Pharmaceutical dosage forms of (1R,5S)-(+)-1-(naphthalen-2-yl)-3-azabicyclo[3.1.0]hexane may include inorganic and organic acid addition salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; organic acid salts such as acetate, citrate, lactate, succinate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate, tartrate, gluconate and the like.

Within various combinatorial or coordinate treatment methods of the invention, the additional psychotherapeutic agent and (1R,5S)-(+)-1-(naphthalen-2-yl)-3-azabicyclo[3.1.0]hexane or a pharmaceutically acceptable salt thereof may each be administered by any of a variety of delivery routes and modes, which may be the same or different for each agent.

An additional psychotherapeutic compound and/or and (1R,5S)-(+)-1-(naphthalen-2-yl)-3-azabicyclo[3.1.0]hexane or a pharmaceutically acceptable salt thereof of the present invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets and capsules, which may be prepared by any conventional method of preparing pharmaceutical oral unit dosage forms can be utilized in preparing oral unit dosage forms. Oral unit dosage forms, such as tablets or capsules, may contain one or more conventional additional formulation ingredients, including, but not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants. The aforementioned effervescent agents and disintegrants are useful in the formulation of rapidly disintegrating tablets known to those skilled in the art. These typically disintegrate in the mouth in less than one minute, and preferably in less than thirty seconds. By effervescent agent is meant a couple, typically an organic acid and a carbonate or bicarbonate.

(1R,5S)-(+)-1-(naphthalen-2-yl)-3-azabicyclo[3.1.0] hexane or a pharmaceutically acceptable salt thereof of the invention can be prepared and administered in any of a variety of inhalation or nasal delivery forms known in the art. Devices capable of depositing aerosolized formulations of co-crystals of (1R,5S)-(+)-1-(naphthalen-2-yl)-3-azabicyclo[3.1.0]hexane or a pharmaceutically acceptable salt thereof of the invention in the sinus cavity or pulmonary alveoli of a patient include metered dose inhalers, nebulizers, dry powder generators, sprayers, and the like. Pulmonary delivery to the lungs for rapid transit across the alveolar epithelium into the blood stream may be particularly useful in treating impending episodes of depression. Methods and compositions suitable for pulmonary delivery of drugs for systemic effect are well known in the art. Suitable formulations, wherein the carrier is a liquid, for administration, as for example, a nasal spray or as nasal drops, may include aqueous or oily solutions of a compound of the present invention, and any additional active or inactive ingredient(s).

Intranasal delivery permits the passage of active compounds of the invention into the blood stream directly after administering an effective amount of the compound to the nose, without requiring the product to be deposited in the lung. In addition, intranasal delivery can achieve direct, or enhanced, delivery of the active (1R,5S)-(+)-1-(naphthalen-2-yl)-3-azabicyclo[3.1.0]hexane to the central nervous system. In these and other embodiments, intranasal administration of the compounds of the invention may be advantageous for treating disorders influenced by monoamine neurotransmitters, by providing for rapid absorption and delivery.

For intranasal and pulmonary administration, a liquid aerosol formulation will often contain an active compound of the invention combined with a dispersing agent and/or a physiologically acceptable diluent. Alternative, dry powder aerosol formulations may contain a finely divided solid form of the subject compound and a dispersing agent allowing for the ready dispersal of the dry powder particles. With either liquid or dry powder aerosol formulations, the formulation must be aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter, e.g., in a range of from about 2-5 microns, for nasal or pulmonary distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

Yet additional compositions and methods of the invention are provided for topical administration (1R,5S)-(+)-1-(naphthalen-2-yl)-3-azabicyclo[3.1.0]hexane or a pharmaceutically acceptable salt thereof of the present invention. Topical compositions may comprise a compound of the present invention and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise a compound of the present invention dissolved or dispersed in water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, e.g. structure or matrix, for sustaining the absorption of the drug over an extended period of time, for example 24 hours.

Yet additional formulations of a compound of the present invention are provided for parenteral administration, including aqueous and non-aqueous sterile injection solutions which may optionally contain anti-oxidants, buffers, bacteriostats and/or solutes which render the formulation isotonic with the blood of the mammalian subject; aqueous and non-aqueous sterile suspensions which may include suspending agents and/or thickening agents; dispersions; and emulsions. The formulations may be presented in unit-dose or multi-dose containers. Pharmaceutically acceptable formulations and ingredients will typically be sterile or readily sterilizable, biologically inert, and easily administered. Parenteral preparations typically contain buffering agents and preservatives, and may be lyophilized for reconstitution at the time of administration.

Parental formulations may also include polymers for extended release following parenteral administration. Such polymeric materials are well known to those of ordinary skill in the pharmaceutical compounding arts. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

Within exemplary compositions and dosage forms of the invention, (1R,5S)-(+)-1-(naphthalen-2-yl)-3-azabicyclo[3.1.0]hexane or a pharmaceutically acceptable salt thereof for treating disorders disclosed herein is administered in an extended release or sustained release formulation. In these formulations, the sustained release composition of the formulation provides therapeutically effective plasma levels (1R,5S)-(+)-1-(naphthalen-2-yl)-3-azabicyclo[3.1.0]hexane or a pharmaceutically acceptable salt thereof over a sustained delivery period of approximately 8 hours or longer, or over a sustained delivery period of approximately 18 hours or longer, up to a sustained delivery period of approximately 24 hours or longer.

In exemplary embodiments, (1R,5S)-(+)-1-(naphthalen-2-yl)-3-azabicyclo[3.1.0]hexane or a pharmaceutically acceptable salt thereof is combined with a sustained release vehicle, matrix, binder, or coating material. As used herein, the term "sustained release vehicle, matrix, binder, or coating material" refers to any vehicle, matrix, binder or coating material that effectively, significantly delays dissolution of the active compound in vitro, and/or delays, modifies, or extends delivery of the active compound into the blood stream (or other in vivo target site of activity) of a subject following administration (e.g., oral administration), in comparison to dissolution and/or delivery provided by an "immediate release" formulation, as described herein, of the same dosage amount of the active compound. Accordingly, the term "sustained release vehicle, matrix, binder, or coating material" as used herein is intended to include all such vehicles, matrices, binders and coating materials known in the art as "sustained release", "delayed release", "slow release", "extended release", "controlled release", "modified release", and "pulsatile release" vehicles, matrices, binders and coatings.

In one aspect, the current invention comprises an oral sustained release dosage composition for administering (1R,5S)-(+)-1-(naphthalen-2-yl)-3-azabicyclo[3.1.0]hexane or a pharmaceutically acceptable salt thereof. In a related aspect, the invention comprises a method of reducing one or more side effects that attend administration of an oral dosage form of (1R,5S)-(+)-1-(naphthalen-2-yl)-3-azabicyclo[3.1.0]hexane or a pharmaceutically acceptable salt thereof by employing a sustained release formulation. Within this method, following oral administration of (1R,5S)-(+)-1-(naphthalen-2-yl)-3-azabicyclo[3.1.0]hexane or a pharmaceutically acceptable salt thereof, the active agent is released in a sustained, delayed, gradual or modified release delivery mode into the gastrointestinal tract (e.g., the intestinal lumen) of the subject over a period of hours, during which the (1R,5S)-(+)-1-(naphthalen-2-yl)-3-azabicyclo[3.1.0]hexane or a pharmaceutically acceptable salt thereof reaches, and is sustained at, a therapeutic concentration in a blood plasma, tissue, organ or other target site of activity (e.g., a central nervous system tissue, fluid or compartment) in the patient. When following this method, the side effect profile of (1R,5S)-(+)-1-(naphthalen-2-yl)-3-azabicyclo[3.1.0]hexane or a pharmaceutically acceptable salt thereof is less than a side effect profile of an equivalent dose of (1R,5S)-(+)-1-(naphthalen-2-yl)-3-azabicyclo[3.1.0]hexane or a pharmaceutically acceptable salt thereof administered in an immediate release oral dosage form.

In certain embodiments, (1R,5S)-(+)-1-(naphthalen-2-yl)-3-azabicyclo[3.1.0]hexane or a pharmaceutically acceptable salt thereof is released from the sustained release compositions and dosage forms of the invention and delivered into the blood plasma or other target site of activity in the subject at a sustained therapeutic level over a period of at least about 6 hours, often over a period of at least about 8 hours, at least about 12 hours, or at least about 18 hours, and in other embodiments over a period of about 24 hours or greater. By sustained therapeutic level is meant a plasma concentration level of at least a lower end of a therapeutic dosage range as exemplified herein. In more detailed embodiments of the invention, the sustained release compositions and dosage forms will yield a therapeutic level of (1R,5S)-(+)-1-(naphthalen-2-yl)-3-azabicyclo[3.1.0]hexane or a pharmaceutically acceptable salt thereof following administration to a mammalian subject in a desired dosage amount (e.g., 5, 10, 25, 50, 100 200, 400, 600, or 800 mg) that yields a minimum plasma concentration of at least a lower end of a therapeutic dosage range as exemplified herein over a period of at least about 6 hours, at least about 8 hours, at least about 12 hours, at least about 18 hours, or up to 24 hours or longer. In alternate embodiments of the invention, the sustained release compositions and dosage forms will yield a therapeutic level (1R,5S)-(+)-1-(naphthalen-2-yl)-3-azabicyclo[3.1.0]hexane or a pharmaceutically acceptable salt thereof following administration to a mammalian subject in a desired dosage amount (e.g., 5, 10, 25, 50, 100, 200, 400, 600, or 800 mg) that yields a minimum plasma concentration that is known to be associated with clinical efficacy, over a period of at least about 6 hours, at least about 8 hours, at least about 12 hours, at least about 18 hours, or up to 24 hours or longer.

In certain embodiments, the (1R,5S)-(+)-1-(naphthalen-2-yl)-3-azabicyclo[3.1.0]hexane or a pharmaceutically acceptable salt thereof is released from the compositions and dosage forms of the invention and delivered into the blood plasma or other target site of activity in the subject (including, but not limited to, areas of the brain such as the prefrontal cortex, frontal cortex, thalamus, striatum, ventral tegmental area, other cortical areas, hippocampus, hypothalamus, or nucleus accumbens) in a sustained release profile characterized in that from about 0% to 20% of the active compound is released and delivered (as determined, e.g., by measuring blood plasma levels) within in 0 to 2 hours, from 20% to 50% of the active compound is released and delivered within about 2 to 12 hours, from 50% to 85% of the active compound is released and delivered within about 3 to 20 hours, and greater than 75% of the active compound is released and delivered within about 5 to 18 hours.

In more detailed embodiments of the invention, compositions and oral dosage forms of (1R,5S)-(+)-1-(naphthalen-2-yl)-3-azabicyclo[3.1.0]hexane or a pharmaceutically acceptable salt thereof are provided, wherein the compositions and dosage forms, after ingestion, provide a curve of concentration (1R,5S)-(+)-1-(naphthalen-2-yl)-3-azabicyclo[3.1.0]hexane or a pharmaceutically acceptable salt thereof agents over time, the curve having an area under the curve (AUC) which is approximately proportional to the dose (1R,5S)-(+)-1-(naphthalen-2-yl)-3-azabicyclo[3.1.0]hexane or a pharmaceutically acceptable salt thereof administered, and a maximum concentration (C max) that is proportional to the dose (1R,5S)-(+)-1-(naphthalen-2-yl)-3-azabicyclo[3.1.0]hexane or a pharmaceutically acceptable salt thereof administered.

In other detailed embodiments, the C max (1R,5S)-(+)-1-(naphthalen-2-yl)-3-azabicyclo[3.1.0]hexane or a pharmaceutically acceptable salt thereof provided after oral delivery of a composition or dosage form of the invention is less than about 80%, often less than about 75%, in some embodiments less than about 60%, or 50%, of a C max obtained after administering an equivalent dose of the active compound in an immediate release oral dosage form.

Within exemplary embodiments of the invention, the compositions and dosage forms containing (1R,5S)-(+)-1-(naphthalen-2-yl)-3-azabicyclo[3.1.0]hexane or a pharmaceutically acceptable salt thereof and a sustained release vehicle, matrix, binder, or coating will yield sustained delivery of the active compound such that, following administration of the composition or dosage form to a mammalian treatment subject, the C max of the (1R,5S)-(+)-1-(naphthalen-2-yl)-3-azabicyclo[3.1.0]hexane or a pharmaceutically acceptable salt thereof in the treatment subject is less than about 80% of a C max provided in a control subject after administration of the same amount of the (1R,5S)-(+)-1-(naphthalen-2-yl)-3-azabicyclo[3.1.0]hexane or a pharmaceutically acceptable salt thereof in an immediate release formulation.

As used herein, the term "immediate release dosage form" refers to a dosage form (1R,5S)-(+)-1-(naphthalen-2-yl)-3-azabicyclo[3.1.0]hexane or a pharmaceutically acceptable salt thereof wherein the active compound readily dissolves upon contact with a liquid physiological medium, for example phosphate buffered saline (PBS) or natural or artificial gastric fluid. In certain embodiments, an immediate release formulation will be characterized in that at least 70% of the active compound will be dissolved within a half hour after the dosage form is contacted with a liquid physiological medium. In alternate embodiments, at least 80%, 85%, 90% or more, or up to 100%, of the active compound in an immediate release dosage form will dissolve within a half hour following contact of the dosage form with a liquid physiological medium in an art-accepted in vitro dissolution assay. These general characteristics of an immediate release dosage form will often relate to powdered or granulated compositions (1R,5S)-(+)-1-(naphthalen-2-yl)-3-azabicyclo[3.1.0]hexane or a pharmaceutically acceptable salt thereof in a capsulated dosage form, for example in a gelatin-encapsulated dosage form, where dissolution will often be relatively immediate after dissolution/failure of the gelatin capsule. In alternate embodiments, the immediate release dosage form may be provided in the form of a compressed tablet, granular preparation, powder, or even liquid dosage form, in which cases the dissolution profile will often be even more immediate (e.g., wherein at least 85%-95% of the active compound is dissolved within a half hour).

In additional embodiments of the invention, an immediate release dosage form will include compositions wherein the (1R,5S)-(+)-1-(naphthalen-2-yl)-3-azabicyclo[3.1.0]hexane or a pharmaceutically acceptable salt thereof is not admixed, bound, coated or otherwise associated with a formulation component that substantially impedes in vitro or in vivo dissolution and/or in vivo bioavailability of the active compound. Within certain embodiments, (1R,5S)-(+)-1-(naphthalen-2-yl)-3-azabicyclo[3.1.0]hexane or a pharmaceutically acceptable salt thereof will be provided in an immediate release dosage form that does not contain significant amounts of a sustained release vehicle, matrix, binder or coating material. In this context, the term "significant amounts of a sustained release vehicle, matrix, binder or coating material" is not intended to exclude any amount of such materials, but an amount sufficient to impede in vitro or in vivo dissolution of an (1R,5S)-(+)-1-(naphthalen-2-yl)-3-azabicyclo[3.1.0]hexane or a pharmaceutically acceptable salt thereof in a formulation containing such materials by at least 5%, often at least 10%, and up to at least 15%-20% compared to dissolution of the (1R,5S)-(+)-1-(naphthalen-2-yl)-3-azabicyclo[3.1.0]hexane or a pharmaceutically acceptable salt thereof when provided in a composition that is essentially free of such materials.

In alternate embodiments of the invention, an immediate release dosage form (1R,5S)-(+)-1-(naphthalen-2-yl)-3-azabicyclo[3.1.0]hexane or a pharmaceutically acceptable salt thereof may be any dosage form comprising the active compound which fits the FDA Biopharmaceutics Classification System (BCS) Guidance definition (see, e.g., http://www.fda.gov/cder/OPS/BCS_guidance.htm) of a "high solubility substance in a rapidly dissolving formulation." In exemplary embodiments, an immediate release formulation of (1R,5S)-(+)-1-(naphthalen-2-yl)-3-azabicyclo[3.1.0]hexane or a pharmaceutically acceptable salt thereof according to this aspect of the invention will exhibit rapid dissolution characteristics according to BCS Guidance parameters, such that at least approximately 85% of the (1R,5S)-(+)-1-(naphthalen-2-yl)-3-azabicyclo[3.1.0]hexane or a pharmaceutically acceptable salt thereof in the formulation will go into a test solution within about 30 minutes at pH 1, pH 4.5, and pH 6.8.

The compositions, dosage forms and methods of the invention thus include novel tools for coordinate treatment of disorders involving monoamine neurotransmitters by providing for sustained release and/or sustained delivery of (1R,5S)-(+)-1-(naphthalen-2-yl)-3-azabicyclo[3.1.0]hexane or a pharmaceutically acceptable salt thereof. As used herein, "sustained release" and "sustained delivery" are evinced by a sustained, delayed, extended, or modified, in vitro or in vivo dissolution rate, in vivo release and/or delivery rate, and/or in vivo pharmacokinetic value(s) or profile.

The sustained release dosage forms of the present invention can take any form as long as one or more of the dissolution, release, delivery and/or pharmacokinetic property(ies) identified above are satisfied. Within illustrative embodiments, the composition or dosage form can comprise (1R,5S)-(+)-1-(naphthalen-2-yl)-3-azabicyclo[3.1.0]hexane or a pharmaceutically acceptable salt thereof combined with any one or combination of: a drug-releasing polymer, matrix, bead, microcapsule, or other solid drug-releasing vehicle; drug-releasing tiny timed-release pills or mini-tablets; compressed solid drug delivery vehicle; controlled release binder; multi-layer tablet or other multi-layer or multi-component dosage form; drug-releasing lipid; drug-releasing wax; and a variety of other sustained drug release materials as contemplated herein, or formulated in an osmotic dosage form.

The present invention thus provides a broad range of sustained release compositions and dosage forms comprising (1R,5S)-(+)-1-(naphthalen-2-yl)-3-azabicyclo[3.1.0] hexane or a pharmaceutically acceptable salt thereof, which in certain embodiments are adapted for providing sustained release of the active compound(s) following, e.g., oral administration. Sustained release vehicles, matrices, binders and coatings for use in accordance with the invention include any biocompatible sustained release material which is inert to the active agent and which is capable of being physically combined, admixed, or incorporated with the active compound. Useful sustained release materials may be dissolved, degraded, disintegrated, and/or metabolized slowly under physiological conditions following delivery (e.g., into a gastrointestinal tract of a subject, or following contact with gastric fluids or other bodily fluids). Useful sustained release materials are typically non-toxic and inert when contacted with fluids and tissues of mammalian subjects, and do not trigger significant adverse side effects such as irritation, immune response, inflammation, or the like. They are typically metabolized into metabolic products which are biocompatible and easily eliminated from the body.

In certain embodiments, sustained release polymeric materials are employed as the sustained release vehicle, matrix, binder, or coating (see, e.g., "Medical Applications of Controlled Release," Langer and Wise (eds.), CRC Press., Boca Raton, Fla. (1974); "Controlled Drug Bioavailability," Drug Product Design and Performance, Smolen and Ball (eds.), Wiley, N.Y. (1984); Ranger and Peppas, 1983, J Macromol. Sci. Rev. Macromol Chem. 23:61; see also Levy et al., 1985, Science 228: 190; During et al., 1989, Ann. Neurol. 25:351; Howard et al, 1989, J. Neurosurg. 71:105, each incorporated herein by reference). Within exemplary embodiments, useful polymers for co-formulating with (1R, 5S)-(+)-1-(naphthalen-2-yl)-3-azabicyclo[3.1.0]hexane or a pharmaceutically acceptable salt thereof to yield a sustained release composition or dosage form include, but are not limited to, ethylcellulose, hydroxyethyl cellulose; hydroxyethylmethyl cellulose; hydroxypropyl cellulose; hydroxypropylmethyl cellulose; hydroxypropylmethyl cellulose phthalate; hydroxypropylmethylcellulose acetate succinate; hydroxypropylmethylcellulose acetate phthalate; sodium carboxymethylcellulose; cellulose acetate phthalate; cellulose acetate trimellitate; polyoxyethylene stearates; polyvinyl pyrrolidone; polyvinyl alcohol; copolymers of polyvinyl pyrrolidone and polyvinyl alcohol; polymethacrylate copolymers; and mixtures thereof.

Additional polymeric materials for use as sustained release vehicles, matrices, binders, or coatings within the compositions and dosage forms of the invention include, but are not limited to, additional cellulose ethers, e.g., as described in Alderman, Int. J. Pharm. Tech. & Prod. Mfr., 1984, 5(3) 1-9 (incorporated herein by reference). Other useful polymeric materials and matrices are derived from copolymeric and homopolymeric polyesters having hydrolysable ester linkages. A number of these are known in the art to be biodegradable and to lead to degradation products having no or low toxicity. Exemplary polymers in this context include polyglycolic acids (PGAs) and polylactic acids (PLAs), poly(DL-lactic acid-co-glycolic acid)(DL PLGA), poly(D-lactic acid-coglycolic acid)(D PLGA) and poly(L-lactic acid-co-glycolic acid)(L PLGA). Other biodegradable or bioerodable polymers for use within the invention include such polymers as poly(s-caprolactone), poly(c-aprolactone-CO-lactic acid), poly($\varepsilon$-aprolactone-CO-glycolic acid), poly($\beta$-hydroxy butyric acid), poly(alkyl-2-cyanoacrilate), hydrogels such as poly(hydroxyethyl methacrylate), polyamides, poly-amino acids (e.g., poly-L-leucine, poly-glutamic acid, poly-L-aspartic acid, and the like), poly (ester ureas), poly (2-hydroxyethyl DL-aspartamide), polyacetal polymers, polyorthoesters, polycarbonates, polymaleamides, polysaccharides, and copolymers thereof. Methods for preparing pharmaceutical formulations using these polymeric materials are generally known to those skilled in the art (see, e.g., Sustained and Controlled Release Drug Delivery Systems, J. R. Robinson, ed., Marcel Dekker, Inc., New York, 1978, incorporated herein by reference).

In other embodiments of the invention, the compositions and dosage forms (1R,5S)-(+)-1-(naphthalen-2-yl)-3-azabicyclo[3.1.0]hexane or a pharmaceutically acceptable salt thereof coated on a polymer substrate. The polymer can be an erodible or a nonerodible polymer. The coated substrate may be folded onto itself to provide a bilayer polymer drug dosage form. For example (1R,5S)-(+)-1-(naphthalen-2-yl)-3-azabicyclo[3.1.0]hexane or a pharmaceutically acceptable salt thereof can be coated onto a polymer such as a polypeptide, collagen, gelatin, polyvinyl alcohol, polyorthoester, polyacetyl, or a polyorthocarbonate, and the coated polymer folded onto itself to provide a bilaminated dosage form. In operation, the bioerodible dosage form erodes at a controlled rate to dispense the active compound over a sustained release period. Representative biodegradable polymers for use in this and other aspects of the invention can be selected from, for example, biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly(dehydropyrans), and poly(dioxinones) which are known in the art (see, e.g., Rosoff, Controlled Release of Drugs, Chap. 2, pp. 53-95 (1989); and U.S. Pat. Nos. 3,811,444; 3,962,414; 4,066,747, 4,070,347; 4,079,038; and 4,093,709, each incorporated herein by reference).

In another embodiment of the invention, the dosage form comprises (1R,5S)-(+)-1-(naphthalen-2-yl)-3-azabicyclo [3.1.0]hexane or a pharmaceutically acceptable salt thereof loaded into a polymer that releases the drug by diffusion through a polymer, or by flux through pores or by rupture of a polymer matrix. The drug delivery polymeric dosage form comprises the active compound contained in or on the polymer. The dosage form comprises at least one exposed surface at the beginning of dose delivery. The non-exposed surface, when present, can be coated with a pharmaceutically acceptable material impermeable to the passage of a drug. The dosage form may be manufactured by procedures known in the art, for example by blending a pharmaceutically acceptable carrier like polyethylene glycol, with a pre-determined dose of the active compound(s) at an elevated temperature (e.g., 37° C.), and adding it to a silastic medical grade elastomer with a cross-linking agent, for example, octanoate, followed by casting in a mold. The step is repeated for each optional successive layer. The system is allowed to set for 1 hour, to provide the dosage form. Representative polymers for manufacturing such sustained release dosage forms include, but are not limited to, olefin, and vinyl polymers, addition polymers, condensation polymers, carbohydrate polymers, and silicon polymers as represented by polyethylene, polypropylene, polyvinyl acetate, polymethylacrylate, polyisobutylmethacrylate, poly alginate, polyamide and polysilicon. These polymers and procedures for manufacturing them have been described in the art (see, e.g., Coleman et al., Polymers 1990, 31, 1187-1231; Roerdink et al., Drug Carrier Systems 1989, 9, 57-10; Leong et al., Adv. Drug Delivery Rev. 1987, 1, 199-233; and Roff et al., Handbook of Common Polymers 1971, CRC Press; U.S. Pat. No. 3,992,518).

In other embodiments of the invention, the compositions and dosage forms comprise (1R,5S)-(+)-1-(naphthalen-2-yl)-3-azabicyclo[3.1.0]hexane or a pharmaceutically acceptable salt thereof incorporated with or contained in beads that on dissolution or diffusion release the active compound over an extended period of hours, for example over a period of at least 6 hours, over a period of at least 8 hours, over a period of at least 12 hours, or over a period of up to 24 hours or longer. The drug-releasing beads may have a central composition or core comprising (1R,5S)-(+)-1-(naphthalen-2-yl)-3-azabicyclo[3.1.0]hexane or a pharmaceutically acceptable salt thereof and a pharmaceutically acceptable carrier, along with one or more optional excipients such as a lubricants, antioxidants, dispersants, and buffers. The beads may be medical preparations with a diameter of about 1 to 2 mm. In exemplary embodiments they are formed of non-cross-linked materials to enhance their discharge from the gastrointestinal tract. The beads may be coated with a release rate-controlling polymer that gives a timed release pharmacokinetic profile. In alternate embodiments the beads may be manufactured into a tablet for therapeutically effective drug administration. The beads can be made into matrix tablets by direct compression of a plurality of beads coated with, for example, an acrylic resin and blended with excipients such as hydroxypropylmethyl cellulose. The manufacture and processing of beads for use within the invention is described in the art (see, e.g., Lu, Int. J. Pharm., 1994, 112, 117-124; Pharmaceutical Sciences by Remington, 14th ed, pp 1626-1628 (1970); Fincher, J. Pharm. Sci. 1968, 57, 1825-1835; and U.S. Pat. No. 4,083,949, each incorporated by reference) as has the manufacture of tablets (Pharmaceutical Sciences, by Remington, 17th Ed, Ch. 90, pp 1603-1625, 1985, incorporated herein by reference).

In another embodiment of the invention, the dosage form comprises a plurality of tiny pills or mini-tablets. The tiny pills or mini-tablets provide a number of individual doses for providing various time doses for achieving a sustained-release drug delivery profile over an extended period of time up to 24 hours. The tiny pills or mini-tablets may comprise a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, and a hydrophilic colloid. The hydrophilic polymer may be formed into a plurality (e.g., 4 to 50) tiny pills or mini-tablet, wherein each tiny pill or mini-tablet comprises a pre-determined dose (1R,5S)-(+)-1-(naphthalen-2-yl)-3-azabicyclo[3.1.0]hexane or a pharmaceutically acceptable salt thereof, e.g., a dose of about 10 ng, 0.5 mg, 1 mg, 1.2 mg, 1.4 mg, 1.6 mg, 5.0 mg etc. The tiny pills and mini-tablets may further comprise a release rate-controlling wall of 0.001 up to 10 mm thickness to provide for timed release of the active compound. Representative wall forming materials include a triglyceryl ester selected from the group consisting of glyceryl tristearate, glyceryl monostearate, glyceryl dipalmitate, glyceryl laureate, glyceryl didecenoate and glyceryl tridenoate. Other wall forming materials comprise polyvinyl acetate, phthalate, methylcellulose phthalate and microporous olefins. Procedures for manufacturing tiny pills and mini-tablets are known in the art (see, e.g., U.S. Pat. Nos. 4,434,153; 4,721,613; 4,853,229; 2,996,431; 3,139,383 and 4,752,470, each incorporated herein by reference). The tiny pills and mini-tablets may further comprise a blend of particles, which may include particles of different sizes and/or release properties, and the particles may be contained in a hard gelatin or non-gelatin capsule or soft gelatin capsule.

In yet another embodiment of the invention, drug-releasing lipid matrices can be used to formulate therapeutic compositions and dosage forms comprising (1R,5S)-(+)-1-(naphthalen-2-yl)-3-azabicyclo[3.1.0]hexane or a pharmaceutically acceptable salt thereof. In one exemplary embodiment, solid microparticles of the active compound are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700 (each incorporated herein by reference). The lipid-coated particles can optionally be compressed to form a tablet. Another controlled release lipid-based matrix material which is suitable for use in the sustained release compositions and dosage forms of the invention comprises polyglycolized glycerides, e.g., as described in Roussin et al., U.S. Pat. No. 6,171,615 (incorporated herein by reference).

In other embodiments of the invention, drug-releasing waxes can be used for producing sustained release compositions and dosage forms comprising (1R,5S)-(+)-1-(naphthalen-2-yl)-3-azabicyclo[3.1.0]hexane or a pharmaceutically acceptable salt thereof. Examples of suitable sustained drug-releasing waxes include, but are not limited to, carnauba wax, candedilla wax, esparto wax, ouricury wax, hydrogenated vegetable oil, bees wax, paraffin, ozokerite, castor wax, and mixtures thereof (see, e.g., Cain et al., U.S. Pat. No. 3,402,240; Shtohryn et al. U.S. Pat. No. 4,820,523; and Walters, U.S. Pat. No. 4,421,736, each incorporated herein by reference).

In still another embodiment, osmotic delivery systems are used for sustained release delivery of (1R,5S)-(+)-1-(naphthalen-2-yl)-3-azabicyclo[3.1.0]hexane or a pharmaceutically acceptable salt thereof (see, e.g., Verma et al., Drug Dev. Ind. Pharm., 2000, 26:695-708, incorporated herein by reference). In one exemplary embodiment, the osmotic delivery system is an OROS® system (Alza Corporation, Mountain View, Calif) and is adapted for oral sustained release delivery of drugs (see, e.g., U.S. Pat. Nos. 3,845,770; and 3,916,899, each incorporated herein by reference).

In another embodiment of the invention, the dosage form comprises an osmotic dosage form, which comprises a semi-permeable wall that surrounds a therapeutic composition comprising (1R,5S)-(+)-1-(naphthalen-2-yl)-3-azabicyclo[3.1.0]hexane or a pharmaceutically acceptable salt thereof. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained prodrug release. These delivery platforms can provide an essentially zero order delivery profile as opposed to the spiked profiles of immediate release formulations.

In alternate embodiments of the invention, the dosage form comprises another osmotic dosage form comprising a wall surrounding a compartment, the wall comprising a semipermeable polymeric composition permeable to the passage of fluid and substantially impermeable to the passage of the active compound present in the compartment, a drug-containing layer composition in the compartment, a hydrogel push layer composition in the compartment comprising an osmotic formulation for imbibing and absorbing fluid for expanding in size for pushing the (1R,5S)-(+)-1-(naphthalen-2-yl)-3-azabicyclo[3.1.0]hexane or a pharmaceutically acceptable salt thereof composition layer from the dosage form, and at least one passageway in the wall for releasing the drug composition. This osmotic system delivers the active compound by imbibing fluid through the semipermeable wall at a fluid imbibing rate determined by the permeability of the semipermeable wall and the osmotic pressure across the semipermeable wall causing the push layer to expand, thereby delivering the active compound through the exit passageway to a patient over a prolonged period of time (up to 24 or even 30 hours). The hydrogel layer composition may comprise 10 mg to 1000 mg of a hydrogel such as a member selected from the group consisting of a polyalkylene oxide of 1,000,000 to 8,000,000 which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer may comprise a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose), an osmagent, e.g., selected from the group consisting of sodium chloride, potassium chloride, potassium acid phosphate, tartaric acid, citric acid, raffinose, magnesium sulfate, magnesium chloride, urea, inositol, sucrose, glucose and sorbitol, and other agents such a hydroxypropylalkylcellulose of 9,000 to 225,000 average-number molecular weight (e.g., hydroxypropylethylcellulose, hydroxypropypentylcellulose, hydroxypropylmethylcellulose, or hydropropylbutylcellulose), ferric oxide, antioxidants (e.g., ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, dibutylphenol, vitamin E, lecithin and ethanolamine), and/or lubricants (e.g., calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid).

In the osmotic dosage forms, the semipermeable wall comprises a composition that is permeable to the passage of fluid and impermeable to passage of the (1R,5S)-(+)-1-(naphthalen-2-yl)-3-azabicyclo[3.1.0]hexane or a pharmaceutically acceptable salt thereof. The wall is nontoxic and comprises a polymer selected from the group consisting of a cellulose acylate, cellulose diacylate, cellulose triacylate, cellulose acetate, cellulose diacetate and cellulose triacetate. The wall typically comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether (e.g., hydroxypropylcellulose or a hydroxypropylalkycellulose such as hydroxypropylmethylcellulose). The total weight percent of all components comprising the wall is equal to 100 wt %. The internal compartment comprises the drug-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of drug to a patient over time. The dosage form comprises a passageway in the wall that connects the exterior of the dosage form with the internal compartment. The osmotic powered dosage form delivers the (1R,5S)-(+)-1-(naphthalen-2-yl)-3-azabicyclo[3.1.0] hexane or a pharmaceutically acceptable salt thereof from the dosage form to the patient at a zero order rate of release over a period of up to about 24 hours. As used herein, the expression "passageway" comprises means and methods suitable for the metered release of (1R,5S)-(+)-1-(naphthalen-2-yl)-3-azabicyclo[3.1.0]hexane or a pharmaceutically acceptable salt thereof from the compartment of an osmotic dosage form. The exit means comprises at least one passageway, including orifice, bore, aperture, pore, porous element, hollow fiber, capillary tube, channel, porous overlay, or porous element that provides for the osmotic controlled release of the active compound. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916, 899; 4,063,064; 4,088,864; 4,816,263; 4,200,098; and 4,285,987 (each incorporated herein by reference).

In more detailed embodiments, a compound of the present invention may be encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions.

A variety of methods is known by which (1R,5S)-(+)-1-(naphthalen-2-yl)-3-azabicyclo[3.1.0]hexane or a pharmaceutically acceptable salt thereof can be encapsulated in the form of microparticles, for example using by encapsulating the active compound within a biocompatible, biodegradable wall-forming material (e.g., a polymer)—to provide sustained or delayed release of the active compound. In these methods, the active compound is typically dissolved, dispersed, or emulsified in a solvent containing the wall forming material. Solvent is then removed from the microparticles to form the finished microparticle product. Examples of conventional microencapsulation processes are disclosed, e.g., in U.S. Pat. Nos. 3,737,337; 4,389,330; 4,652,441; 4,917,893; 4,677,191; 4,728,721; 5,407,609; 5,650,173; 5,654,008; and 6,544,559 (each incorporated herein by reference). These documents disclose methods that can be readily implemented to prepare microparticles containing (1R,5S)-(+)-1-(naphthalen-2-yl)-3-azabicyclo[3.1.0]hexane or a pharmaceutically acceptable salt thereof in a sustained release formulation according to the invention. As explained, for example, in U.S. Pat. No. 5,650,173, by appropriately selecting the polymeric materials, a microparticle formulation can be made in which the resulting microparticles exhibit both diffusional release and biodegradation release properties. For a diffusional mechanism of release, the active agent is released from the microparticles prior to substantial degradation of the polymer. The active agent can also be released from the microparticles as the polymeric excipient erodes. In addition, U.S. Pat. No. 6,596,316 (incorporated herein by reference) discloses methods for preparing microparticles having a selected release profile for fine tuning a release profile of an active agent from the microparticles.

In another embodiment of the invention, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release). Enteric coatings may function as a means for mediating sustained release of (1R,5S)-(+)-1-(naphthalen-2-yl)-3-azabicyclo[3.1.0]hexane or a pharmaceutically acceptable salt thereof by providing one or more barrier layers, which may be located entirely surrounding the active compound, between layers of a multi-layer solid dosage form (see below), and/or on one or more outer surfaces of one or multiple layers of a multi-layer solid dosage form (e.g., on end faces of layers of a substantially cylindrical tablet). Such barrier layers may, for example, be composed of polymers which are either substantially or completely impermeable to water or aqueous media, or are slowly erodible in water or aqueous media or biological liquids and/or which swell in contact with water or aqueous media. Suitable polymers for use as a barrier layer include acrylates, methacrylates, copolymers of acrylic acid, celluloses and derivatives thereof such as ethylcelluloses, cellulose acetate propionate, polyethylenes and polyvinyl alcohols etc. Barrier layers comprising polymers which swell in contact with water or aqueous media may swell to such an extent that the swollen layer forms a relatively large swollen mass, the size of which delays its immediate discharge from the stomach into the intestine. The barrier layer may itself contain active material content, for example the barrier layer may be a slow or delayed release layer. Barrier layers may typically have an individual thickness of 10 microns up to 2 mm. Suitable polymers for barrier layers which are relatively impermeable to water include the Methocel™ series of polymers, used singly or combined, and Ethocel™ polymers. Such polymers may suitably be used in combination with a plasticizer such as hydrogenated castor oil. The barrier layer may also include conventional binders, fillers, lubricants and compression acids etc such as Polyvidon K30 (trade mark), magnesium stearate, and silicon dioxide.

Additional enteric coating materials for mediating sustained release (1R,5S)-(+)-1-(naphthalen-2-yl)-3-azabicyclo[3.1.0]hexane or a pharmaceutically acceptable salt thereof include coatings in the form of polymeric membranes, which may be semipermeable, porous, or asymmetric membranes (see, e.g., U.S. Pat. No. 6,706,283, incorporated herein by reference). Coatings of these and other types for use within the invention may also comprise at least one delivery port, or pores, in the coating, e.g., formed by laser drilling or erosion of a plug of water-soluble material. Other useful coatings within the invention including coatings that rupture in an environment of use (e.g., a gastrointestinal compartment) to form a site of release or delivery port. Exemplary coatings within these and other embodiments of the invention include poly(acrylic) acids and esters; poly (methacrylic) acids and esters; copolymers of poly(acrylic) and poly(methacrylic) acids and esters; cellulose esters; cellulose ethers; and cellulose ester/ethers.

Additional coating materials for use in constructing solid dosage forms to mediate sustained release of (1R,5S)-(+)-1-(naphthalen-2-yl)-3-azabicyclo[3.1.0]hexane or a pharmaceutically acceptable salt thereof include, but are not limited to, polyethylene glycol, polypropylene glycol, copolymers of polyethylene glycol and polypropylene glycol, poly(vinylpyrrolidone), ethyl cellulose, hydroxyethyl cellulose, hydroxypropyl cellulose, carboxymethyl cellulose, carboxymethylethyl cellulose, starch, dextran, dextrin, chitosan, collagen, gelatin, bromelain, cellulose acetate, unplasticized cellulose acetate, plasticized cellulose acetate, reinforced cellulose acetate, cellulose acetate phthalate, cellulose acetate trimellitate, hydroxypropylmethylcellulose, hydroxypropylmethyl-cellulose phthalate, hydroxypropylmethylcellulose acetate succinate, hydroxypropylmethylcellulose acetate trimellitate, cellulose nitrate, cellulose diacetate, cellulose triacetate, agar acetate, amylose triacetate, beta glucan acetate, beta glucan triacetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate propionate, cellulose acetate p-toluene sulfonate, triacetate of locust gum bean, cellulose acetate with acetylated hydroxyethyl cellulose, hydroxlated ethylene-vinylacetate, cellulose acetate butyrate, polyalkenes, polyethers, polysulfones, polyethersulfones, polystyrenes, polyvinyl halides, polyvinyl esters and ethers, natural waxes and synthetic waxes.

In additional embodiments of the invention, sustained release (1R,5S)-(+)-1-(naphthalen-2-yl)-3-azabicyclo[3.1.0]hexane or a pharmaceutically acceptable salt thereof is provided by formulating the active compound in a dosage form comprising a multi-layer tablet or other multi-layer or multi-component dosage form. In exemplary embodiments, the active compound is formulated in layered tablets, for example having a first layer which is an immediate release layer and a second layer which is a slow release layer. Other multi-layered dosage forms of the invention may comprise a plurality of layers of compressed active ingredient having variable (i.e., selectable) release properties selected from immediate, extended and/or delayed release mechanisms. Multi-layered tablet technologies useful to produce sustained release dosage forms of (1R,5S)-(+)-1-(naphthalen-2-yl)-3-azabicyclo[3.1.0]hexane or a pharmaceutically acceptable salt thereof are described, for example, in International Publications WO 95/20946; WO 94/06416; and WO 98/05305 (each incorporated herein by reference). Other multi-component dosage forms for providing sustained delivery (1R,5S)-(+)-1-(naphthalen-2-yl)-3-azabicyclo[3.1.0]hexane or a pharmaceutically acceptable salt thereof include tablet formulations having a core containing the active compound coated with a release retarding agent and surrounded by an outer casing layer (optionally containing the active compound) (see, e.g., International Publication WO 95/28148, incorporated herein by reference). The release retarding agent is an enteric coating, so that there is an immediate release of the contents of the outer core, followed by a second phase from the core which is delayed until the core reaches the intestine. Additionally, International Publication WO 96/04908 (incorporated herein by reference) describes tablet formulations which comprise an active agent in a matrix, for immediate release, and granules in a delayed release form comprising the active agent. Such granules are coated with an enteric coating, so release is delayed until the granules reach the intestine. International Publication WO 96/04908 (incorporated herein by reference) describes delayed or sustained release formulations formed from granules which have a core comprising an active agent, surrounded by a layer comprising the active agent.

Another useful multi-component (bi-layer tablet) dosage form for sustained delivery of (1R,5S)-(+)-1-(naphthalen-2-yl)-3-azabicyclo[3.1.0]hexane or a pharmaceutically acceptable salt thereof is described in U.S. Pat. No. 6,878,386 (incorporated herein by reference). Briefly, the bilayer tablet comprises an immediate release and a slow release layer, optionally with a coating layer. The immediate release layer may be, for example, a layer which disintegrates immediately or rapidly and has a composition similar to that of known tablets which disintegrate immediately or rapidly. An alternative type of immediate release layer may be a swellable layer having a composition which incorporates polymeric materials which swell immediately and extensively in contact with water or aqueous media, to form a water permeable but relatively large swollen mass. Active material content may be immediately leached out of this mass. The slow release layer may have a composition comprising (1R,5S)-(+)-1-(naphthalen-2-yl)-3-azabicyclo[3.1.0]hexane or a pharmaceutically acceptable salt thereof with a release retarding vehicle, matrix, binder, coating, or excipient which allows for slow release of the active compound. Suitable release retarding excipients include pH sensitive polymers, for instance polymers based upon methacrylic acid copolymers, which may be used either alone or with a plasticiser; release-retarding polymers which have a high degree of swelling in contact with water or aqueous media such as the stomach contents; polymeric materials which form a gel on contact with water or aqueous media; and polymeric materials which have both swelling and gelling characteristics in contact with water or aqueous media. Release retarding polymers which have a high degree of swelling include, inter alia, cross-linked sodium carboxymethylcellulose, cross-linked hydroxypropylcellulose, high-molecular weight hydroxypropylmethylcellulose, carboxymethylamide, potassium methacrylatedivinylbenzene co-polymer, polymethylmethacrylate, cross-linked polyvinylpyrrolidone, high-molecular weight polyvinylalcohols etc. Release retarding gellable polymers include methylcellulose, carboxymethylcellulose, low-molecular weight hydroxypropylmethylcellulose, low-molecular weight polyvinylalcohols, polyoxyethyleneglycols, non-cross linked polyvinylpyrrolidone, xanthan gum etc. Release retarding polymers simultaneously possessing swelling and gelling properties include medium-viscosity hydroxypropylmethylcellulose and medium-viscosity polyvinylalcohols. An exemplary release-retarding polymer is xanthan gum, in particular a fine mesh grade of xanthan gum, preferably pharmaceutical grade xanthan gum, 200 mesh, for instance the product Xantural 75 (also known as Keltrol CR™ Monsanto, 800 N Lindbergh Blvd, St Louis, Mo. 63167, USA). Xanthan gum is a polysaccharide which upon hydration forms a viscous gel layer around the tablet through which the active has to diffuse. It has been shown that the smaller the particle size, the slower the release rate. In addition, the rate of release of active compound is dependent upon the amount of xanthan gum used and can be adjusted to give the desired profile. Examples of other polymers which may be used within these aspects of the invention include Methocel K4M™, Methocel E5™, Methocel E5O™, Methocel E4M™, Methocel K15M™ and Methocel K100M™. Other known release-retarding polymers which may be incorporated within this and other embodiments of the invention to provide a sustained release composition or dosage form of (1R,5S)-(+)-1-(naphthalen-2-yl)-3-azabicyclo[3.1.0]hexane or a pharmaceutically acceptable salt thereof include, hydrocolloids such as natural or synthetic gums, cellulose derivatives other than those listed above, carbohydrate-based substances such as acacia, gum tragacanth, locust bean gum, guar gum, agar, pectin, carrageenan, soluble and insoluble alginates, carboxypolymethylene, casein, zein, and the like, and proteinaceous substances such as gelatin.

Within other embodiments of the invention, a sustained release delivery device or system is placed in the subject in proximity of the target of the active compound, thus requiring only a fraction of the systemic dose (see, e.g., Goodson, in "Medical Applications of Controlled Release," supra, vol. 2, pp. 115-138, 1984; and Langer, 1990, Science 249:1527-1533, each incorporated herein by reference). In other embodiments, an oral sustained release pump may be used (see, e.g., Langer, supra; Sefton, 1987, CRC Crit. Ref. Biomed. Eng. 14:201; and Saudek et al., 1989, N. Engl. J. Med. 321:574, each incorporated herein by reference).

The pharmaceutical compositions and dosage forms of the current invention will typically be provided for administration in a sterile or readily sterilizable, biologically inert, and easily administered form.

In other embodiments the invention provides pharmaceutical kits for reducing symptoms in a human subject suffering from a disorder affected by monoamine neurotransmitters, including depression. The kits comprise (1R,5S)-(+)-1-(naphthalen-2-yl)-3-azabicyclo[3.1.0]hexane or a pharmaceutically acceptable salt thereof in an effective amount, and a container means for containing (1R,5S)-(+)-1-(naphthalen-2-yl)-3-azabicyclo[3.1.0]hexane or a pharmaceutically acceptable salt thereof for coordinate administration to the said subject (for example a container, divided bottle, or divided foil pack). The container means can include a package bearing a label or insert that provides instructions for multiple uses of the kit contents to treat the disorder and reduce symptoms in the subject. In more detailed embodiments, the (1R,5S)-(+)-1-(naphthalen-2-yl)-3-azabicyclo[3.1.0]hexane or a pharmaceutically acceptable salt thereof is admixed or co-formulated in a single, combined dosage form, for example a liquid or solid oral dosage form. In alternate embodiments, the (1R,5S)-(+)-1-(naphthalen-2-yl)-3-azabicyclo[3.1.0]hexane or a pharmaceutically acceptable salt thereof is contained in the kit in separate dosage forms for coordinate administration. An example of such a kit is a so-called blister pack. Blister packs are well-known in the packaging industry and are widely used for the packaging of pharmaceutical dosage forms (tablets, capsules and the like).

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list.

It is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The following examples illustrate certain aspects of the invention, but are not intended to limit in any manner the scope of the invention.

Example I

Preparation of (1R,5S)-(+)-1-(naphthalen-2-yl)-3-azabicyclo[3.1.0]hexane (1R,5 S)-(+)-1-(naphthalen-2-yl)-3-azabicyclo[3.1.0] hexane may be prepared as follows:

Step 1: Synthesis of [(1S,2R)-2-(aminomethyl)-2-(2-naphthyl)cyclopropyl]methan-1-ol, p-toluene-sulfonic Acid Salt 500 g (2.99 mol, 1.0 eq) of 2-naphthylacetonitrile was charged to a 12 L 3-neck round bottom flask equipped with overhead stirrer, addition funnel, thermocouple, nitrogen inlet, cooling bath and drying tube. 3.0 L of tetrahydrofuran was added and stirred at room temperature to dissolve all solids. 360 g (3.89 mol, 1.30 eq) (S)-(+)-epichlorohydrin was added and then the solution was cooled to an internal temperature of −25° C. 3.0 L of a 2 molar solution of sodium bis(trimethylsilyl)amide in tetrahydrofuran (6.00 mol, 2.0 eq) was added to the reaction mixture via addition funnel at a rate such that the internal temperature of the reaction mixture is maintained at less than −15° C. After completion of the addition, the mixture was stirred at between −20° C. and −14° C. for 2 hours 15 minutes. Borane-dimethylsulfide complex (750 mL of a 10.0 molar solution, 7.5 mol, 2.5 eq) was then slowly added to the reaction mixture at a rate such that the internal temperature was maintained at less than −5° C. Upon completion of the borane-dimethylsulfide addition the reaction mixture was heated to an internal temperature of 60° C. and stirred overnight at this temperature. Additional borane-dimethylsulfide complex (75 mL, 0.75 mol, 0.25 eq) was then added and the reaction mixture stirred at 60° C. for 1 hour 45 minutes. The reaction mixture was cooled to room temperature and then quenched by slow addition into pre-cooled (3° C.) 2 molar aqueous hydrochloric acid (5.76 L, 11.5 mol, 3.8 eq) at a rate such that the temperature of the quench solution was maintained at less than 22° C. The two phase mixture was then heated at an internal temperature of 50° C. for 1 hour followed by cooling to RT. Isopropyl acetate (2.0 L) and water (2.5 L) were added, the mixture agitated, and then the layers were allowed to settle. The upper organic layer was discarded. Aqueous ammonia (750 mL) was added to the aqueous layer which was then extracted with isopropylacetate (2.5 L). The aqueous layer was extracted with isopropylacetate (2.5 L) a second time. The organic extracts were combined and then sequentially washed with a 5% solution of sodium dibasic phosphate in water (2.0 L) followed by saturated brine (2.0 L). The organic layer was then concentrated to a total volume of 5.0 L and then heated to 50° C. para-Toluene sulfonic acid monohydrate (541 g, 2.84 mol) was then added in portions. During the addition white solids precipitated and a mild exotherm was observed. Upon completion of the addition the mixture was allowed to cool to RT and the solids collected by filtration. The filtercake was washed twice with isopropylacetate, 1.0 L each wash. The filtercake was then dried to a constant weight to give 664.3 g (55% yield) of the desired product as a white solid.

Step 2: Synthesis of (5S,1R)-1-(2-naphthyl)-3-azabicyclo[3.1.0]hexane HCl Salt

The amine-tosylate salt from step 1 (2037.9 g, 5.10 mol) was suspended in isopropylacetate (13.2 L) to give a white slurry in a 50 L 3-neck RB equipped with an overhead stirrer, thermocouple, addition funnel, nitrogen inlet and drying tube. Thionylchloride (445 mL, 6.12 mol, 1.20 eq) was then added via addition funnel over one hour 5 minutes. The maximum internal temperature was 24° C. After stirring for 4 hours 15 minutes 5 molar aqueous sodium hydroxide (6.1 L, 30.5 mol, 5.98 eq) was added via addition funnel at a rate such that the maximum internal temperature was 30° C. The mixture was then stirred for one hour 15 minutes after which the layers were allowed to settle and the layers were separated. The organic layer was washed with 1 molar aqueous sodium hydroxide (2.1 L). The aqueous layers were then combined and back extracted with isopropyl acetate (7.6 L). The organic layers were combined and washed with saturated aqueous brine (4.1 L). The organic layer was then dried over magnesium sulfate, filtered to remove solids, and then concentrated to a total volume of 4.2 L in vacuo. Hydrogen chloride in isopropyl alcohol (5.7N, 0.90 L, 5.13 mol, 1 eq) was then added over 50 minutes using an external water/ice bath to keep the internal temperature less than 30° C. After stirring for 45 minutes the solids were collected by filtration and the filtercake washed two times with isopropyl acetate, 2.3 L each wash. The filtercake was then partially dried and then taken forward to step 3 as a wetcake.

Step 3: Crude (5S,1R)-1(2-naphthyl)-3-azabicyclo [3.1.0]hexane HCl Salt Hot Slurry in Isopropyl Alcohol The wetcakes from two separate runs of step 2 (total of 4646.6 g starting amine tosylate salt) were combined and suspended in isopropyl alcohol (34.6 L) in a 50 L 3-neck round bottom flask equipped with overhead stirrer, heating mantel, thermocouple, reflux condenser, nitrogen inlet, and drying tube. The slurry was then heated to reflux, stirred for three hours at reflux, and then allowed to cool to room temperature. The solids were collected by filtration and the filtercake washed twice with isopropyl alcohol, 6.9 L each wash. The filtercake was then dried to a constant weight to give 2009.2 g of (5S,1R)-1-(2-naphthyl)-3-azabicyclo [3.1.0]hexane HCl salt (70% yield from 4646.6 g of amine tosylate salt).

Step 4: Recrystallization of (5S,11-(2-naphthyl)-3-azabicyclo[3.1.0]hexane HCl Salt from Ethanol to Upgrade the Enantiomeric Excess The (5S,1R)-1-(2-naphthyl)-3-azabicyclo[3.1.0]hexane HCl salt from step 3 (2009.2 g, 8.18 mol) was charged to a 50 L 3-neck round bottom flask equipped with an overhead stirrer, heating mantel, reflux condenser, nitrogen inlet, thermocouple, and drying tube. Ethanol (21.5 L of special industrial) was then added and the mixture heated to reflux to dissolve all solids. After dissolution of solids heating was discontinued and the mixture was allowed to cool to room temperature during which time solids reformed. The solids were then collected by filtration and the filtercake washed with ethanol (4.3 L). The filtercake was then dried to a constant weight to give 1434.6 g (71% yield) of recrystallized (5S,1R)-1-(2-naphthyl)-3-azabicyclo[3.1.0]hexane HCl salt. Chiral HPLC assay showed an enantiomeric excess of >99.5%.

Step 5: Rework to Improve Color Profile (5S,1R)-1-(2-naphthyl)-3-azabicyclo[3.1.0]hexane HCl (1405.6 g, 5.72 mol) was charged to a 22 L 3-neck round bottom flask equipped with overhead stirrer, heating mantel, thermocouple, nitrogen inlet and drying tube. Water (14.0 L) was added and the mixture heated to 34° C. to dissolve all solids. The solution was then transferred to a large separatory funnel and tetrahydrofuran (2.8 L) followed by isopropyl acetate (2.8 L) was added. The two phase mixture was agitated and the layers were then allowed to settle. The upper organic layer was discarded. Aqueous ammonia (1.14 L) was then added and the aqueous layer extracted with iso-propylacetate (14.0 L). The organic layer was dried over magnesium sulfate, filtered, and concentrated in vacuo to give an off-white solid. The solid was dissolved in isopropyl alcohol (14.0 L) and transferred to a 22 L 3-neck round bottom flask equipped with overhead stirrer, thermocouple, addition funnel, nitrogen inlet and drying tube. Hydrogen chloride in isopropyl alcohol (5.7 N, 175 mL, 1.0 mol) was then added over 10 minutes. Near the end of this addition the formation of solids was evident. The slurry was stirred for 30 minutes then additional hydrogen chloride in isopropanol (840 mL, 4.45 mol) was added over 65 minutes keeping the internal temperature less than 25° C. The solids were collected by filtration and the filtercake washed twice with isopropyl alcohol, 2.8 L each wash. The filtercake was then dried to a constant weight to give 1277.1 g (91% yield) of the product as an off-white solid.

Example II

Inhibition of Monoamine Uptake by (1R,5S)-(+)-1-(naphthalen-2-yl)-3-azabicyclo[3.1.0]hexane The ability of (1R,5S)-(+)-1-(naphthalen-2-yl)-3-azabicyclo[3.1.0]hexane for inhibiting transport of norepinephrine (NE) and/or dopamine (DA) and/or serotonin (5-HT) was evaluated using cell lines (such as the HEK 293 cell line) that stably express recombinant human NE, DA, and 5-HT transporters, respectively. Techniques for stably transfecting mammalian cell lines with neurotransmitter transporters and measuring the effects of drugs on amine uptake have been described in the literature (e.g., Eshleman A J, J Pharmacol Exp Ther 289:877-885, 1999) and are well known to those skilled in the art Monoamine uptake was determined in MDCK, CHO-K1, and HEK-293 cell lines respectively transfected with NE, DA, and 5-HT uptake transporters by MDS Pharma Services (Taipei, Taiwan 112, R. O. C.). The cells were incubated in 5 mM Tris-HCl, and 7.5 mM HEPES buffer, pH 7.1, containing 120 mM NaCl, 5.4 mM KCl, 1.2 mM $CaCl_2$, 1.2 mM $MgSO_4$, 5 mM D-glucose, and 1 mM Ascorbic Acid. The cellular homogenates were incubated with radioligands and various concentrations of drugs for 10 minutes at 25° C. The [$^3$H]-radioligands incorporated into the cells were determined according to published methods using liquid scintillation counting (Perovic and Müller 1995; Eshleman et al., 1999).

The results of these assays are shown in Table 1, below, which indicates the $IC_{50}$ value, defined as that concentration of compound necessary to inhibit uptake by 50%. These are standard terms known to those skilled in the art.

TABLE 1

| Inhibition of Monoamine Uptake by (1R,5S)-(+)-1-(naphthalen-2-yl)-3-azabicyclo[3.1.0]hexane | |
|---|---|
| Compound | $IC_{50}$, nM |
| Norepinephrine | 6 ± 1 |
| Dopamine | 38 ± 6 |
| Serotonin | 83 ± 12 |

(1R,5S)-(+)-1-(naphthalen-2-yl)-3-azabicyclo[3.1.0] hexane inhibited uptake by human monoamine transporters with a ratio of 1:6:14 for NE, DA and 5-HT.

Example III

Effect of (1R,5S)-(+)-1-(naphthalen-2-yl)-3-azabicyclo[3.1.0]hexane on Monoamine Transporters In Vivo To evaluate the effect of (1R,5S)-(+)-1-(naphthalen-2-yl)-3-azabicyclo[3.1.0]hexane on monoamine uptake transporters in vivo, microdialysis studies were performed in rat brain regions.

Microdialysis studies were conducted using male Wistar rats (250-300 g) bred at the Institute of Pharmacology, the Polish Academy of Sciences, Krakow, Poland. The rats (250-300 g) were housed on a 12 h/12 h light/dark cycle at a constant temperature and humidity, and were provided with food and water ad libitum. The microdialysis procedure has been previously described (Popik et al., 2006). Briefly, the rats were anaesthetized with ketamine (75 mg/kg IM) and xylazine (10 mg/kg IM), placed in a stereotaxic apparatus (David Kopf Instruments, Tujunga, CA, USA) with their skulls exposed. Small holes were drilled in the skull for insertion of the vertical microdialysis probes into the prefrontal cortex and striatum, respectively using the following coordinates: 2.9 mm anterior from the bregma, 0.8 mm lateral from the sagittal suture and −4.5 ventral from the dura surface (prefrontal cortex); 1.8 mm anterior from the bregma, 2.7 mm lateral from the sagittal suture and −7.0 mm ventral from the dura surface (striatum) (Paxinos and Watson, 1998). Microdialysis probes were constructed by inserting two fused silica tubes (30 and 35 mm long, 150 µm o.d.; Polymicro Technologies Inc., Phoenix, AZ, USA) into a microdialysis fiber (220 µm o.d.; AN69, Hospal, Bologna, Italy). The tube assembly was placed in a stainless steel cannula (22 G, 10 mm) forming the shaft of the probe. Portions of the inlet and outlet tubes were individually placed inside polyethylene PE-10 tubing and were glued for protection. The free end of the dialysis fibre was sealed, and 3 mm of the exposed length used for dialysis in prefrontal cortex and 4 mm for striatum. One day after the surgery and probe implantation, the inlet of the dialysis probes was connected to a syringe pump (BAS, IN, USA) which delivered an artificial cerebrospinal fluid (aCSF) composed of [in mM]: NaCl 145, KCl 2.7, $MgCl_2$ 1.0, $CaCl_2$ 1.2; pH=7.4 at a flow rate of 1.5 µl/min. After a two hour rinsing period to stabilize the extracellular level of neurotransmitters, 3-4 baseline samples were collected in 20 minute sampling periods. Next, (1R,5S)-(+)-1-(naphthalen-2-yl)-3-azabicyclo[3.1.0]hexane (dissolved in 0.9% saline solution) at doses of 10 or 20 mg/kg intraperioneally (i.p.) was administered to the animals at 4 ml/kg and consequent dialysate fractions were collected every 20 min for 3 hrs. At the end of the experiments the rats were sacrificed and their brains were histologically examined to validate the correct probe placement Dopamine, and serotonin (5-HT) were analysed by HPLC with electrochemical detection. Chromatography was performed using an LC-10 AD pump (Shimadzu Europa GmbH, Warszawa, Poland), an LC-4B amperometric detector with a cross-flow detector cell (BAS, IN, USA) and BDS-Hypersil C18 analytical column (3×100 mm, 3 µm, Thermo Electron Corp., UK). The mobile phase was composed of 0.1 M monochloracetic acid adjusted to pH=3.7 with 3 M sodium hydroxide, 0.5 mM EDTA, 25 mg/L 1-octanesulfonic acid sodium salt, 5.7% methanol, and 2.5% acetonitrile. The flow rate was 0.5 ml/min, and the applied potential of a 3 mm glassy carbon electrode was +600 mV with a sensitivity of 2 nA/V. Norepinephrine was measured using HPLC system equipped with a P580 pump (Dionex, CA, USA) connected to a BAS injection valve with a 10 µl injection loop and a BDS-Hypersil analytical column (2.0× 100 mm, a 3 µm, Thermo Electron Corp., UK). The mobile phase was composed of 0.05 M potassium dihydrogen phosphate (adjusted to pH=3.7 with ortho-phosphoric acid), 0.5 mM EDTA, 150 mg/L 1-octanesulfonic acid sodium salt, 10 mM NaCl, and 1.2% acetonitrile. The flow rate was 180 µl/min. NE in the dialysates was detected with a BAS UniJet radial flow detector cell coupled to a LC-4B amperometric detector (BAS, IN, USA). The applied potential of a 3-mm glassy carbon electrode was +600 mV with a sensitivity of 2 nA/V. The chromatographic data were processed by Chromax 2001 (Pol-Lab, Warszawa, Poland) software run on a personal computer. The values were not corrected for an in vitro probe recovery, which was approximately 15% for all investigated substances.

Figure 1B:
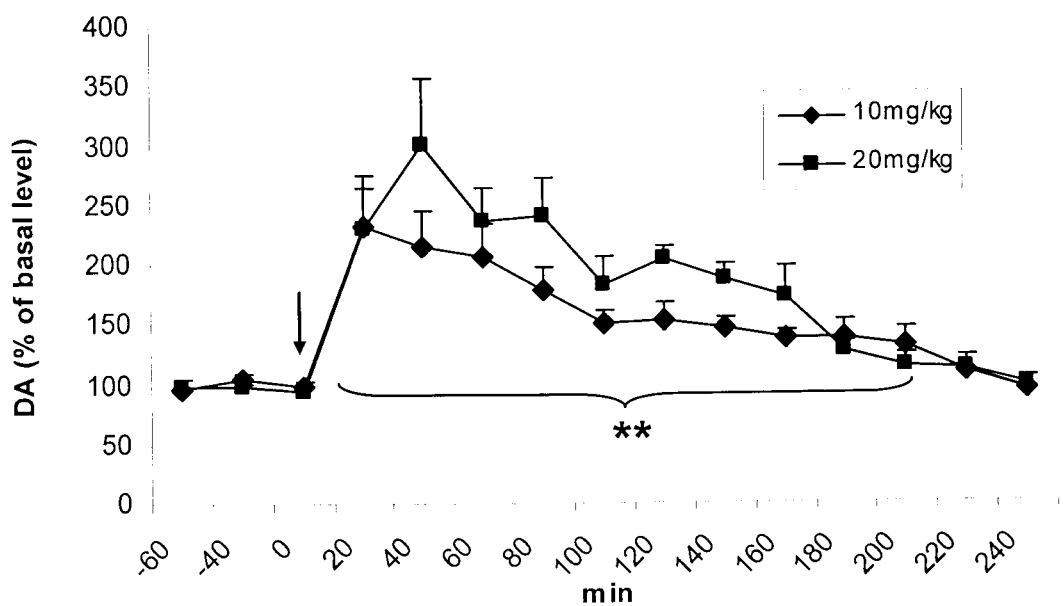
Figure 1C:
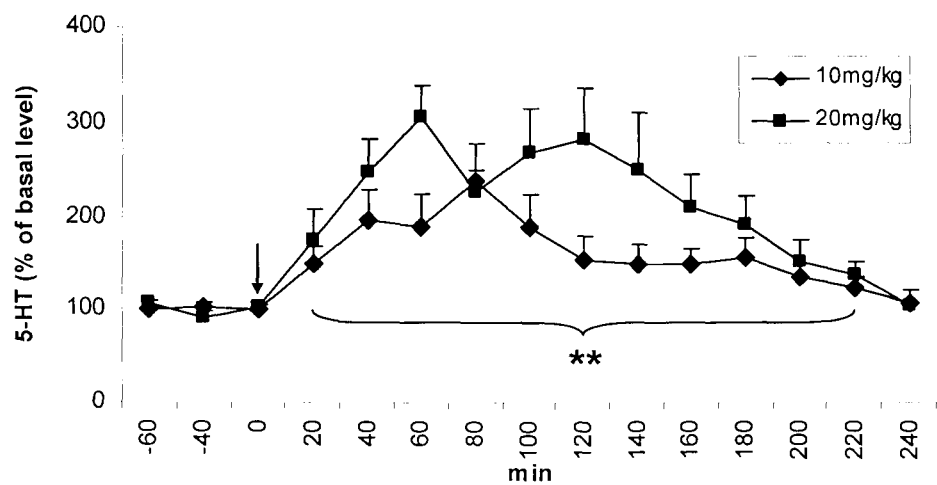

(1R,5S)-(+)-1-(naphthalen-2-yl)-3-azabicyclo[3.1.0]hexane (10 and 20 mg/kg i.p.) markedly increased extracellular concentrations of NE in rat prefrontal cortex 40 minutes after administration, had a peak increase of over 325 and 375% of baseline at the 10 and 20 mg/kg doses, respectively, and the increase was sustained over 3 hours (FIG. 1a). (1R,5S)-(+)-1-(naphthalen-2-yl)-3-azabicyclo[3.1.0]hexane increased extracellular concentrations of DA in prefrontal cortex by 20 minutes, the peak increase was from 240-300% of baseline for the two doses and the increase was sustained for over 3 hours (FIG. 1b). The extracellular concentrations of 5-HT were also markedly increased by (1R,5S)-(+)-1-(naphthalen-2-yl)-3-azabicyclo[3.1.0]hexane by 40 minutes and with a peak increase of 300% of baseline (FIG. 1c). The increase produced by the 20 mg/kg dose was delayed compared to the 10 mg/kg dose, and both doses had significant increases in 5-HT extracellular concentrations for over 3 hours.

Figure 2:
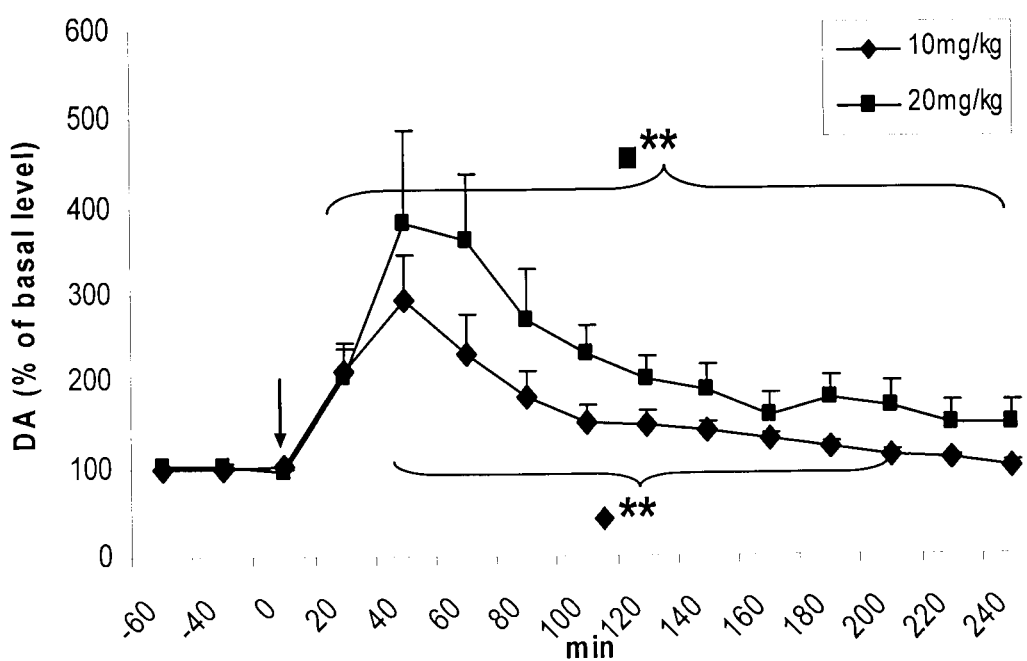
FIG. 2 is a graph showing that (1R,5S)-(+)-1-(naphthalen-2-yl)-3-azabicyclo[3.1.0]hexane increased extracellular concentrations of dopamine (DA) (FIG. 2A), in rat striatum. (1R,5S)-(+)-1-(naphthalen-2-yl)-3-azabicyclo[3.1.0]hexane was administered at time zero as indicated. Values are mean±SEM (n=6-8) percentage of baseline concentrations of respective monoamines. **<0.01 show significant difference in DA versus baseline.

In rat striatum, (1R,5S)-(+)-1-(naphthalen-2-yl)-3-azabicyclo[3.1.0]hexane markedly increased extracellular concentrations of DA within 40 minutes, had peak increases of over 275 and 375% of baseline for the 10 and 20 mg/kg doses (FIG. 2). The effect on DA extracellular concentrations persisted for over 3 hours. (1R,5S)-(+)-1-(naphthalen-2-yl)-3-azabicyclo[3.1.0]hexane similarly decreased extracellular concentrations of another metabolite of DA, HVA.

These data show that administration of (1R,5S)-(+)-1-(naphthalen-2-yl)-3-azabicyclo[3.1.0]hexane markedly increased extracellular concentrations of NE, DA and 5-HT in rat prefrontal cortex, as well as DA in striatum. These brain regions are thought to be involved in ADHD. Therefore these data support use of (1R,5S)-(+)-1-(naphthalen-2-yl)-3-azabicyclo[3.1.0]hexane in treating ADHD. The microdialysis data is consistent with a mechanism of action of triple uptake inhibition by (1R,5S)-(+)-1-(naphthalen-2-yl)-3-azabicyclo[3.1.0]hexane, and in agreement with its binding profile.

Example IV

Effect of (1R,5S)-(+)-1-(naphthalen-2-yl)-3-azabicyclo[3.1.0]hexane in a Mouse Model of Depression The behavioral effects of (1R,5S)-(+)-1-(naphthalen-2-yl)-3-azabicyclo[3.1.0]hexane were evaluated in a model predictive of antidepressant activity, the mouse tail suspension test (Cryan and Mombereau, 2004).

For the tail test suspension test, male CD-1 (Crl.) derived mice weighing 20-26 g were provided by BioLasco Taiwan (Charles River Laboratories Technology Licensee). All animals were maintained in a controlled temperature (23° C.-24° C.) and humidity (60%-70%) environment with 12 hours light dark cycles for at least one week prior to use. For the tail suspension test, (1R,5S)-(+)-1-(naphthalen-2-yl)-3-azabicyclo[3.1.0]hexane was administered orally at dose from 10-40 mg/kg p.o. to groups of 10 CD-1 derived male mice by MDS Pharma Services, Taipei, Taiwan 112, R. O. C. (1R,5S)-(+)-1-(naphthalen-2-yl)-3-azabicyclo[3.1.0]hexane was dissolved in 2% Tween 80 and was administered at 10 ml/kg 60 minutes prior to the tail suspension test.

During the test, the mice were suspended on the edge of a shelf 58 cm above a table top by adhesive tape placed approximately 1 cm from the tip of the tail. The duration of immobility was recorded for a period of 5 minutes (during 2-7 minutes of the tail suspension). The duration of the effects of (1R,5S)-(+)-1-(naphthalen-2-yl)-3-azabicyclo[3.1.0]hexane was also evaluated in the tail suspension test by varying pretreatment time.

Figure 3:
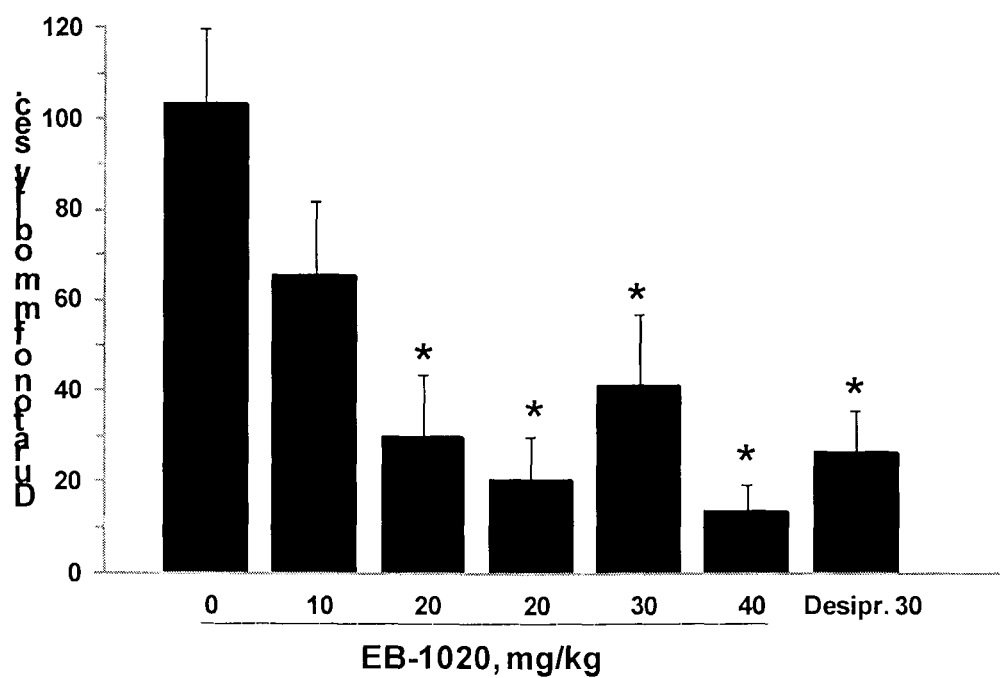
FIG. 3 is a graph showing a dose-dependent effect of (1R,5S)-(+)-1-(naphthalen-2-yl)-3-azabicyclo[3.1.0]hexane (EB-1020; 10-40 mg/kg p.o.) and desipramine (30 mg/kg p.o.) on immobility in a mouse tail suspension test. *=p<0.05 versus respective vehicle.
Figure 4:
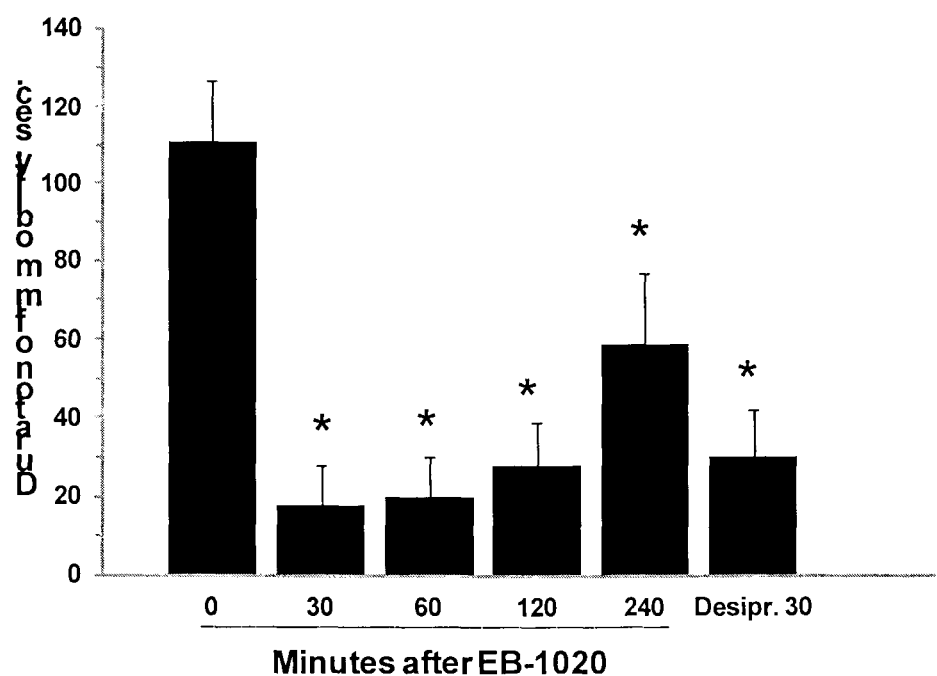
FIG. 4 is a graph showing the duration of effect of (1R,5S)-(+)-1-(naphthalen-2-yl)-3-azabicyclo[3.1.0]hexane (EB-1020; 20 mg/kg p.o.) in a mouse tail suspension test. Desipramine (30 mg/kg p.o.) was evaluated 1 hour after drug administration. *=p<0.05.

Oral administration of (1R,5S)-(+)-1-(naphthalen-2-yl)-3-azabicyclo[3.1.0]hexane dose-dependently reduced the amount of time immobilized with a minimal effective dose of 20 mg/kg and immobility was reduced to 87% of control levels at 40 mg/kg (FIG. 3). The efficacy of (1R,5S)-(+)-1-(naphthalen-2-yl)-3-azabicyclo[3.1.0]hexane was equivalent to the tricyclic antidepressant desipramine. The duration of effect of (1R,5S)-(+)-1-(naphthalen-2-yl)-3-azabicyclo[3.1.0]hexane in the tail suspension test was evaluated at 20 mg/kg p.o. and the drug significantly reduced immobility to 84, 82, 75 and 47% of control at 30, 60, 120 and 240 minutes (FIG. 4). (1R,5S)-(+)-1-(naphthalen-2-yl)-3-azabicyclo[3.1.0]hexane also reduced immobility of rats in the forced swim test at 40 mg/kg p.o. (data not shown).

Oral administration of (1R,5S)-(+)-1-(naphthalen-2-yl)-3-azabicyclo[3.1.0]hexane produced potent inhibition of immobility in the tail suspension test comparable to desipramine, and had a long duration of effect for over 4 hours in this test, indicating oral activity and a long duration of action. Inhibition of immobility in this acute test is considered to be predictive of antidepressant activity and suggests that (1R,5S)-(+)-1-(naphthalen-2-yl)-3-azabicyclo[3.1.0]hexane would have antidepressant activity (Cryan and Mombereau, 2004). Depression is a common co-morbidity in ADHD and is not well treated by stimulants. (1R,5S)-(+)-1-(naphthalen-2-yl)-3-azabicyclo[3.1.0]hexane may therefore effectively treat ADHD and depression.

Example V

Effect of (1R,5S)-(+)-1-(naphthalen-2-yl)-3-azabicyclo[3.1.0]hexane on Mouse Locomotor Activity The effect of (1R,5S)-(+)-1-(naphthalen-2-yl)-3-azabicyclo[3.1.0]hexane was evaluated in a mouse model of locomotor activity.

For the locomotor activity determination, male CD-1 (Crl.) derived mice were orally administered (1R,5S)-(+)-1-(naphthalen-2-yl)-3-azabicyclo[3.1.0]hexane as described in Example IV. Locomotor activity for mice in groups of 10 was assessed by placing mice individually into custom built chambers in a quiet isolated 22° C. room (conducted by MDS Pharma Services, Taipei, Taiwan 112, R. O. C.). At 15-minute intervals over 2 hours post-dosing, total travel distances (in cm) for individual animals were recorded using the Etho Vision Pro System (Noldus, USA).

Figure 5:
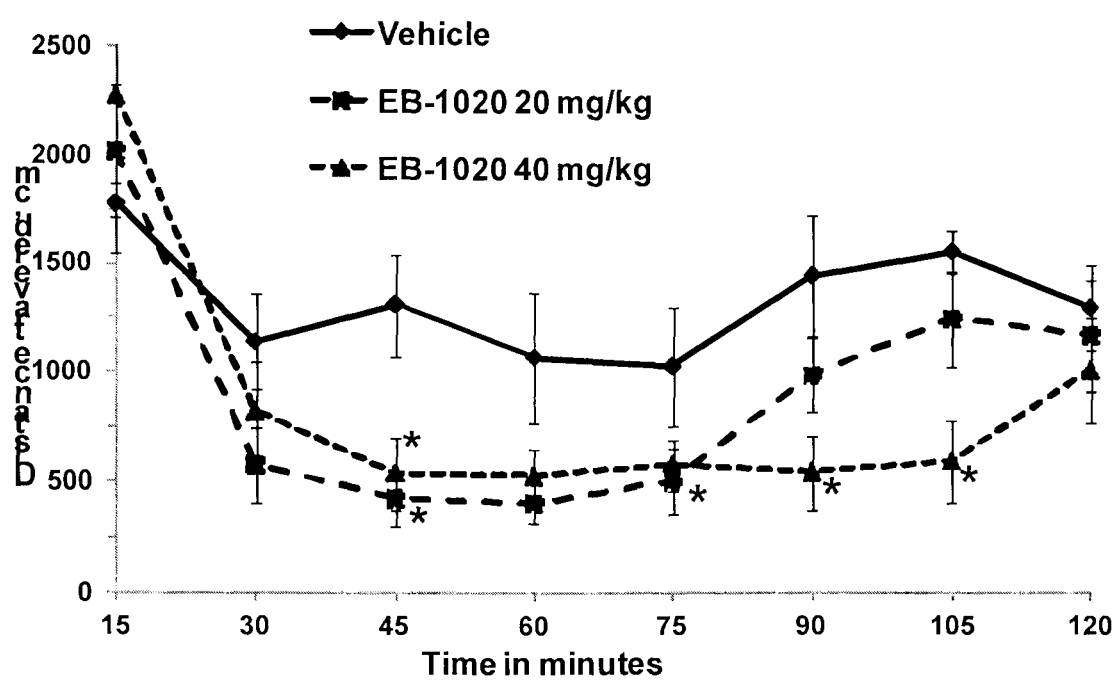
FIG. 5 is a graph showing that administration of (1R,5S)-(+)-1-(naphthalen-2-yl)-3-azabicyclo[3.1.0]hexane (EB-1020; 20, 40 mg/kg p.o.) decreased locomotor activity at several time points. Values are the mean (+S.E.) of distance traveled in 15 minute epochs. *=p<0.05 versus vehicle.

Oral administration of (1R,5S)-(+)-1-(naphthalen-2-yl)-3-azabicyclo[3.1.0]hexane did not significantly increase spontaneous locomotor activity of mice, but did significantly decrease locomotor activity at several time points (FIG. 5).

These data indicate that (1R,5S)-(+)-1-(naphthalen-2-yl)-3-azabicyclo[3.1.0]hexane has a low potential for abuse liability. Since (1R,5S)-(+)-1-(naphthalen-2-yl)-3-azabicyclo[3.1.0]hexane increased DA extracellular concentrations (see Example III), it might be expected to have stimulant-like activity and thereby increase locomotor activity, but this was not the case in the adult mice. Increases of DA in the ventral striatum have been hypothesized to be involved in both the locomotor-stimulating aspects of stimulants and their rewarding effects (Wise and Bozarth 1987). The results suggest that unlike stimulants, (1R,5S)-(+)-1-(naphthalen-2-yl)-3-azabicyclo[3.1.0]hexane would not be subject to drug abuse liability.

Example VI

Effect of (1R,5S)-(+)-1-(naphthalen-2-yl)-3-azabicyclo[3.1.0]hexane in a Model of ADHD The behavioral effects of (1R,5S)-(+)-1-(naphthalen-2-yl)-3-azabicyclo[3.1.0]hexane were evaluated in a model of ADHD, which can be simulated in juvenile rates with neonatal 6-hydroxydopamine (6-OHDA) lesions (Davids et al., 2003). In this animal model, the NE neurons are protected from the neurotoxic effects of 6-OHDA by pretreatment with the NE transporter inhibitor desipramine, so the NE system is largely intact and can respond to NE transporter inhibitors (Davids et al., 2002). Furthermore, the 6-OHDA lesions produce learning and memory deficits in learning models including the T maze, and active and passive avoidance tasks (Shaywitz et al., 1978; Wool et al., 1987; Takasuna and Iwasaki, 1996). Performance in these learning and memory models was improved by administration of stimulants (Shaywitz et al., 1978; Wool et al., 1987). Thus, this model incorporates both hyperactivity and learning deficits found in ADHD.

Methods of lesioning neonatal rats with 6-OHDA were carried out as detailed in Zhang et al. (2001). Briefly, on postnatal day 1 (PD 1), male Sprague-Dawley rat pups were randomly assigned to a nursing dam (10/dam). On PD 5, pups receive a subcutaneous injection of 25 mg/kg desipramine hydrochloride to protect noradrenergic neurons, followed in 45 min. by randomly assigned intracisternal injection of vehicle or 6-OHDA hydrobromide (100 µg free base) under hypothermic anesthesia. Pups were returned to nursing dams immediately after the intracranial injections. Locomotor activity was monitored individually for 90 min. in the periadolescent period on PD 25, using a microcomputer controlled infrared photobeam activity monitoring system. Locomotor activity was defined as breaking of consecutive photobeams and the activity accumulated in 5 minute bins. Behavioral testing was conducted in a novel environment (transparent plastic cages containing fresh bedding) within a grid of horizontal infrared beams. Each dose of (1R,5S)-(+)-1-(naphthalen-2-yl)-3-azabicyclo[3.1.0]hexane (1, 3 and 10 mg/kg) or methylphenidate (3 mg/kg) was dissolved in saline and given i.p. immediately prior to testing. The effects of sham versus 6-OHDA lesions on dopamine neurons in rats were quantified as decrements of DA transporters labeled with [31-1]2-(3-carbomethoxy-3-β-[4'-iodophenyl]tropane ([$^3$H]β-CIT), a selective DA transporter radioligand (Kula et al. 1999). Sections were preincubated (60 min., room temp [RT]) in 50 mM Tris-HCl buffer (pH 7.7) containing 120 mM NaCl and 4 mM $MgCl_2$, then in fresh buffer (60 min) containing 2 nM [3H](3-CIT. Nonspecific binding was defined with 1 µM GBR-12909. Slides were then washed (2×5 min) in ice-cold buffer, dipped in ice-cold water, and air-dried. Radiolabeled slides and calibrated [$^3$H]standards were exposed to [$^3$H]sensitive films for 10-14 d at 4° C. Tritium-sensitive Hyperfilms were developed and fixed in Kodak D-19 for 5 min. at RT. Images were quantified with a computer-controlled MCID image analyzer. Brain regions of interest were outlined and their optical density was measured with two sections representing total binding, with two samples representing nonspecific binding. Optical density of sampled regions was measured and the amount of ligand bound within each area was calculated as nCi/mg tissue. Mean values of non-specific binding in each region were subtracted from the mean total binding to determine specific binding, which was converted into fmol/mg of radioligand bound.

The levels of dopamine transporters in dopamine-rich areas of the lesioned rat brains were used as a marker for dopamine neurons and the 6-OHDA lesions in the neonatal rats resulted in a decrement of binding of [3H](β-CIT to dopamine transporters compared to sham injected rats at day 29 (Table 2). The binding in the 6-OHDA lesioned rats was markedly reduced to 25.7, 22.2 and 32.2% of control levels of sham-lesioned rats in lateral caudate-putamen, medial caudate-putamen, and nucleus accumbens septi, respectively.

TABLE 2

Effect of neonatal 6-OHDA lesioning on binding of [$^3$H]β-CIT to dopamine transporters quantified autoradiographically in juvenile rats

| Brain region | Sham controls | 6-OHDA Lesioned | % Sham Lesion |
|---|---|---|---|
| Lateral caudate-putamen | 120 ± 5.7 | 30.9 ± 2.4* | 25.7 |
| Medial caudate-putamen | 112 ± 8.9 | 24.9 ± 3.5* | 22.2 |
| Nucleus accumbens septi | 70.6 ± 3.4 | 22.8 ± 1.8* | 32.2 |

Figure 6:
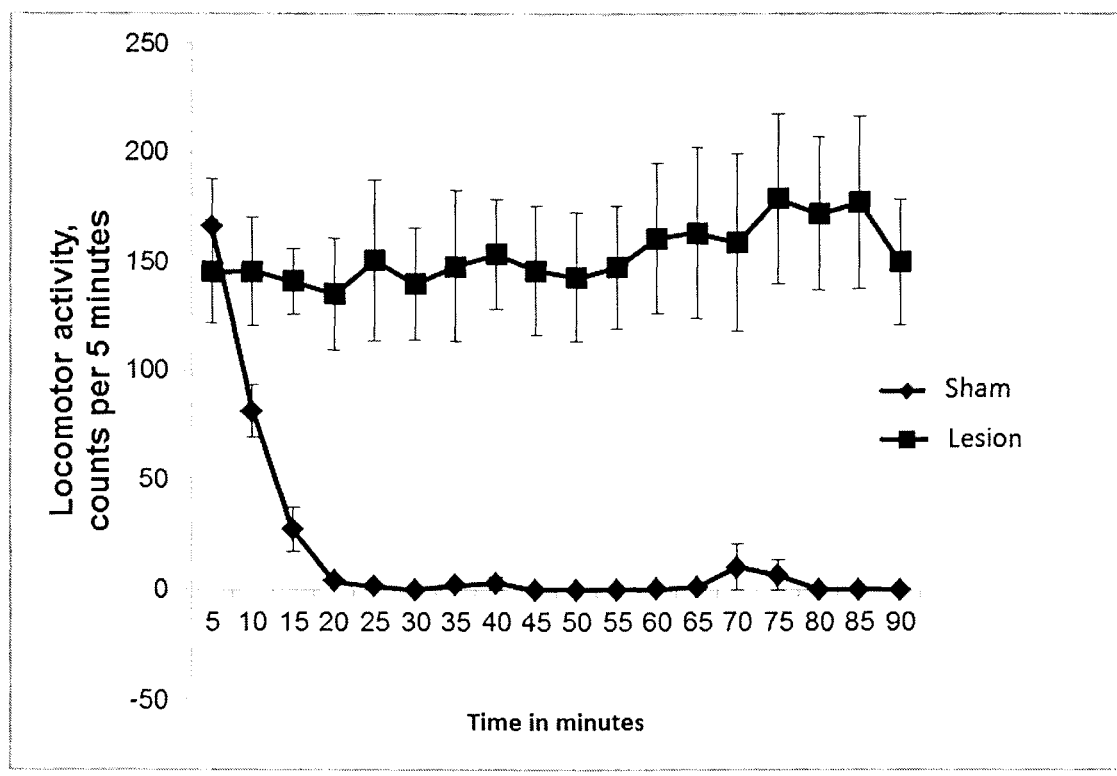
FIG. 6 is a graph showing that neonatal 6-OHDA lesions resulted in an increase in locomotor activity in periadolescent rats at PD 25 compared to sham-lesioned controls.

Data are specific binding (mean fmol/mg tissue ± SEM) for N = 10 – 12 rats;
*p < 0.001 vs. corresponding sham-lesioned controls Locomotor activity was monitored individually for 90 min. in the periadolescent period on PD 25. The 6-OHDA neonatal lesions resulted in a marked overall increase in locomotor activity in the periadolescent rats over the 90 minute testing period in a representative study (FIG. 6). Initially, locomotor activity was similar in sham and lesioned rats, but the sham-lesioned rats activity declined to a low level, whereas the lesioned rats locomotor activity remained stable over the 90 minute testing period. The cumulative locomotor scores for sham-lesioned rats and 6-OHDA-lesioned rats were 303.2+9.9 and 2758±3.0, respectively, a 9 fold difference (p<0.001).

Figure 7A:
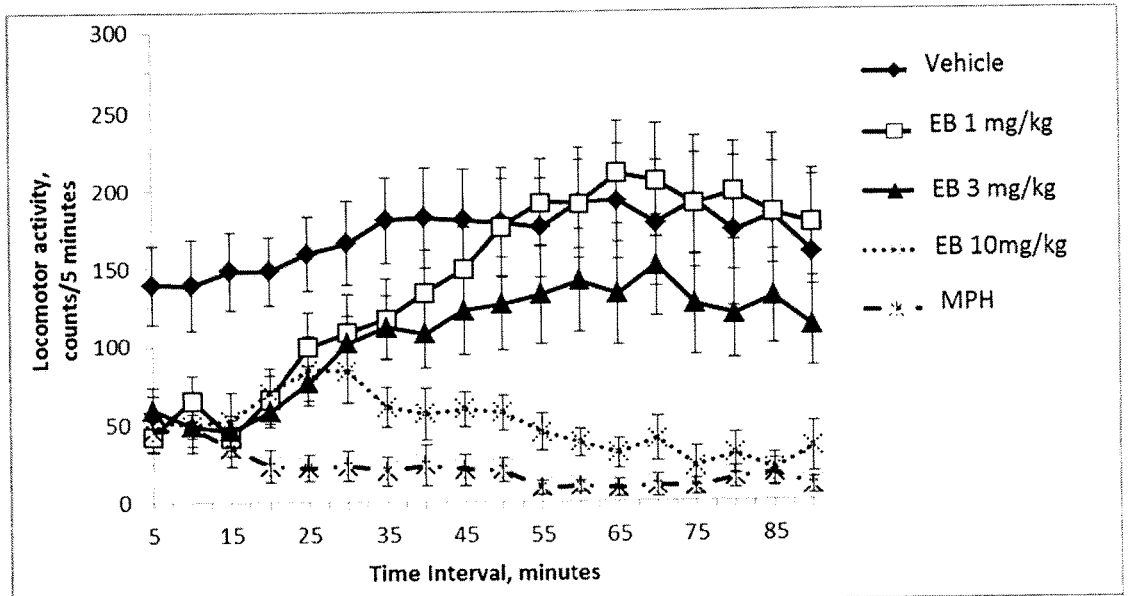
FIGS. 7A and 7B are graphs showing that administration of (1R,5S)-(+)-1-(naphthalen-2-yl)-3-azabicyclo[3.1.0] hexane (EB) and methylphenidate (MPH) reduced locomotor activity in 6-OHDA-lesioned juvenile rats at PD25.
Figure 7B:
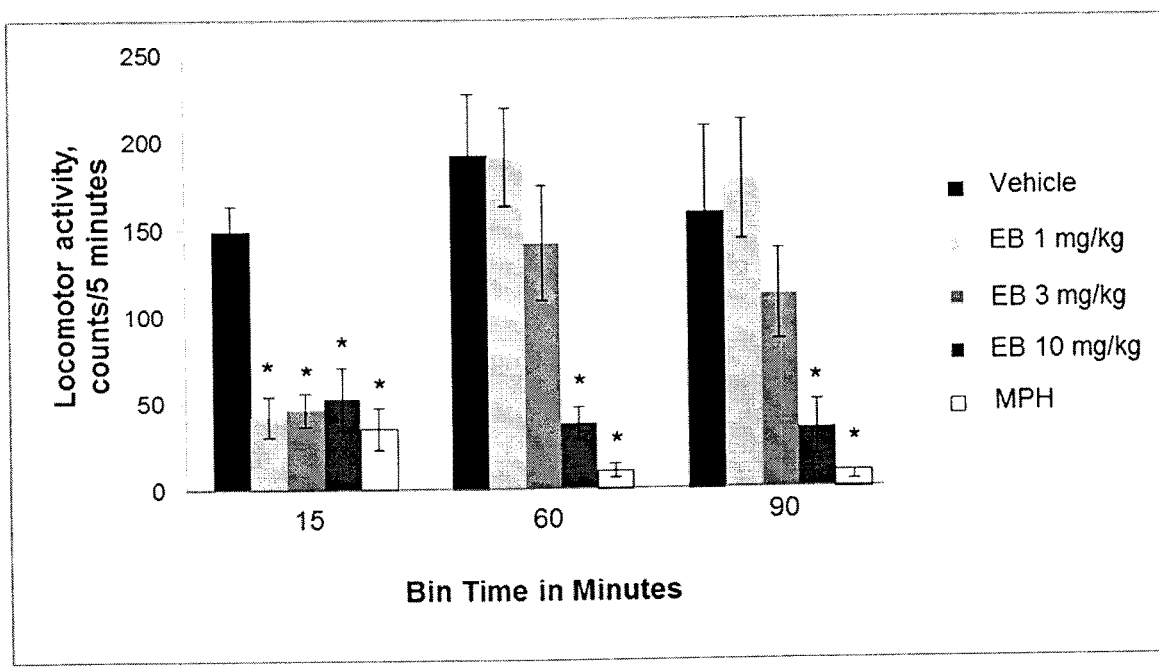

Compared to saline-treated controls, administration of 1 mg/kg (1R,5S)-(+)-1-(naphthalen-2-yl)-3-azabicyclo[3.1.0]hexane significantly reduced locomotor activity in the hyperactive 6-OHDA-lesioned juvenile rats for the first 35 minutes of behavioral testing, (FIG. 7a,b, *p<0.05). Administration of 3 mg/kg (1R,5S)-(+)-1-(naphthalen-2-yl)-3-azabicyclo[3.1.0]hexane produced a longer effect as this dose significantly attenuated locomotor hyperactivity in 6-OHDA-lesioned animals for 45 minutes after its administration. Administration of 10 mg/kg (1R,5S)-(+)-1-(naphthalen-2-yl)-3-azabicyclo[3.1.0]hexane produced a sustained and significant effect in reducing locomotor activity in the 6-OHDA-lesioned animals throughout the 90 min. of behavioral testing. Finally, administration of 3 mg/kg of methylphenidate produced significant attenuation of locomotor activity in 6-OHDA-lesioned animals for 90 min. of testing.

These data demonstrate that (1R,5S)-(+)-1-(naphthalen-2-yl)-3-azabicyclo[3.1.0]hexane dose-dependently inhibited the locomotor hyperactivity in juvenile rats lesioned with 6-OHDA as neonates. This inhibition by (1R,5S)-(+)-1-(naphthalen-2-yl)-3-azabicyclo[3.1.0]hexane is similar to that observed for stimulants and NE reuptake inhibitors (Davids et al., 2002). (1R,5S)-(+)-1-(naphthalen-2-yl)-3-azabicyclo[3.1.0]hexane may therefore be used to effectively treat ADHD.

Example VII

Efficacy of (1R,5S)-(+)-1-(naphthalen-2-yl)-3-azabicyclo[3.1.0]hexane in the Treatment of Adults with ADHD The efficacy of (1R,5S)-(+)-1-(naphthalen-2-yl)-3-azabicyclo[3.1.0]hexane in treating adult subjects for ADHD is assessed in a clinical study, similar to that described by Spencer et al., 1998. The study consists of a randomized, double-blind, placebo-controlled, crossover study of of (1R,5S)-(+)-1-(naphthalen-2-yl)-3-azabicyclo[3.1.0]hexane in the treatment of adults with ADHD.

Subjects between the ages of 19-60 years of age meet DSM-IV-TR criteria for ADHD, describe a chronic course of ADHD symptoms, and endorse impairment associated with ADHD. Criteria excluding potential subjects include clinically significant chronic medical conditions, abnormal baseline laboratory values, psychiatric disorders, drug or alcohol abuse, current use or use in the previous 3 months of psychotropic medication, and mental retardation.

The study design includes two four-week treatment periods separated by a two-week washout period. Study medication is administered at 100 mg/day (50 mg b.i.d.) in an oral formulation, either tablet or capsule. Subjects are seen and evaluated each week over the four-week treatment period. Prior to and throughout the trial, subjects are evaluated for safety parameters by a variety of measures including assessing blood pressure, heart rate, weight, medication accountability and tolerability, and adverse effects.

Efficacy is determined by measuring the change from the baseline of an ADHD rating scale, such as the ADHD Rating Scale or the Conners Adult ADHD Rating Scale (CAARS), which can be investigator rated or self rated. Efficacy in treating ADHD or improvement in ADHD is defined as a reduction in the rating scale score of approximately 30% or more at the endpoint of treatment, and a reduction that is at least 10%, preferably 15-20% greater than that observed with placebo. The statistical significance of results is analyzed using statistical methods known in the art.

Example VIII

Efficacy of (1R,5S)-(+)-1-(naphthalen-2-yl)-3-azabicyclo[3.1.0]hexane in the Treatment of Methamphetamine Dependence The efficacy of (1R,5S)-(+)-1-(naphthalen-2-yl)-3-azabicyclo[3.1.0]hexane in treating subjects for methamphetamine dependence is assessed in a clinical study, similar to that described by Elkashef et al., 2008. The study consists of a randomized, double-blind, placebo-controlled, two-arm study of of (1R,5S)-(+)-1-(naphthalen-2-yl)-3-azabicyclo[3.1.0]hexane in the treatment of adults with methamphentamine dependence.

Subjects between the ages of 18-65 years of age meet DSM-IV-TR criteria for methamphetamine dependence. Criteria excluding potential subjects include clinically significant chronic medical conditions, serious medical illness, seizure disorder, pregnancy or lactation, and psychiatric disorder that required ongoing medication (as assessed by Structured Clinical Interview for DSM-IV disorders).

The study design includes a two-week baseline period followed by 12 week treatment with either (1R,5S)-(+)-1-(naphthalen-2-yl)-3-azabicyclo[3.1.0]hexane or placebo. Study medication is administered at 100 mg/day (50 mg b.i.d.) in an oral formulation, either tablet or capsule. Subjects are seen three times each week over the 12-week treatment period, and provide urine samples for analysis of methamphetamine and creatinine, and to complete a substance abuse report. During the trial, subjects complete a weekly assessment of substance craving, such as the Brief Substance Craving Scale. Depression is assessed biweekly with the Hamilton Depression Rating Scale (HAMD). Assessment of addiction is made at baseline and the end of treatment with the Addiction Severity Index. ADHD symptoms are assessed at baseline and the end of treatment ADHD using a rating scale, such as the ADHD Rating Scale or the Conners Adult ADHD Rating Scale (CAARS). Prior to and throughout the trial, subjects are evaluated weekly for safety parameters by a variety of measures including assessing blood pressure, heart rate, weight, medication accountability and tolerability, and adverse effects.

The primary outcome of the study is assessment of participants who abstained from methamphetamine use during each week of treatment based on urine analysis. Efficacy is assessed by the percentage of subjects who had a methamphetamine-free week over each of the study weeks. Secondary outcomes of the study include substance craving (differences in the Brief Substance Craving Scale), depression (HAMD scores), addiction severity (differences in the Addiction Severity Index), and ADHD (ratings scale scores). The statistical significance of results is analyzed using statistical methods known in the art.

All publications and patents cited herein are incorporated herein by reference for the purpose of describing and disclosing, for example, the materials and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

REFERENCES

Adler L A, Spencer T, Faraone S V, Kessler R C, Howes M J and Biederman J, Validity of pilot adult ADHD Self-Report Scale (ASRS) to rate adult ADHD symptoms, *Annals of Clinical Psychiatry* 18 (2006), pp. 145-148

Arnsten A F. The Emerging Neurobiology of Attention Deficit Hyperactivity Disorder: The Key Role of the Prefrontal Association Cortex. J Pediatr. 2009; 154(5):I-S43.

Barkley R A, Fischer M, Smallish L, Fletcher K. Young adult outcome of hyperactive children: adaptive functioning in major life activities. J Am Acad Child Adolesc Psychiatry. 2006 February; 45(2):192-202.

Barkley R A, and Murphy, KR, Attention deficit/hyperactivity disorder: A clinical workbook (2nd ed.), Guildford Press, New York (1998).

Berman S M, Kuczenski R, McCracken J T, London E D. Potential adverse effects of amphetamine treatment on brain and behavior: a review. Mol Psychiatry. 2009 February; 14(2):123-42.

Brown T S, Brown attention deficit disorder scales, The Psychological Corporation, TX (1996).

Buitelaar J, Medori R. Treating attention-deficit/hyperactivity disorder beyond symptom control alone in children and adolescents: a review of the potential benefits of long-acting stimulants. Eur Child Adolesc Psychiatry. 2010 April; 19(4):325-40.

Bymaster F P, Katner J S, Nelson D L, Hemrick-Luecke S K, Threlkeld P G, Heiligenstein J H, Morin S M, Gehlert D R, Perry K W; Atomoxetine Increases Extracellular Levels of Norepinephrine and Dopamine in Prefrontal Cortex of Rat: A Potential Mechanism for Efficacy in Attention Deficit/Hyperactivity Disorder. Neuropsychopharmacology 27:699-711, 2002.

Caterino L., Gomez-Benito J., Balleurka N. and Amador-Campos J., Development and validation of a scale to assess the symptoms of attention-deficit/hyperactivity disorder in young adults, *Psychological Assessment* 21 (2009), pp. 152-161

Conners, C. K., Erhardt, D and Sparrow, E., Conners' adult ADHD rating scales, Technical Manual: Multi-Health Systems, New York, USA (1999).

Cryan J F, Mombereau C. In search of a depressed mouse: utility of models for studying depression-related behavior in genetically modified mice. Mol Psychiatry. 2004 April; 9(4):326-57.

Davids E, Zhang K, Kula N S, Tarazi F I, Baldessarini R J. Effects of norepinephrine and serotonin transporter inhibitors on hyperactivity induced by neonatal 6-hydroxydopamine lesioning in rats. J Pharmacol Exp Ther. 2002 June; 301(3):1097-102.

Davids E, Zhang K, Tarazi F I, Baldessarini R J. Animal models of attention-deficit hyperactivity disorder. Brain Res Brain Res Rev. 2003 April; 42(1):1-21

De Quiros G. B. and M. Kinsbourne M., Analysis of self-ratings on a behavior questionnaire, *Annals of the New York Academy of Sciences* 931 (2001), pp. 140-147.

Du Paul G J, Power T J, Anastopoulos A D and Reid R, ADHD rating scale-IV: Checklists norms and clinical interpretation, Guildford Press, New York (1998).

Du Paul G. J., Schaughency, E. A., Weyandt L. L., Tripp G., Kiesner J. and Ota K., Self-report of ADHD symptoms in university students: Cross-gender and cross-national prevalence, *Journal of Learning Disabilities* 34 (2001), pp. 370-379.

Elkashef et al., Bupropion for the Treatment of Methamphetamine Dependence. Neuropsychopharmacology (2008) 33, 1162-1170.

Eshleman A J, Carmolli M, Cumbay M, Martens C R, Neve K A, Janowsky A (1999) Characteristics of drug interactions with recombinant biogenic amine transporters expressed in the same cell type. J Pharmacol Exp Ther 289:877-85

Faraone S V, Biederman J. What is the prevalence of adult ADHD? Results of a population screen of 966 adults. J Atten Disord. 2005 November; 9(2):384-91.

Hammerness P, Georgiopoulos A, Doyle R L, Utzinger L, Schillinger M, Martelon M, Brodziak K, Biederman J, Wilens T E. An open study of adjunct OROS-methylphenidate in children who are atomoxetine partial responders: II. Tolerability and pharmacokinetics. J Child Adolesc Psychopharmacol. 2009 October; 19(5):493-9.

Hays et al., Bupropion Sustained Release for Treatment of Tobacco Dependence. Mayo Clin Proc. 2003; 78:1020-1024.

Kessler R C, Adler L, Barkley R, Biederman J, Conners C K, Demler O, Faraone S V, Greenhill L L, Howes M J, Secnik K, Spencer T, Ustun T B, Walters E E, Zaslavsky A M; The prevalence and correlates of adult ADHD in the United States: results from the National Comorbidity Survey Replication. Am J Psychiatry. 2006; 163(4):716-23.

Kula N S, Baldessarini R J, Tarazi F I, Fisser R, Wang S, Trometer J, Neumeyer J L. [3H]beta-CIT: a radioligand for dopamine transporters in rat brain tissue. Eur J Pharmacol. 1999 Dec. 3; 385(2-3):291-4.

McCann B S and Roy-Byrne P, Screening and diagnostic utility of self-report attention deficit hyperactivity disorder scales in adults, *Comprehensive Psychiatry* 45 (2004), pp. 175-183.

Mehringer A M, Downey, Schuh L M, Pomerleau C S, Snedecor S M and Schbiner H, The Assessment of Hyperactivity and Attention (AHA): Development and preliminary validation of a brief self-assessment of adult ADHD, *Journal of Attention Disorders* 5 (2002), pp. 223-231.

Paxinos, G., Watson, C. (1998) The Rat Brain in Stereotaxic Coordinates. Academic Press, New York.

Perovic S, Müller WE (1995) Pharmacological profile of hypericum extract. Effect on serotonin uptake by postsynaptic receptors. Arzneimittelforschung 45:1145-8.

Polanczyk G, de Lima M S, Horta B L, Biederman J, Rohde L A. The worldwide prevalence of ADHD: a systematic review and metaregression analysis. Am J Psychiatry. 2007 June; 164(6):942-8.

Popik P, Krawczyk M, Golembiowska K, Nowak G, Janowsky A, Skolnick P, Lippa A, Basile A S (2006) Pharmacological profile of the "triple" monoamine neurotransmitter uptake inhibitor, DOV 102,677. Cell Mol Neurobiol 26:857-73.

Scahill L, Schwab-Stone M. Epidemiology of ADHD in school-age children. Child Adolesc Psychiatr Clin N Am. 2000 July; 9(3):541-55, vii.

Shaywitz B A, Klopper J H, Gordon J W. Methylphenidate in 6-hydroxydopamine-treated developing rat pups. Effects on activity and maze performance. Arch Neurol. 1978 July; 35(7):463-9.

Spencer T J, Biederman J, Mick E. Attention-deficit/hyperactivity disorder: diagnosis, lifespan, comorbidities, and neurobiology. J Pediatr Psychol. 2007 July; 32(6):631-42.

Spencer T, Biederman J, Wilens T, Prince J, Hatch M, Jones J, Harding M, Faraone S V, Seidman L. Effectiveness and tolerability of tomoxetine in adults with attention deficit hyperactivity disorder. Am J Psychiatry. 1998 May; 155 (5):693-5.

Triolo S J and Murphy K R, Attention Deficit Scales for Adults (ADSA): Manual for scoring and interpretation, Bristol, Taylor and Francis, UK (1996).

Ward, M. F., Wender, P. H. and F. W. Reimherr F. W., The Wender Utah Rating Scale: An aid in the retrospective diagnosis of childhood attention deficit hyperactivity disorder, *American Journal of Psychiatry* 150 (1993), pp. 885-890.

Weyandt, L. L, Linterman, I. and Rice, J. A., Reported prevalence of attentional difficulties in a general sample of college students, *Journal of Psychopathology and Behavioural Assessment* 17 (1995), pp. 293-304.

Wilens T E, Hammerness P, Utzinger L, Schillinger M, Georgiopoulous A, Doyle R L, Martelon M, Brodziak K. An open study of adjunct OROS-methylphenidate in children and adolescents who are atomoxetine partial responders: I. Effectiveness. J Child Adolesc Psychopharmacol. 2009 October; 19(5):485-92.

Wise R A, Bozarth M A (1987) A psychomotor stimulant theory of addiction. Psychol Rev 94:469-92.

Wool R S, Weldon D A, Shaywitz B A, Anderson G M, Cohen D J, Teicher M H. Amphetamine reverses learning deficits in 6-hydroxydopamine-treated rat pups. Dev Psychobiol. 1987 March; 20(2):219-32.

Young S., The YAQ-S and YAQ-I: The development of self and informant questionnaires reporting on current adult ADHD symptomatology, comorbid and associated problems, *Personality and Individual Differences* 35 (2004), pp. 1211-1223.

Zhang K, Tarazi F I, Baldessarini R J. Role of dopamine D(4) receptors in motor hyperactivity induced by neonatal 6-hydroxydopamine lesions in rats. Neuropsychopharmacology. 2001 November; 25(5):624-32.

What is claimed is:

1. A method for treating ADHD or a related behavioral disorder in a subject comprising administering to a subject in need of treatment for ADHD or a related behavioral disorder a pharmaceutical composition comprising an effective amount of (1R,5S)-(+)-1-(naphthalen-2-yl)-3-azabicyclo[3.1.0]hexane or a pharmaceutically acceptable salt thereof in a bi-layer tablet dosage form for sustained delivery of the (1R,5S)-(+)-1-(naphthalen-2-yl)-3-azabicyclo[3.1.0]hexane or of the pharmaceutically acceptable salt, wherein:
the bi-layer table comprises an immediate release and a slow-release layer.

2. The method according to claim 1, wherein the ADHD is selected from the group consisting of Attention Deficit Hyperactivity Disorder-predominantly hyperactive-impulsive subtype, Attention Deficit Hyperactivity Disorder-predominantly inattentive subtype, and Attention Deficit Hyperactivity Disorder-combined subtype.

3. The method according to claim 1, wherein the related behavioral disorder is selected from the group consisting of Conduct Disorder and Oppositional Defiant Disorder.

4. The method according to claim 1, wherein the subject is a human child, adolescent, or adult.

5. The method according to claim 4, wherein the subject is an adult.

6. The method according to claim 4, wherein the subject is a child.

7. The method according to claim 1, wherein the slow-release layer includes pH sensitive polymers.

8. The method according to claim 7, wherein the pH sensitive polymers have a high degree of swelling in contact with water or aqueous media such as the stomach contents.

9. The method according to claim 1, wherein the effective amount is effective to decrease ADHD symptoms.

10. The method according to claim 9, wherein the effective amount is effective to decrease the subject's score on an ADHD rating scale.

11. The method according to claim 1, wherein the (1R,5S)-(+)-1-(naphthalen-2-yl)-3-azabicyclo[3.1.0]hexane or pharmaceutically acceptable salt thereof has no more than 2% w/w of the corresponding (−) enantiomer.

12. The method according to claim 1, wherein the (1R,5S)-(+)-1-(naphthalen-2-yl)-3-azabicyclo[3.1.0]hexane or pharmaceutically acceptable salt thereof has no more than 1% w/w of the corresponding (−) enantiomer.

13. The method according to claim 1, wherein the pharmaceutically acceptable salt is a hydrochloride salt.

* * * * *